US007923250B2

(12) United States Patent
McKay et al.

(10) Patent No.: US 7,923,250 B2
(45) Date of Patent: Apr. 12, 2011

(54) METHODS OF EXPRESSING LIM MINERALIZATION PROTEIN IN NON-OSSEOUS CELLS

(75) Inventors: William F. McKay, Memphis, TN (US); Scott Boden, Atlanta, GA (US); Sangwook T. Yoon, Decatur, GA (US)

(73) Assignee: Warsaw Orthopedic, Inc.

( * ) Notice: Subject to any disclaimer, the term of this patent is extended or adjusted under 35 U.S.C. 154(b) by 958 days.

(21) Appl. No.: 10/292,951

(22) Filed: Nov. 13, 2002

(65) Prior Publication Data

US 2003/0180266 A1 Sep. 25, 2003
US 2010/0239545 A9 Sep. 23, 2010

Related U.S. Application Data

(60) Continuation-in-part of application No. 09/959,578, filed on Apr. 28, 2000, now Pat. No. 7,045,614, and a continuation-in-part of application No. 09/986,625, filed on Nov. 9, 2001, now Pat. No. 6,858,431, which is a division of application No. 09/721,975, filed on Nov. 27, 2000, now Pat. No. 6,444,803, which is a continuation of application No. 09/124,238, filed on Jul. 29, 1998, now Pat. No. 6,300,127.

(60) Provisional application No. 60/054,219, filed on Jul. 30, 1997, provisional application No. 60/080,407, filed on Apr. 2, 1998, provisional application No. 60/331,321, filed on Nov. 14, 2001.

(51) Int. Cl.
*C12N 15/00* (2006.01)

(52) U.S. Cl. .......................... 435/455; 435/456

(58) Field of Classification Search ................ 435/69.1, 435/320.1, 325, 455, 6, 456; 536/23.1, 23.5; 424/93.1, 93.2, 93.21; 514/44
See application file for complete search history.

(56) References Cited

U.S. PATENT DOCUMENTS

| | | | |
|---|---|---|---|
| 4,137,921 A | 2/1979 | Okuzumi et al. | 606/230 |
| 4,166,800 A | 9/1979 | Fong | 427/212 |
| 4,181,983 A | 1/1980 | Kulkarni | 424/423 |
| 4,243,775 A | 1/1981 | Rosensaft et al. | 525/415 |
| 4,279,249 A | 7/1981 | Vert et al. | 606/77 |
| 4,294,753 A | 10/1981 | Urist | 530/395 |
| 4,300,565 A | 11/1981 | Rosensaft et al. | 606/224 |
| 4,347,234 A | 8/1982 | Wahlig et al. | 424/476 |
| 4,384,975 A | 5/1983 | Fong | 427/213.36 |
| 4,390,519 A | 6/1983 | Sawyer | 424/447 |
| 4,394,448 A | 7/1983 | Szoka, Jr. et al. | 435/456 |
| 4,409,332 A | 10/1983 | Jefferies et al. | 435/188 |
| 4,434,094 A | 2/1984 | Seyedin et al. | 530/146 |
| 4,455,256 A | 6/1984 | Urist | 530/350 |
| 4,472,840 A | 9/1984 | Jefferies | 128/898 |
| 4,530,449 A | 7/1985 | Nozawa et al. | 222/189.1 |
| 4,538,603 A | 9/1985 | Pawelchak et al. | 602/56 |
| 4,539,981 A | 9/1985 | Tunc | 606/77 |
| 4,563,350 A | 1/1986 | Nathan et al. | 424/599 |
| 4,563,489 A | 1/1986 | Urist | 514/21 |
| 4,568,559 A | 2/1986 | Nuwayser et al. | 427/2.15 |
| 4,578,384 A | 3/1986 | Hollinger | 514/8 |
| 4,585,797 A | 4/1986 | Cioca | 514/773 |
| 4,591,501 A | 5/1986 | Cioca | 429/401 |
| 4,596,574 A | 6/1986 | Urist | 424/422 |
| 4,608,199 A | 8/1986 | Caplan et al. | 530/414 |
| 4,619,989 A | 10/1986 | Urist | 530/417 |
| 4,623,588 A | 11/1986 | Nuwayser et al. | 428/402.24 |
| 4,627,982 A | 12/1986 | Seyedin et al. | 424/549 |
| 4,703,108 A | 10/1987 | Silver et al. | 530/356 |
| 4,711,783 A | 12/1987 | Huc et al. | 424/460 |
| 4,741,337 A | 5/1988 | Smith et al. | 606/220 |
| 4,744,365 A | 5/1988 | Kaplan et al. | 626/230 |
| 4,761,471 A | 8/1988 | Urist | 530/350 |
| 4,776,890 A | 10/1988 | Chu | 106/151.1 |
| 4,789,732 A | 12/1988 | Urist | 530/350 |
| 4,795,804 A | 1/1989 | Urist | 514/424.1 |
| 4,798,786 A | 1/1989 | Tice et al. | |
| 4,800,159 A | 1/1989 | Mullis et al. | |
| 4,804,744 A | 2/1989 | Sen | |
| 4,806,523 A | 2/1989 | Bentz et al. | |
| 4,816,437 A | 3/1989 | Nimberg et al. | |
| 4,818,542 A | 4/1989 | DeLuca et al. | |
| 4,833,125 A | 5/1989 | Neer et al. | |
| 4,837,285 A | 6/1989 | Berg et al. | |
| 4,839,130 A | 6/1989 | Kaplan et al. | |
| 4,844,854 A | 7/1989 | Kaplan et al. | |
| 4,865,846 A | 9/1989 | Kaufman | |
| 4,877,864 A | 10/1989 | Wang et al. | |

(Continued)

FOREIGN PATENT DOCUMENTS

EP 0 606 376 7/1994

(Continued)

OTHER PUBLICATIONS

Sobajima et al Gene Ther. 11(4):390-401, 2004.*
Check Nature 422:7, 2003.*
Couzin et al, Science 307:1028, 2005.*
Rosenberg et al, Science 287:1751, 2000.*
Anderson, Nature 392:25-30, 1998.*
Touchette, Nat. Med. 2(1) 7-8, 1996.*
Juengst BMJ, 326:1410-11, 2003.*
Boden et al Spine 23(23):2486-2492, 1998.*
Biology of Lumbar Spine Fusion and Use of Bone Graft Substitutes: Present, Future, and Next Generation 2000Tissue Engineering pp. 383-399.*

(Continued)

*Primary Examiner* — Maria Leavitt

(57) ABSTRACT

Methods of expressing LIM mineralization protein in non-osseous mammalian cells, such as stem cells or intervertebral disc cells (e.g., cells of the annulus fibrosus, or cells of the nucleus pulposus) are described. The methods involve transfecting the cells with an isolated nucleic acid comprising a nucleotide sequence encoding a LIM mineralization protein operably linked to a promoter. Transfection may be accomplished ex vivo or in vivo by direct injection of virus or naked DNA, or by a nonviral vector such as a plasmid. Expression of the LIM mineralization protein can stimulate proteoglycan and/or collagen production in cells capable of producing proteoglycyan and/or collagen. Methods for treating disc disease associated with trauma or disc degeneration are also described.

14 Claims, 11 Drawing Sheets

U.S. PATENT DOCUMENTS

| | | |
|---|---|---|
| 4,882,150 A | 11/1989 | Kaufman |
| 4,889,119 A | 12/1989 | Jamiolkowski et al. |
| 4,898,186 A | 2/1990 | Ikada et al. |
| 4,898,734 A | 2/1990 | Mathiowitz et al. |
| 4,902,508 A | 2/1990 | Badylak et al. |
| 4,916,193 A | 4/1990 | Tang et al. |
| 4,938,763 A | 7/1990 | Dunn et al. |
| 4,946,450 A | 8/1990 | Erwin |
| 4,952,402 A | 8/1990 | Sparks et al. |
| 4,956,178 A | 9/1990 | Badylak et al. |
| 4,957,902 A | 9/1990 | Grinnell |
| 4,961,707 A | 10/1990 | Magnusson et al. |
| 4,968,590 A | 11/1990 | Kuberasampath et al. |
| 4,975,527 A | 12/1990 | Koezuka et al. |
| 4,988,358 A | 1/1991 | Eppley et al. |
| 5,001,169 A | 3/1991 | Nathan et al. |
| 5,004,602 A | 4/1991 | Hutchinson |
| 5,007,939 A | 4/1991 | Delcommune et al. |
| 5,011,691 A | 4/1991 | Oppermann et al. |
| 5,011,692 A | 4/1991 | Fujioka et al. |
| 5,013,649 A | 5/1991 | Wang et al. |
| 5,035,893 A | 7/1991 | Shioya et al. |
| 5,037,749 A | 8/1991 | Findlay |
| 5,039,660 A | 8/1991 | Leonard et al. |
| 5,041,138 A | 8/1991 | Vacanti et al. |
| 5,051,272 A | 9/1991 | Hermes et al. |
| 5,059,123 A | 10/1991 | Jernberg |
| 5,077,049 A | 12/1991 | Dunn et al. |
| 5,080,665 A | 1/1992 | Jarrett et al. |
| 5,081,028 A | 1/1992 | Hofstetter et al. |
| 5,081,106 A | 1/1992 | Bentley et al. |
| 5,084,051 A | 1/1992 | Törmälä et al. |
| 5,103,840 A | 4/1992 | Kavoussi |
| 5,106,626 A | 4/1992 | Parsons et al. |
| 5,106,748 A | 4/1992 | Wozney et al. |
| 5,108,753 A | 4/1992 | Kuberasampath et al. |
| 5,108,755 A | 4/1992 | Daniels et al. |
| 5,108,922 A | 4/1992 | Wang et al. |
| 5,110,604 A | 5/1992 | Chu et al. |
| 5,116,738 A | 5/1992 | Wang et al. |
| 5,118,667 A | 6/1992 | Adams et al. |
| 5,120,322 A | 6/1992 | Davis et al. |
| 5,124,155 A | 6/1992 | Reich |
| 5,128,136 A | 7/1992 | Bentley et al. |
| 5,128,326 A | 7/1992 | Balazs et al. |
| 5,133,755 A | 7/1992 | Brekke |
| 5,137,669 A | 8/1992 | Leonard et al. |
| 5,141,905 A | 8/1992 | Rosen et al. |
| 5,143,730 A | 9/1992 | Fues et al. |
| 5,162,114 A | 11/1992 | Kuberasampath et al. |
| 5,162,430 A | 11/1992 | Rhee et al. |
| 5,164,368 A | 11/1992 | Recker |
| 5,166,058 A | 11/1992 | Wang et al. |
| 5,168,050 A | 12/1992 | Hammonds, Jr. et al. |
| 5,169,837 A | 12/1992 | Lagarde et al. |
| 5,171,217 A | 12/1992 | March et al. |
| 5,171,574 A | 12/1992 | Kuberasampath et al. |
| 5,171,579 A | 12/1992 | Ron et al. |
| 5,171,670 A | 12/1992 | Kronenberg et al. |
| 5,185,152 A | 2/1993 | Peyman |
| 5,187,076 A | 2/1993 | Wozney et al. |
| 5,192,741 A | 3/1993 | Orsolini et al. |
| 5,196,185 A | 3/1993 | Silver et al. |
| 5,197,977 A | 3/1993 | Hoffman, Jr. et al. |
| 5,200,313 A | 4/1993 | Carrico |
| 5,206,028 A | 4/1993 | Li |
| 5,208,041 A | 5/1993 | Sindrey |
| 5,219,740 A | 6/1993 | Miller et al. |
| 5,223,263 A | 6/1993 | Hostetler et al. |
| 5,227,157 A | 7/1993 | McGinity et al. |
| 5,236,456 A | 8/1993 | O'Leary et al. |
| 5,250,302 A | 10/1993 | Oppermann et al. |
| 5,250,584 A | 10/1993 | Ikada et al. |
| 5,258,494 A | 11/1993 | Oppermann et al. |
| 5,263,985 A | 11/1993 | Bao et al. |
| 5,264,618 A | 11/1993 | Felgner et al. ............... 560/224 |
| 5,264,985 A | 11/1993 | Felgner et al. |
| 5,266,618 A | 11/1993 | Oppermann et al. |
| 5,266,683 A | 11/1993 | Oppermann et al. ......... 530/326 |
| 5,268,178 A | 12/1993 | Calhoun et al. |
| 5,271,961 A | 12/1993 | Mathiowitz et al. |
| 5,273,964 A | 12/1993 | Lemons |
| 5,275,826 A | 1/1994 | Badylak et al. |
| 5,278,201 A | 1/1994 | Dunn et al. |
| 5,278,202 A | 1/1994 | Dunn et al. |
| 5,281,419 A | 1/1994 | Tuan et al. |
| 5,281,422 A | 1/1994 | Badylak et al. |
| 5,284,655 A | 2/1994 | Bogdansky et al. |
| 5,286,634 A | 2/1994 | Stadler et al. |
| 5,288,496 A | 2/1994 | Lewis |
| 5,290,558 A | 3/1994 | O'Leary et al. |
| 5,292,802 A | 3/1994 | Rhee et al. |
| 5,298,254 A | 3/1994 | Prewett et al. |
| 5,298,422 A | 3/1994 | Schwartz et al. |
| 5,306,303 A | 4/1994 | Lynch |
| 5,308,623 A | 5/1994 | Fues et al. |
| 5,308,889 A | 5/1994 | Rhee et al. |
| 5,317,010 A | 5/1994 | Pang et al. |
| 5,320,624 A | 6/1994 | Kaplan et al. |
| 5,324,307 A | 6/1994 | Jarrett et al. |
| 5,324,519 A | 6/1994 | Dunn et al. |
| 5,324,520 A | 6/1994 | Dunn et al. |
| 5,324,775 A | 6/1994 | Rhee et al. |
| 5,324,819 A | 6/1994 | Oppermann et al. |
| 5,326,350 A | 7/1994 | Li |
| 5,326,357 A | 7/1994 | Kandel |
| 5,328,955 A | 7/1994 | Rhee et al. |
| 5,344,654 A | 9/1994 | Rueger et al. |
| 5,350,580 A | 9/1994 | Muchow et al. |
| 5,352,463 A | 10/1994 | Badylak et al. |
| 5,354,557 A | 10/1994 | Oppermann et al. |
| 5,360,610 A | 11/1994 | Tice et al. |
| 5,362,478 A | 11/1994 | Desai et al. |
| 5,366,508 A | 11/1994 | Brekke |
| 5,366,733 A | 11/1994 | Brizzolara et al. |
| 5,366,734 A | 11/1994 | Hutchinson |
| 5,366,875 A | 11/1994 | Wozney et al. |
| 5,368,858 A | 11/1994 | Hunziker |
| 5,372,821 A | 12/1994 | Badylak et al. |
| 5,374,544 A | 12/1994 | Schwartz et al. |
| 5,376,118 A | 12/1994 | Kaplan et al. |
| 5,393,739 A | 2/1995 | Bentz et al. |
| 5,395,620 A | 3/1995 | Huc et al. |
| 5,403,825 A | 4/1995 | Lagarde et al. |
| 5,409,896 A | 4/1995 | Ammann et al. |
| 5,411,941 A | 5/1995 | Grinna et al. |
| 5,428,132 A | 6/1995 | Hirsch et al. |
| 5,439,686 A | 8/1995 | Desai et al. |
| 5,445,833 A | 8/1995 | Badylak et al. |
| 5,445,941 A | 8/1995 | Yang |
| 5,459,047 A | 10/1995 | Wozney et al. |
| 5,461,034 A | 10/1995 | Rodan et al. |
| 5,470,829 A | 11/1995 | Prisell et al. |
| 5,498,421 A | 3/1996 | Grinstaff et al. |
| 5,504,192 A | 4/1996 | Gill et al. |
| 5,510,396 A | 4/1996 | Prewett et al. |
| 5,513,662 A | 5/1996 | Morse et al. |
| 5,516,654 A | 5/1996 | Israel |
| 5,520,923 A | 5/1996 | Tija et al. |
| 5,521,067 A | 5/1996 | Seshi |
| 5,525,359 A | 6/1996 | Allard et al. |
| 5,529,914 A | 6/1996 | Hubbell et al. |
| 5,543,158 A | 8/1996 | Gref et al. |
| 5,543,394 A | 8/1996 | Wozney et al. |
| 5,547,932 A | 8/1996 | Curiel et al. |
| 5,573,934 A | 11/1996 | Hubbell et al. |
| 5,578,567 A | 11/1996 | Cardinaux et al. |
| 5,578,569 A | 11/1996 | Tam |
| 5,578,708 A | 11/1996 | Okazaki et al. |
| 5,580,775 A | 12/1996 | Fremeau, Jr. et al. |
| 5,580,859 A | 12/1996 | Felgner et al. |
| 5,585,237 A | 12/1996 | Oppermann et al. |
| 5,589,466 A | 12/1996 | Felgner et al. |
| 5,597,897 A | 1/1997 | Ron et al. |
| 5,614,385 A | 3/1997 | Oppermann et al. |
| 5,618,924 A | 4/1997 | Wang et al. |
| 5,620,867 A | 4/1997 | Kiefer et al. |

| | | | |
|---|---|---|---|
| 5,626,611 A | 5/1997 | Liu et al. | |
| 5,631,142 A | 5/1997 | Wang et al. | |
| 5,633,426 A | 5/1997 | Namikawa et al. | |
| 5,635,372 A | 6/1997 | Celeste et al. | |
| 5,635,373 A | 6/1997 | Wozney et al. | |
| 5,635,380 A | 6/1997 | Naftilan et al. | |
| 5,637,480 A | 6/1997 | Celeste et al. | |
| 5,639,638 A | 6/1997 | Wozney et al. | |
| 5,641,662 A | 6/1997 | Debs et al. | |
| 5,645,591 A | 7/1997 | Kuberasampath et al. | |
| 5,646,016 A | 7/1997 | McCoy et al. | |
| 5,650,173 A | 7/1997 | Ramstack et al. | |
| 5,650,276 A | 7/1997 | Smart et al. | |
| 5,656,593 A | 8/1997 | Kuberasampath et al. | |
| 5,656,728 A | 8/1997 | Stashenko et al. | |
| 5,658,593 A | 8/1997 | Orly et al. | |
| 5,661,007 A | 8/1997 | Wozney et al. | |
| 5,670,336 A | 9/1997 | Oppermann et al. | |
| 5,672,344 A | 9/1997 | Kelley et al. | |
| 5,679,377 A | 10/1997 | Bernstein et al. | |
| 5,688,678 A | 11/1997 | Hewick et al. | |
| 5,693,622 A | 12/1997 | Wolff et al. | |
| 5,693,779 A | 12/1997 | Moos, Jr. et al. | |
| 5,700,911 A | 12/1997 | Wozney et al. | |
| 5,703,043 A | 12/1997 | Celeste et al. | |
| 5,703,055 A | 12/1997 | Felgner et al. | |
| 5,705,270 A | 1/1998 | Soon-Shiong et al. | |
| 5,705,385 A | 1/1998 | Bally et al. | |
| 5,709,854 A | 1/1998 | Griffith-Cima et al. | |
| 5,712,119 A | 1/1998 | Oppermann et al. | |
| 5,714,589 A | 2/1998 | Oppermann et al. | |
| 5,728,679 A | 3/1998 | Celeste et al. | |
| 5,756,476 A | 5/1998 | Epstein et al. | |
| 5,763,416 A | 6/1998 | Bonadio et al. | |
| 5,770,580 A | 6/1998 | Ledley et al. | |
| 5,786,327 A | 7/1998 | Tam | |
| 5,786,340 A | 7/1998 | Henning et al. | |
| 5,792,477 A | 8/1998 | Rickey et al. | |
| 5,792,751 A | 8/1998 | Ledley et al. | |
| 5,801,028 A | 9/1998 | Bressan et al. | 800/279 |
| 5,801,231 A | 9/1998 | Derynck et al. | |
| 6,300,127 B1 | 10/2001 | Hair et al. | 536/23.1 |
| 6,444,803 B1 | 9/2002 | Hair et al. | 536/23.5 |
| 6,521,750 B2 | 2/2003 | Hair et al. | 536/23.5 |
| 2001/0006948 A1* | 7/2001 | Kang et al. | 514/44 |

FOREIGN PATENT DOCUMENTS

| | | |
|---|---|---|
| EP | 0 614 974 | 9/1994 |
| EP | 0 727 487 | 8/1996 |
| EP | 0 761 233 | 3/1997 |
| WO | WO 90/03733 | 4/1990 |
| WO | WO 90/11092 | 10/1990 |
| WO | WO 90/14074 | 11/1990 |
| WO | WO 91/17424 | 11/1991 |
| WO | WO 92/17165 | 10/1992 |
| WO | WO 93/05751 | 4/1993 |
| WO | WO 93/09229 | 5/1993 |
| WO | WO 93/14778 | 8/1993 |
| WO | WO 93/15109 | 8/1993 |
| WO | WO 93/16739 | 9/1993 |
| WO | WO 94/01139 | 1/1994 |
| WO | WO 94/20615 | 9/1994 |
| WO | WO 94/23699 | 10/1994 |
| WO | WO 94/23738 | 10/1994 |
| WO | WO 95/29411 | 10/1995 |
| WO | WO 99/06563 * | 2/1999 |
| WO | WO 00/66178 | 11/2000 |

OTHER PUBLICATIONS

Boden et al Spine Dec. 1, 1998;23(23):2486-92.Lumbar spine fusion by local gene therapy with a cDNA encoding a novel osteoinductive protein (LMP-1) (Abstract).*
Boden et al., Endocrinology. 1998 pp. 5125-5134. LMP-1, a LIM-domain protein, mediates BMP-6 effects on bone formation.*
Scott D. Boden et al., "LMP-1, A LIM-Domain Protein, Mediates BMP-6 Effects on Bone Formation", *Endo.* 139:5125-5138 (1998).
Akihito Minamide et al., "Mechanism of Bone Formation with Gene Transfer of the cDNA Encoding for the Intracellular Protein LMP-1", *J. Bone and Joint Surgery*, 85:1030-1039 (2003).

Hak-Sun Kim et al., "Overcoming the Immune Response to Permit Ex Vivo Gene Therapy for Spine Fusion With Human Type 5 Adenoviral Delivery of the LIM Mineralization Protein-1 cDNA", *Spine*, 28:219-226 (2003).
Mantula Viggeswarapu et al., "Adenoviral Delivery of LIM Mineralization Protein-1 Induces New-Bone Formation in Vitro and in Vivo", *J. of Bone and Joint Surgery*, 83:364-376 (2001).
Liu et al., BMP-6 Induces a Novel LIM Protein Involved in Bone Mineralization and Osteocalcin Secretion, *Journal of Bone and Mineral Research*, vol. 12: 49 (Aug. 1997).
Shawlot et al., Requirement for Lim1 in head-organizer function, *Nature*, vol. 374: 425-30 (1995).
DeRobertis, Dismantling the organizer, *Nature*, vol. 374: 407-08 (1995).
Agarwala et al., Specific Binding of Parathyroid Hormone to Living Osteoclasts, *Journal of Bone and Mineral Research*, vol. 7(5): 531-39 (1992).
Alden et al., Bone morphogenetic protein gene therapy for the induction of spinal arthrodesis, *Neurosurgical Focus* 4(2):12, (1998). [Electronic publication].
Alper, Boning Up: Newly Isolated Proteins Heal Bad Breaks, *Science*, vol. 263: 324-25 (1994).
Alwine et al., Detection of specific RNAs or specific fragments of DNA by fractionation in gels and transfer to diazobenzyloxymethy paper, *Methods Enzymol.*, vol. 68: 220-42 (1979).
Aslam et al., Contributions of Distal and Proximal Promoter Elements to Glucocorticoid Regulation of Osteocalcin Gene Transcription, *Molecular Endocrinology*, vol. 9(6): 679-90 (1995).
Ausubel et al., Quantitation of rare DNAs by the polymerase chain reaction, *Current Protocols in Molecular Biology*, chapter 15.31.1-8, (1990).
Badylak et al., Directed Connective Tissue Remodelling Upon a Biological Collagen Substrate, *J. Cell. Biochem.*, Suppl. 16F: 124 (Abstract CE027) (1992).
Bandara et al., Gene Transfer to Synoviocytes: Prospects for Gene Tratment of Arthritis, *DNA and Cell Biology*, vol. 11(3): 227-31 (1992).
Baumgartner et al., Constitutive expression of phVEGF-165 after intramuscular gene transfer promotes collateral vessel development in patients with critical limb ischemia, *Circulation*, vol. 97(12): 1114-23 (1991).
Beck et al., TGF-$\beta_1$ Induces Bone Closure of Skull Defects, *Journal of Bone and Mineral Research*, vol. 6(11): 1257-65 (1991).
Benvenisty et al., Direct introduction of genes into rats and expression of the genes, *Proc. Natl. Acad. Sci. USA*, vol. 83: 9551-55 (1986).
Bertuzzi et al., Molecular Cloning, Structure, and Chromosomal Localization of the Mouse LIM/Homeobox Gene L$hx$5, *Genomics*, vol. 36: 234-39 (1996).
Boden et al., Biologic Factors Affecting Spinal Fusion and Bone Regeneration, *SPINE*, vol. 20(24S): 102S-12S (1995).
Boden et al., Differential Effects and Glucocorticoid Potentiation of Bone Morphogenetic Protein Action During Rat Osteoblast Differentiation in Vitro, *Endocrinology*, vol. 137(8): 3401-07 (1996).
Boden et al., Estrogen Receptor mRNA Expression in Callus During Fracture Healing in the Rat, *Calcif. Tissue Int*, vol. 45: 324-25 (1989).
Boden et al., Gene Expression During Posterolateral Lumbar Spine Fusion: Effect of BMP-2, *Orthopaedic Research Society*, p. 1044 (1998).
Boden et al., Glucocorticoid-Induced Differentiation of Fetal Rat Calvarial Osteoblasts Is Mediated by Bone Morphogenetic Protein-6, *Endocrinology*, vol. 138(7): 2820-828 (1997).
Bonadio et al., Transgenic mouse model of the mild dominant form of osteogenesis imperfecta, *Proc. Natl. Acad. Sci. USA*, vol. 87: 7145-149 (1990).
Bonnarens et al., Production of a Standard Closed Fracture in Laboratory Animal Bone, *Journal of Orthopaedic Research*, vol. 2: 97-101 (1984).
Capecchi, Function of Homeobox Genes in Skeletal Development, *Annals New York Academy of Sciences*, vol. 785: 34-37 (1996).

Carrington et al., Accumulation, Localization, and Compartmentation of Transforming Growth Factor β During Endochondral Bone Development, *The Journal of Cell Biology*, vol. 107: 1969-975 (1988).

Centrella et al., Opposing Effects by Glucocorticoid and Bone Morphogenetic Protein-2 in Fetal Rat Bone Cell Cultures, *Journal of Cellular Biochemistry*, vol. 67: 528-40 (1997).

Centrella et al., Skeletal tissue and transforming growth factor β, *The FASEB Journal*, vol. 2: 3066-73 (1988).

Chen et al., Bone Morphogenetic Protein-2b Stimulation of Growth and Osteogenic Phenotypes in Rat Osteoblast-like Cell: Comparison with TGF-$\beta_1$, *Journal of Bone and Mineral Research*, vol. 6(12): 1387-93 (1991).

Chen et al., Osteoblastic Cell Lines Derived from a Transgenic Mouse Containing the Osteocalcin Promoter Driving SV40 T-Antigen, *Molecular and Cellular Differentiation*, vol. 3(3): 193-212 (1995).

Cholin et al., Expession of Recombinant Human Glutathione Reductase in Eukaryotic Cells after DNA-Mediated Gene Transfer, *Biochemical Medicine and Metabolic Biology*, vol. 49: 108-13 (1993).

Conner et al., Detection of sickle cell $B^S$-globin allele by dybridization with synthetic oligonucleotides, *Proc. Natl. Acad. Sci. USA*, vol. 80(1): 278-82 (1983).

Davidson et al., A model system for in vivo gene transfer into the central nervous using an adenoviral vector, *Nature Genetics*, vol. 3: 219-23 (1993).

Dawid et al., LIM domains: multiple roles as adapters and functional modifiers in protein interactions, *Trends Genet.*, 14(4): 156-62 (1998).

Dawid et al., LIM domain proteins, *C.R. Acad. Sci. Paris*, vol. 318: 295-306 (1995).

Durick et al., Mitogenic Signaling by Ret/ptc2 Requires Association with Enigma via a LIM Domain*, *The Journal of Biological Chemistry*, vol. 271(22): 12691-94 (1996).

Edelman et al., c-myc in Vasculoproliferative Disease, *Circulation Research*, vol. 76(2): 176-82 (1995).

England et al., An Immunological Study of Band 3, The Anion Transport Protein of the Human Red Blood Cell Membrane, *Biochima et Biophysica Acta.*, vol. 623(1): 171-82 (1980).

Evans et al., Possible Orthopaedic Applications of Gene Therapy, *The Journal of Bone and Joint Surgery, Inc.*, vol. 7(&): 1103-1114 (1995).

Falcone et al., Macrophage and Foam Cell Release of Matrix-bound Growth Factors, *The Journal of Biological Chemistry*, vol. 268(16): 11951-58 (1993).

Flaumenhaft et al., Role of the Latent TGF-β Binding Protein in the Activation of Latent TGF-β by Co-Cultures of Endothelial and Smooth Muscle Cells, *The Journal of Cell Biology*, vol. 120(4): 995-1002 (1993).

Fung et al., Characterization of a Human Cardiac Gene Which Encodes for a LIM Domain Protein and is Developmentally Expressed in Myocardial Development, *J. Mol Cell Cardiol*, vol. 28: 1203-10 (1996).

Gill, The enigma of LIM domains, *Structure*, vol. 3(12): 1285-89 (1995).

Graham et al., A New Technique for the Assay of Infectivity of Human Adenovirus 5 DNA, *Virology*, vol. 52(2): 456-67 (1973).

Gunsakaran et al., Mineralized Collagen as a Substitute for Autograft Bone That Can Deliver Bone Morphogenic Protein, *Nineteenth Annual Meeting of the Society for Biomaterials*, vol. XVI: 253 (1993).

Gunsakaran et al., Role of Mineralized Collagen as an Osteoconductive Biomaterial, *Nineteenth Annual Meeting of the Society for Biomaterials*, vol. XVI: 161 (1993).

Hair et al., Tissue Factor Expression in Human Leukemic Cells, *Leukemia Research*, vol. 20(1): 1-11 (1996).

Hoffmann et al., Bone Tissue-Specific Transcription of the Osteocalcin Gene: Role of an Activator Osteoblast-Specific Complex and Suppressor Hox Proteins That Bind the OC Box, *Journal of Cellular Biochemistry*, vol. 61: 310-24 (1996).

Hogan, Bone morphogenetic proteins: multifunctional regulators of vertebrate development, *Genes Dev.*, vol. 10(13): 1580-94 (1996).

Holliger et al., Morphology of the Lumbar Intertransverse Process Fusion Mass in the Rabbit Model: A Comparison Between Two Bone Graft Materials-rhBMP-2 and Autograft, *Journal of Spinal Disorders*, vol. 9(2): 125-28 (1996).

Horowitz et al., Functional and Molecular Changes in Colony Stimulating Factor Secretion by Osteoblasts, *Connective Tissue Research*, vol. 20: 159-68 (1989).

Hu et al., rHox: A Homeobox Gene Expressed in Osteoblastic Cells, *Journal of Cellular Biochemistry*, vol. 59: 486-97 (1995).

Huggins et al., Experiments on the Theory of Osteogenesis the Influence of Local Calcium Deposits on Ossification; The Osteogenic Stimulus of Epithelium, *Archives of Surgery*, vol. 32(6): 915-931 (1936).

Indolfi et al., Inhibition of cellular *ras* prevents smooth muscle cell proliferation after vascular injury in vivo, *Nature Medicine*, vol. i(6): 541-45 (1995).

Izumi et al., Transforming Growth Factor $\beta_1$ Stimulates Type II Collagen Expression in Cultured Periosteum-Derived Cells, *Journal of Bone and Mineral Research.* vol. 7(1): 115-21 (1992).

Jingushi et al., Acidic Fibroblast Growth Factor (aFGF) Injection Stimulates Cartilage Enlargement and Inhibits Cartilage Gene Expression in Rat Fracture Healing, *Journal of Orthopaedic Research*, vol. 8: 364-71 (1990).

Jingushi et al., Genetic Expression of Extracellular Matrix Proteins Correlates with Histologic Changes During Fracture Repair, *Journal of Bone and Mineral Research*, vol. 7(9): 1045-55 (1992).

Joyce et al., Role of Growth Factors in Fracture Healing, *Clinical and Experimental Approaches to Dermal and Epidermal Repair: Normal and Chronic Wounds*, pp: 391-416 (1991).

Joyce et al., Transforming Growth Factor-β and the Initiation of Chondrogenesis and Osteogenesis in the Rat Femur, *The Journal of Cell Biology*, vol. 110: 2195-2207 (1990).

Kaneda et al., Increased Expression of DNA Cointroduced with Nuclear Protein in Adult Rat Liver, *Science*, vol. 243: 375-78 (1989).

Karlsson et al., Gene transfer and bone marrow transplantation with special reference to Gaucher's disease, *Bone Marrow Transplantation*, vol. 11(1): 124-27 (1993).

Kawaja et al., Employment of Fibroblasts for Gene Transfer: Applications for Grafting Into the Central Nervous System, *Genetic Engineering*, vol. 13: 205-20 (1991).

Kawa-Uchi et al., Fibroblast growth factor enhances expression of TGFβ-stimulated-clone-22 gene in osteoblast-like cells, *Endocrine*, vol. 3: 833-37 (1995).

Khouri et al., Tissue Transformation Into Bone In Vivo a Potential Practical Application, *JAMA*, vol. 266(14): 1953-55 (1991).

Kimura et al., Isolation and Characterization of Temperature-Sensitive Mutants of Simian Virus 40, *Virology*, vol. 49: 394-403 (1972).

Kinglsey, What do BMPs do in mammals? Clues from the mouse short-ear mutation, *Trends Genet.*, vol. 10(1): 16-21 (1994).

Kohler et al., Continuous cultures of fused cells secreting antibody of predefined specificity, *Nature*, vol. 256(5517): 495-97 (1975).

Kukita et al., Regulation of Osteoclastogenesis by Antisense Oligodeoxynucleotides Specific to Zinc Finger Nuclear Transcription Factors Egr-1 and WT1 in Rat Bone Marrow Culture System*, *Endocrinology*, vol. 138(10): 4384-89 (1997).

Kuroda et al., Protein-Protein Interaction of Zinc Finger LIM Domains with Protein Kinase C*, *The Journal of Biological Chemistry*, vol. 271(49): 31029-32 (1996).

Ladher et al., Xom: a *Xenopus* homeobox gene that mediates the early effects of BMP-4, *Development*, vol. 122:2385-94 (1996).

Ledley et al., Development of a Clinical Protocol for Hepatic Gene Transfer: Lessons Learned in Preclinical Studies, *Pediatric Research*, vol. 33(4): 313-20 (1993).

Ledley, Hepatic Gene Therapy: Present and Future, *Hepatology*, vol. 18(5): 1263-73 (1993).

Ledley et al., Pre-Clinical Asessment of In Vivo Gene Therapy for Methylmalonyl CoA Mutase Deficiency Using Asialoglycoprotein/Polylysine/DNA Complexes, *J. Cell. Biochem. Suppl.* 17E: 238 (Abstract SZ 314) (1993).

Ledley, Somatic Gene Therapy in Gastroenterology: Approaches and Applications, *Journal of Pediatric Gastroenterology and Nutrition*, vol. 14: 328-37 (1992).

Lian et al., Development of the Osteoblast Phenotype: Molecular Mechanisms Mediating Osteoblast Growth and Differentiation, *The Iowa Orthopaedic Journal*, vol. 15: 118-40 (1995).

Lian et al., The Osteocalcin Gene Promoter Provides a Molecular Blueprint for Regulatory Mechanisms Controlling Bone Tissue Formation: Role of Transcription Factors Involved In Development, *Connective Tissue Research*, vol. 35(1-4): 15-21 (1996).

Lukert et al., Clinical and Basic Aspects of Glucocorticoid Action in Bone, *Principles of Bone Biology*, pp. 533-548 (1996).

Luyten et al., Purification and Partial Amino Acid Sequence of Osteogenin, a Protein Initiating Bone Differentiation, *The Journal of Biological Chemistry*, vol. 264(23): 13377-80 (1989).

Majmudar et al., Bone Cell Culture in a Three-Dimensional Polymer Bead Stabilizes the Differentiated Phenotype and Provides Evidence That Osteoblastic Cells Synthesize Type III Collagen and Fibronectin, *Journal of Bone and Mineral Research*, vol. 6(8): 869-81 (1991).

Mannino et al., Liposome Mediated Gene Transfer, *Bio Techniques*, vol. 6(7): 682-90 (1988).

Miyazono et al., Retention of the Transforming Growth Factor-$\beta$1 Precursor in the Golgi Complex in a Latent Endoglycosidase H-sensitive Form, *The Journal of Biological Chemistry*, vol. 267(8): 5668-675 (1992).

Mo et al., Specific and redundant functions of *Gli2* and *Gli3* zinc finger genes in skeletal patterning and development, *Development*, vol. 124: 113-23 (1997).

Nanes et al., Interferon-$\gamma$ Inhibits 1,25-Dihydroxyvitamin $D_3$-Stimulated Synthesis of Bone GLA Protein in Rat Osteosarcoma Cells by a Pretranslational Mechanism, *Endocrinology*, vol. 127(2): 588-94 (1990).

Nicolau et al., In vivo expression of rat insulin after intravenous administration of the liposome-entrapped gene for rat insulin 1, *Proc. Natl. Acad. Sci. USA*, vol. 80: 1068-92 (1993).

O'Malley, Jr. et al., DNA-and Viral-Mediated Gene Transfer in Follicular Cells: Progress Toward Gene Therapy of the Thyroid, *The Laryngoscope*, vol. 103(10): 1084-92 (1993).

O'Malley, Jr. et al., Somatic Gene Therapy, *Arch. Of Otolaryngol. Head and Neck Surg.*, vol. 119: 1100-07 (1993).

O'Malley, Jr. et al., Somatic Gene Therapy in Otolaryngology-Head and Neck Surgery, *Arch. Of Otolaryngol. Head and Neck Surg.*, vol. 119: 1191-97 (1993).

Paralkar et al., Identification and characterization of cellular binding proteins (receptors) for recombinant human bone morphogenetic protein 2B, an initiator of bone differentiation cascade, *Proc. Natl. Acad. Sci. USA*, vol. 88: 3397-3401 (1991).

Pereira et al., Genomic organization of the sequences coding for fibrillin, the defective gene product in Marfan syndrome, *Human Molecular Genetics*, vol. 2(7): 961-68 (1993).

Potter et al., Enhancer-dependent expression of human $_K$ immunoglobulin genes introduced into mouse pre-B lymphocytes by electroporation, *Proc. Natl. Acad. Sci. USA*, vol. 81: 7161-65 (1984).

Roessler et al., Adenoviral-mediated Gene Transfer to Rabbit Synovium In Vivo, *J. Clinical Investigation*, vol. 92: 1085-92 (1993).

Rosen et al., The BMP proteins in bone formation and repair, *Trends in Genetics*, vol. 8(3): 97-102 (1992).

Ryoo et al., Stage-Specific Expression of Dix-5 during Oseoblast Differentiation: Involvement in Regulation of Osteocalcin Gene Expression, *Molecular Endocrinology*, vol. 11(11): 1681-94 (1997).

Sampath et al., In vitro transformation of mesenchymal cells derived from embryonic muscle into cartilage in response to extracellular matrix components of bone, *Proc. Natl. Acad. Sci. USA*, vol. 81: 3419-23 (1984).

Sampath et al., Dissociative extraction and reconstitution of extracellular matrix components involved in local bone differentiation, *Proc. Natl. Acad. Sci. USA*, vol. 78(12): 7599-603 (1981).

Sandri-Goldin et al., High-Frequency Transfer of Cloned Herpes Simplex Virus Type 1 Sequences to Mammalian Cells by Protoplast Fusion, *Molecular and Cellular Biology*, vol. 1(8): 743-52 (1981).

Sandusky, Jr. et al., Histologic Findings After In Vivo Placement of Small Intestine Submucosal Vascular Grafts and Saphenous Vein Grafts in the Carotid Artery in Dogs, *American Journal of Pathology*, vol. 140(2): 317-24 (1992).

Schimandle et al., Experimental Spinal Fusion With Recombinant Human Bone Morphogenetic Protein-2, *Spine*, vol. 20(12): 1326-37 (1995).

Seitz et al., Effect of Transforming Growth Factor $\beta$ on Parathyroid Hormone Receptor Binding and cAMP Formation in Rat Osteosarcoma Cells, *Journal of Bone and Mineral Research*, vol. 7(5): 541-6 (1992).

Selander-Sunnerhagen et al., How an Epidermal Growth Factor (EGF)-like Domain Binds Calcium High Resolution NMR Structure of the Calcium Form of the $NH_2$-Terminal EGF-Like Domain in Coagulation Factor X*, *The Journal of Biological Chemistry*, vol. 267(27): 19642-49 (1992).

Shimell et al., The *Drosophila* Dorsal-Ventral Patterning Gene *tolloid* Is Related to Human Bone Morphogenetic Protein 1, *Cell*, vol. 67: 469-81 (1991).

Sikes et al., In vivo and ex situ gene transfer to the thyroid for somatic gene therapy in animal models, *Am. J. Human Genetics*, 51(4): A227 (Abstract 894) (1992).

Simons et al., Antisense c-*myb* oligonucleotides inhibit intimal arterial smooth muscle cell accumulation in vivo, *Nature*, vol. 359: 67-70 (1992).

Sompayrac et al., Efficient infection of monkey cells with DNA of simian virus 40, *Proc. Natl. Acad. Sci. USA*, vol. 78(12): 7575-78 (1981).

Soriano et al., Retroviral Tranduction of Human Hepatocytes and Orthotopic Engraftment in SCID Mice After Hepatocellular Transplantation, *Transplantation Proceedings*, vol. 24(6): 3020-21 (1992).

Southern, Detection of Specific Sequences Among DNA Fragments Separated by Gel Electrophoresis, *J. Mol. Biol.*, vol. 98: 503-17 (1975.

Srivastava et al., Construction of a recombinant parvovirus B19: Adeno-associated virus 2 (AAV) DNA inverted terminal repeats are functional in an AAV-B19 hybrid virus, *Proc. Natl. Acad. Sci. USA*, vol. 86: 8078-82 (1989).

Steiner et al., The New Enzymology of Precursor Processing Endoproteases, *The Journal of Biological Chemistry*, vol. 267(33): 23435-38 (1992).

Stratford-Perricaudet et al., Widespread Long-term Gene Transfer to Mouse Skeletal Muscles and Heart, *The Journal of Clinical Investigation*, vol. 90: 626-30 (1992).

Subramaniam et al., Identification of a novel TGF-$\beta$-regulated gene encoding a putative zinc finger protein in human osteoblasts, *Nucleic Acids Research*, vol. 23(23): 4907-12 (1995).

Summer et al., Enhancement of Bone Ingrowth by Transforming Growth Factor-$\beta$, *The Journal of Bone and Joint Surgery*, vol. 77-A(8): 1135-47 (1995).

Takagi et al., $\delta$EF1, a zince finger and homeodomain transcription factor, is required for skeleton patterning in multiple lineages, *Development*, vol. 125: 21-31 (1998).

Timmer et al., Characterization of Wheat Germ Protein Synthesis Initiation Factor e1F-4C and Comparison of e1F-4C from Wheat Germ and Rabbit Reticulocytes, *The Journal of Biological Chemistry*, vol. 268(33): 24863-67 (1993).

Toriumi et al., Mandibular Reconstruction With a Recombinant Bone-Inducing Factor, *Arch. Of Otolaryngology-Head and Neck Surgery*, vol. 117: 1101-12 (1991).

Towbin et al., Electrophoretic transfer of proteins from polyacrylamide gels to nirocellulose sheets: Procedure and some applications, *Proc. Natl. Acad. Sci. USA*, vol. 76(9): 4350-54 (1979).

Ulmer et al., Heterologous Protection Against Influenza by Injection of DNA Encoding a Viral Protein, *Science*, vol. 259: 1745-49 (1993).

Urist et al., Bone Cell Differentiation and Growth Factors, *Science*, vol. 220: 680-86 (1983).

Urist, Bone: Formation by Autoinduction, *Science*, vol. 150: 893-99 (1965).

Wang et al., Recombinant human bone morphogenetic protein induces bone formation, *Proc. Natl. Acad. Sci. USA*, vol. 87: 2220-23 (1990).

Welsh et al., Specific Factors Are Required for Kinase-dependant Endocytosis of Insulin Receptors, *Molecular Biology of the Cell*, vol. 5: 539-47 (1994).

Wilson et al., Somatic Gene Transfer in the Development of an Animal Model for Primary Hyperparathyroidism, *Endocrinology*, vol. 130(5): 2947-54 (1992).

Wolff et al., Conditions Affecting Direct Gene Transfer into Rodent Muscle In Vivo, *Biotechniques*, vol. 11(4): 474-85 (1991).

Wozney et al., Novel Regulators of Bone Formation: Molecular Clones and Activities, *Science*, vol. 242: 1528-34 (1998).

Wu et al., A Protein That Interacts Specifically With the Endocytic Code of the Human Insulin Receptor, *Mor. Cell. Biol.*, 4S: 117a (Abstract 683) (1993).

Wu et al., LIM Domain Recognition of a Tyrosine-containing Tight Turn, *The Journal of Biological Chemistry*, vol. 269(40): 25085-90 (1994).

Wu et al., Receptor-mediated Gene Delivery and Expression In Vivo, *The Journal of Biological Chemistry*, vol. 263(29): 14621-24 (1988).

Wu et al., Specificity of LIM Domain Interactions with Receptor Tyrosine Kinases, *The Journal of Biological Chemistry*, vol. 271(27): 15934-41 (1996).

* cited by examiner

SEQUENCE LISTING

<160> NUMBER OF SEQ ID NOS: 51

<210> SEQ ID NO 1
<211> LENGTH: 457
<212> TYPE: PRT
<213> ORGANISM: Rattus norvegicus

<400> SEQUENCE: 1

Met Asp Ser Phe Lys Val Val Leu Glu Gly Pro Ala Pro Trp Gly Phe
 1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Ala Gln Ser Lys Pro Gln Lys Ala Leu Thr
                 85                  90                  95

Pro Pro Ala Asp Pro Pro Arg Tyr Thr Phe Ala Pro Ser Ala Ser Leu
            100                 105                 110

Asn Lys Thr Ala Arg Pro Phe Gly Ala Pro Pro Pro Thr Asp Ser Ala
        115                 120                 125

Leu Ser Gln Asn Gly Gln Leu Leu Arg Gln Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu Phe Met Lys Lys Ser Ser Gln
            180                 185                 190

Val Pro Arg Thr Glu Ala Pro Ala Pro Ala Ser Thr Ile Pro Gln Glu
        195                 200                 205

Ser Trp Pro Gly Pro Thr Thr Pro Ser Pro Thr Ser Arg Pro Pro Trp
    210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Asn Arg Thr Ser Ile Val Gln Ala Ala Ala Gly Gly Gly Thr Gly Gly

```
              260                 265                 270
Gly Ser Asn Asn Gly Lys Thr Pro Val Cys His Gln Cys His Lys Ile
            275                 280                 285
Ile Arg Gly Arg Tyr Leu Val Ala Leu Gly His Ala Tyr His Pro Glu
        290                 295                 300
Glu Phe Val Cys Ser Gln Cys Gly Lys Val Leu Glu Glu Gly Gly Phe
305                 310                 315                 320
Phe Glu Glu Lys Gly Ala Ile Phe Cys Pro Ser Cys Tyr Asp Val Arg
                325                 330                 335
Tyr Ala Pro Ser Cys Ala Lys Cys Lys Lys Ile Thr Gly Glu Ile
            340                 345                 350
Met His Ala Leu Lys Met Thr Trp His Val Pro Cys Phe Thr Cys Ala
        355                 360                 365
Ala Cys Lys Thr Pro Ile Arg Asn Arg Ala Phe Tyr Met Glu Glu Gly
    370                 375                 380
Ala Pro Tyr Cys Glu Arg Asp Tyr Glu Lys Met Phe Gly Thr Lys Cys
385                 390                 395                 400
Arg Gly Cys Asp Phe Lys Ile Asp Ala Gly Asp Arg Phe Leu Glu Ala
                405                 410                 415
Leu Gly Phe Ser Trp His Asp Thr Cys Phe Val Cys Ala Ile Cys Gln
            420                 425                 430
Ile Asn Leu Glu Gly Lys Thr Phe Tyr Ser Lys Asp Lys Pro Leu
        435                 440                 445
Cys Lys Ser His Ala Phe Ser His Val
    450                 455

<210> SEQ ID NO 2
<211> LENGTH: 1696
<212> TYPE: DNA
<213> ORGANISM: Rattus norvegicus

<400> SEQUENCE: 2
gcacgaggat cccagcgcgg ctcctggagg ccgccaggca gccgcccagc cgggcattca    60
ggagcaggta ccatggattc cttcaaggta gtgctggagg acctgcccc ttggggcttc   120
cgtctgcaag gggcaagga cttcaacgtg cccctctcca tctctcggct cactcctgga   180
ggcaaggccg cacaggccgg tgtggccgtg ggagactggg tactgagtat cgacggtgag   240
aacgccggaa gcctcacaca cattgaagcc cagaacaaga tccgtgcctg tggggagcgc   300
ctcagcctgg gtcttagcag agcccagcct gctcagagca aaccacagaa ggccctgacc   360
cctcccgccg acccccgag gtacactttt gcaccaagcg cctccctcaa caagacggcc   420
cggcccttcg ggcacccccc acctactgac agcgccctgt cgcagaatgg acagctgctc   480
agacagctgg tccctgatgc cagcaagcag cggctgatgg agaatactga agactggcgc   540
ccgcggccag ggacaggcca gtcccgttcc ttccgcatcc ttgctcacct cacgggcaca   600
gagttcatgc aagacccgga tgaggaattc atgaagaagt caagccaggt gcccaggaca   660
gaagccccag cccagcctc aaccataccc aggaatcct ggcctggccc caccacccc    720
agccccacca gccgcccacc ctgggccgta gatcctgcat ttgctgagcg ctatgcccca   780
gacaaaacca gcacagtgct gacccgacac agccagccag ccacacctac gcctctgcag   840
aaccgcacct ccatagttca ggctgcagct ggagggggca caggaggagg cagcaacaat   900
ggcaagacgc ctgtatgcca ccagtgccac aagatcatcc gcggccgata cctggtagca   960
ctgggccacg cgtaccatcc tgaggaattt gtgtgcagcc agtgtgggaa ggtcctggaa  1020
```

```
                                                              -continued gagggtggct tcttcgagga aagggagct atcttttgcc cctcctgcta tgatgtgcgc    1080
tatgcaccca gctgtgccaa atgcaagaag aagatcactg gagagatcat gcatgcgctg   1140
aagatgacct ggcatgttcc ctgcttcacc tgtgcagcct gcaaaacccc tatccgcaac   1200
agggctttct acatggagga gggggctccc tactgcgagc gagattacga aagatgtttt   1260
ggcacaaagt gtcgcggctg tgacttcaag atcgatgccg gggaccgttt cctggaagcc   1320
ctgggtttca gctggcatga tacgtgtttt gtttgcgcaa tatgtcaaat caacttggaa   1380
ggaaagacct tctactccaa gaaggacaag cccctgtgca agagccatgc cttttcccac   1440
gtatgagcac ctcctcacac tactgccacc ctactctgcc agaaggggtga taaaatgaga   1500 gagctctctc tccctcgacc tttctgggtg gggctggcag ccattgtcct agccttggct   1560
cctggccaga tcctggggct ccctcctcac agtccccttt cccacacttc ctccaccacc   1620
accaccgtca ctcacaggtg ctagcctcct agccccagtt cactctggtg tcacaataaa   1680
cctgtatgta gctgtg                                                  1696

<210> SEQ ID NO 3
<211> LENGTH: 260
<212> TYPE: DNA
<213> ORGANISM: Rattus norvegicus

<400> SEQUENCE: 3
ttctacatgg aggagggggc tccctactgc gagcgagatt acgagaagat gtttggcaca    60
aagtgtcgcg gctgtgactt caagatcgat gccggggacc gtttcctgga agccctgggt   120
ttcagctggc atgatacgtg ttttgtttgc gcaatatgtc aaatcaactt ggaaggaaag   180
accttctact ccaagaagga caagcccctg tgcaagagcc atgccttttc ccacgtatga   240
gcacctcctc acactactgc                                              260

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence:  PCR primer
      H-T.sub.11G

<400> SEQUENCE: 4 aagcttttttt tttttg                                                  16

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence:  PCR primer
      H-AP-10

<400> SEQUENCE: 5
aagcttggct atg                                                      13

<210> SEQ ID NO 6
<211> LENGTH: 223
<212> TYPE: DNA
<213> ORGANISM: Homo sapiens

<400> SEQUENCE: 6
atccttgctc acctcacggg caccgagttc atgcaagacc cggatgagga gcacctgaag    60
aaatcaagcc aggtgcccag gacagaagcc ccagccccag cctcatctac accccaggag   120
```

| | |
|---|---|
| ccctggcctg gccctaccgc ccccagccct accagccgcc cgccctgggc tgtggaccct | 180 |
| gcgtttgccg agcgctatgc cccagacaaa accagcacag tgc | 223 |

<210> SEQ ID NO 7
<211> LENGTH: 717
<212> TYPE: DNA
<213> ORGANISM: Homo sapiens

<400> SEQUENCE: 7

| | |
|---|---|
| atggattcct tcaaggtagt gctggagggg ccagcacctt ggggcttccg gctgcaaggg | 60 |
| ggcaaggact tcaatgtgcc cctctccatt tcccggctca ctcctggggg caaagcggcg | 120 |
| caggccggag tggccgtggg tgactgggtg ctgagcatcg atggcgagaa tgcgggtagc | 180 |
| ctcacacaca tcgaagctca gaacaagatc cgggcctgcg gggagcgcct cagcctgggc | 240 |
| ctcagcaggg cccagccggt tcagagcaaa ccgcagaagg cctccgcccc cgccgcggac | 300 |
| cctccgcggt acacctttgc acccagcgtc tccctcaaca gacggcccg gccctttggg | 360 |
| gcgccccgc ccgctgacag cgccccgcaa cagaatggac agccgctccg accgctggtc | 420 |
| ccagatgcca gcaagcagcg gctgatggag aacacagagg actggcggcc gcggccgggg | 480 |
| acaggccagt cgcgttcctt ccgcatcctt gcccacctca caggcaccga gttcatgcaa | 540 |
| gacccggatg aggagcacct gaagaaatca agccaggtgc ccaggacaga agccccagcc | 600 |
| ccagcctcat ctacaccca ggagccctgg cctggcccta ccgccccag ccctaccagc | 660 |
| cgcccgccct gggctgtgga ccctgcgttt gccgagcgct atgccccgga caaaacg | 717 |

<210> SEQ ID NO 8
<211> LENGTH: 1488
<212> TYPE: DNA
<213> ORGANISM: Homo sapiens

<400> SEQUENCE: 8

| | |
|---|---|
| atcgatggcg agaatgcggg tagcctcaca cacatcgaag ctcagaacaa gatccgggcc | 60 |
| tgcggggagc gcctcagcct gggcctcagc agggcccagc cggttcagag caaaccgcag | 120 |
| aaggcctccg cccccgccgc ggaccctccg cggtacacct ttgcacccag cgtctccctc | 180 |
| aacaagacgg cccggccctt tggggcgccc ccgccgctg acagcgcccc gcaacagaat | 240 |
| ggacagccgc tccgaccgct ggtcccagat gccagcaagc agcggctgat ggagaacaca | 300 |
| gaggactggc ggccgcggcc ggggacaggc cagtcgcgtt ccttccgcat ccttgcccac | 360 |
| ctcacaggca ccgagttcat gcaagacccg gatgaggagc acctgaagaa atcaagccag | 420 |
| gtgcccagga cagaagcccc agccccagcc tcatctacac cccaggagcc ctggcctggc | 480 |
| cctaccgccc ccagccctac cagccgcccg ccctgagctg tggaccctgc gtttgccgag | 540 |
| cgctatgccc cggacaaaac gagcacagtg ctgacccggc acagccagcc ggccacgccc | 600 |
| acgccgctgc agagccgcac ctccattgtg caggcagctg ccggaggggt gccaggaggg | 660 |
| ggcagcaaca acggcaagac tcccgtgtgt caccagtgcc acaaggtcat ccggggccgc | 720 |
| tacctggtgg cgttgggcca cgcgtaccac ccggaggagt ttgtgtgtag ccagtgtggg | 780 |
| aaggtcctgg aagagggtgg cttctttgag gagaagggcg ccatcttctg cccaccatgc | 840 |
| tatgacgtgc gctatgcacc cagctgtgcc aagtgcaaga agaagattac aggcgagatc | 900 |
| atgcacgccc tgaagatgac ctggcacgtg cactgcttta cctgtgctgc ctgcaagacg | 960 |
| cccatccgga cagggccttt ctacatggag gagggcgtgc cctattgcga gcagactat | 1020 |
| gagaagatgt ttggcacgaa atgccatggc tgtgacttca gatcgacgc tggggaccgc | 1080 |

```
ttcctggagg ccctgggctt cagctggcat gacacctgct tcgtctgtgc gatatgtcag    1140
atcaacctgg aaggaaagac cttctactcc aagaaggaca ggcctctctg caagagccat    1200
gccttctctc atgtgtgagc cccttctgcc cacagctgcc gcggtggccc ctagcctgag    1260
gggcctggag tcgtggccct gcatttctgg gtagggctgg caatggttgc cttaaccctg    1320
gctcctggcc cgagcctggg ctcccgggcc cctgcccacc caccttatcc tcccacccca    1380
ctccctccac caccacagca caccggtgct ggccacacca gccccctttc acctccagtg    1440
ccacaataaa cctgtaccca gctgaattcc aaaaaatcca aaaaaaa                  1488

<210> SEQ ID NO 9
<211> LENGTH: 1644
<212> TYPE: DNA
<213> ORGANISM: Homo sapiens

<400> SEQUENCE: 9
atggattcct tcaaggtagt gctggagggg ccagcacctt ggggcttccg gctgcaaggg      60
ggcaaggact tcaatgtgcc cctctccatt tcccggctca ctcctggggg caaagcggcg     120
caggccggag tggccgtggg tgactgggtg ctgagcatcg atggcgagaa tgcgggtagc     180
ctcacacaca tcgaagctca gaacaagatc cgggcctgcg gggagcgcct cagcctgggc     240
ctcagcaggg cccagccggt tcagagcaaa ccgcagaagg cctccgcccc cgccgcggac     300
cctccgcggt acacctttgc acccagcgtc tccctcaaca agacggcccg gccctttggg     360
gcgcccccgc ccgctgacag cgccccgcaa cagaatggac agccgctccg accgctggtc     420
ccagatgcca gcaagcagcg gctgatggag aacacagagg actggcggcc gcggccgggg     480
acaggccagt cgcgttcctt ccgcatcctt gcccacctca caggcaccga gttcatgcaa     540
gacccggatg aggagcacct gaagaaatca agccaggtgc ccaggacaga agccccagcc     600
ccagcctcat ctacacccca ggagccctgg cctggcccta ccgccccccag ccctaccagc     660 cgcccgccct gggctgtgga ccctgcgttt gccgagcgct atgccccgga caaaacgagc     720
acagtgctga cccggcacag ccagccggcc acgcccacgc cgctgcagag ccgcacctcc     780
attgtgcagg cagctgccgg aggggtgcca ggagggggca gcaacaacgg caagactccc     840
gtgtgtcacc agtgccacaa ggtcatccgg ggccgctacc tggtggcgtt gggccacgcg     900
taccacccgg aggagtttgt gtgtagccag tgtgggaagg tcctggaaga gggtggcttc     960
tttgaggaga agggcgccat cttctgccca ccatgctatg acgtgcgcta tgcacccagc    1020
tgtgccaagt gcaagaagaa gattacaggc gagatcatgc acgccctgaa gatgacctgg    1080
cacgtgcact gctttacctg tgctgcctgc aagacgccca tccggaacag ggccttctac    1140
atggaggagg gcgtgcccta ttgcgagcga gactatgaga gatgtttggg cacgaaatgc    1200
catggctgtg acttcaagat cgacgctggg gaccgcttcc tggaggccct gggcttcagc    1260
tggcatgaca cctgcttcgt ctgtgcgata tgtcagatca acctggaagg aaagaccttc    1320
tactccaaga aggacaggcc tctctgcaag agccatgcct tctctcatgt gtgagcccct    1380
tctgcccaca gctgccgcgg tggccccctag cctgagggc ctggagtcgt ggccctgcat    1440
ttctgggtag ggctggcaat ggttgcctta accctggctc ctggcccgag cctgggctcc    1500 cgggccctg cccacccacc ttatcctccc accccactcc ctccaccacc acagcacacc    1560
ggtgctggcc acaccagccc cctttcacct ccagtgccac aataaacctg tacccagctg    1620
aattccaaaa aatccaaaaa aaaa                                          1644

<210> SEQ ID NO 10
```

<211> LENGTH: 457
<212> TYPE: PRT
<213> ORGANISM: Homo sapiens

<400> SEQUENCE: 10

```
Met Asp Ser Phe Lys Val Val Leu Glu Gly Pro Ala Pro Trp Gly Phe
 1               5                  10                  15

Arg Leu Gln Gly Gly Lys Asp Phe Asn Val Pro Leu Ser Ile Ser Arg
                20                  25                  30

Leu Thr Pro Gly Gly Lys Ala Ala Gln Ala Gly Val Ala Val Gly Asp
            35                  40                  45

Trp Val Leu Ser Ile Asp Gly Glu Asn Ala Gly Ser Leu Thr His Ile
 50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
            115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro Trp
    210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Ser Arg Thr Ser Ile Val Gln Ala Ala Ala Gly Gly Val Pro Gly Gly
            260                 265                 270

Gly Ser Asn Asn Gly Lys Thr Pro Val Cys His Gln Cys His Lys Val
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Ile Thr Gly Glu Ile
            340                 345                 350

Met His Ala Leu Lys Met Thr Trp His Val His Cys Phe Thr Cys Ala
        355                 360                 365

Ala Cys Lys Thr Pro Ile Arg Asn Arg Ala Phe Tyr Met Glu Glu Gly
    370                 375                 380

Val Pro Tyr Cys Glu Arg Asp Tyr Glu Lys Met Phe Gly Thr Lys Cys
385                 390                 395                 400
```

```
His Gly Cys Asp Phe Lys Ile Asp Ala Gly Asp Arg Phe Leu Glu Ala
            405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Arg Pro Leu
            435                 440                 445

Cys Lys Ser His Ala Phe Ser His Val
            450                 455

<210> SEQ ID NO 11
<211> LENGTH: 22
<212> TYPE: DNA
<213> ORGANISM: Rattus norvegicus

<400> SEQUENCE: 11
gccagggttt tcccagtcac ga                                            22

<210> SEQ ID NO 12
<211> LENGTH: 22
<212> TYPE: DNA
<213> ORGANISM: Rattus norvegicus

<400> SEQUENCE: 12
gccagggttt tcccagtcac ga                                            22

<210> SEQ ID NO 13
<211> LENGTH: 22
<212> TYPE: DNA
<213> ORGANISM: Homo sapiens

<400> SEQUENCE: 13
tcttagcaga gcccagcctg ct                                            22

<210> SEQ ID NO 14
<211> LENGTH: 22
<212> TYPE: DNA
<213> ORGANISM: Homo sapiens

<400> SEQUENCE: 14
gcatgaactc tgtgcccgtg ag                                            22

<210> SEQ ID NO 15
<211> LENGTH: 20
<212> TYPE: DNA
<213> ORGANISM: Rattus norvegicus

<400> SEQUENCE: 15
atccttgctc acctcacggg                                               20

<210> SEQ ID NO 16
<211> LENGTH: 22
<212> TYPE: DNA
<213> ORGANISM: Rattus norvegicus

<400> SEQUENCE: 16
gcactgtgct ggttttgtct gg                                            22

<210> SEQ ID NO 17
<211> LENGTH: 23
<212> TYPE: DNA
<213> ORGANISM: Homo sapiens

<400> SEQUENCE: 17
```

```
catggattcc ttcaaggtag tgc                                               23

<210> SEQ ID NO 18
<211> LENGTH: 20
<212> TYPE: DNA
<213> ORGANISM: Homo sapiens

<400> SEQUENCE: 18
gttttgtctg gggcagagcg                                                   20

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: adaptor
      for Marathon RACE reactions

<400> SEQUENCE: 19
ctaatacgac tcactatagg gctcgagcgg ccgcccgggc aggt                        44

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: PCR primer
      specific for Marathon RACE adaptor

<400> SEQUENCE: 20
ccatcctaat acgactcact atagggc                                           27

<210> SEQ ID NO 21
<211> LENGTH: 765
<212> TYPE: DNA
<213> ORGANISM: Homo sapiens

<400> SEQUENCE: 21
ccgttgtttg taaaacgacg cagagcagcg ccctggccgg gccaagcagg agccggcatc        60
atggattcct tcaaggtagt gctggagggg ccagcacctt ggggcttccg gctgcaaggg       120
ggcaaggact tcaatgtgcc ctcctccatt tcccggctca cctctggggg caaggccgtg       180
caggccggag tggccgtaag tgactgggtg ctgagcatcg atggcgagaa tgcgggtagc       240
ctcacacaca tcgaagctca gaacaagatc cgggcctgcg gggagcgcct cagcctgggc       300
ctcaacaggg cccagccggt tcagaacaaa ccgcaaaagg cctccgcccc cgccgcggac       360
cctccgcggt acacctttgc accaagcgtc tccctcaaca agacggcccg gcccttgggg       420
gcgcccccgc ccgctgacag cgccccgcag cagaatggac agccgctccg accgctggtc       480
ccagatgcca gcaagcagcg gctgatggag aacacagagg actggcggcc gcggccgggg       540
acaggccagt gccgttcctt tcgcatcctt gctcaccttc aggcaccgag gttcatgcaa       600
gacccggatg aggagcacct gaagaaatca agccaggtgc ccaggacaga agccccagcc       660
ccagcctcat ctacacccca ggagccctgg cctggcccta ccgccccag ccctaccagc        720
cgcccgccct gggctgtgga ccctgcgttt gccgagcgct atgcc                       765

<210> SEQ ID NO 22
<211> LENGTH: 1689
<212> TYPE: DNA
<213> ORGANISM: Homo sapiens

<400> SEQUENCE: 22
```

-continued

```
cgacgcagag cagcgccctg gccgggccaa gcaggagccg gcatcatgga ttccttcaag     60
gtagtgctgg aggggccagc accttggggc ttccggctgc aaggggggcaa ggacttcaat   120
gtgcccctct ccatttcccg gctcactcct gggggcaaag cggcgcaggc cggagtggcc    180
gtgggtgact gggtgctgag catcgatggc gagaatgcgg gtagcctcac acacatcgaa    240
gctcagaaca agatccgggc ctgcggggag cgcctcagcc tgggcctcag cagggcccag    300
ccggttcaga gcaaaccgca gaaggcctcc gcccccgccg cggaccctcc gcggtacacc    360
tttgcaccca gcgtctccct caacaagacg gcccggccct tggggcgcc ccgcccgct     420
gacagcgccc cgcaacagaa tggacagccg ctccgaccgc tggtcccaga tgccagcaag   480
cagcggctga tggagaacac agaggactgg cggccgcggc cggggacagg ccagtcgcgt   540
tccttccgca tccttgccca cctcacaggc accgagttca tgcaagaccc ggatgaggag    600
cacctgaaga aatcaagcca ggtgcccagg acagaagccc cagccccagc ctcatctaca    660
ccccaggagc cctggcctgg ccctaccgcc ccagcccta ccagccgccc gccctgggct    720
gtggaccctg cgtttgccga gcgctatgcc ccggacaaaa cgagcacagt gctgacccgg   780
cacagccagc cggccacgcc cacgccgctg cagagccgca cctccattgt gcaggcagct   840
gccggagggg tgccaggagg gggcagcaac aacggcaaga ctcccgtgtg tcaccagtgc  900
cacaaggtca tccggggccg ctacctggtg gcgttgggcc acgcgtacca cccggaggag   960
tttgtgtgta gccagtgtgg gaaggtcctg aagagggtg gcttctttga ggagaagggc  1020
gccatcttct gcccaccatg ctatgacgtg cgctatgcac ccagctgtgc caagtgcaag  1080
aagaagatta caggcgagat catgcacgcc ctgaagatga cctggcacgt gcactgcttt   1140
acctgtgctg cctgcaagac gcccatccgg aacagggcct tctacatgga ggagggcgtg  1200
ccctattgcg agcgagacta tgagaagatg tttggcacga aatgccatgg ctgtgacttc  1260
aagatcgacg ctggggaccg cttcctggag gccctgggct tcagctggca tgacacctgc  1320
ttcgtctgtg cgatatgtca gatcaacctg gaaggaaaga ccttctactc caagaaggac  1380
aggcctctct gcaagagcca tgccttctct catgtgtgag ccccttctgc ccacagctgc  1440
cgcggtggcc cctagcctga ggggcctgga gtcgtggccc tgcatttctg ggtagggctg   1500
gcaatggttg ccttaaccct ggctcctggc ccgagcctgg gctcccgggc ccctgcccac  1560
ccaccttatc ctcccacccc actccctcca ccaccacagc acaccggtgc tggccacacc   1620
agccccttt cacctccagt gccacaataa acctgtaccc agctgaattc caaaaaatcc    1680
aaaaaaaaa                                                            1689
```

<210> SEQ ID NO 23
<211> LENGTH: 22
<212> TYPE: DNA
<213> ORGANISM: Homo sapiens

<400> SEQUENCE: 23

```
gcactgtgct cgttttgtcc gg                                              22
```

<210> SEQ ID NO 24
<211> LENGTH: 21
<212> TYPE: DNA
<213> ORGANISM: Homo sapiens

<400> SEQUENCE: 24

```
tccttgctca cctcacgggc a                                               21
```

-continued

```
<210> SEQ ID NO 25
<211> LENGTH: 30
<212> TYPE: DNA
<213> ORGANISM: Homo sapiens

<400> SEQUENCE: 25
tcctcatccg ggtcttgcat gaactcggtg                                       30

<210> SEQ ID NO 26
<211> LENGTH: 28
<212> TYPE: DNA
<213> ORGANISM: Homo sapiens

<400> SEQUENCE: 26
gcccccgccc gctgacagcg ccccgcaa                                         28

<210> SEQ ID NO 27
<211> LENGTH: 24
<212> TYPE: DNA
<213> ORGANISM: Homo sapiens

<400> SEQUENCE: 27
tccttgctca cctcacgggc accg                                             24

<210> SEQ ID NO 28
<211> LENGTH: 22
<212> TYPE: DNA
<213> ORGANISM: Homo sapiens

<400> SEQUENCE: 28
gtaatacgac tcactatagg gc                                               22

<210> SEQ ID NO 29
<211> LENGTH: 23
<212> TYPE: DNA
<213> ORGANISM: Rattus norvegicus

<400> SEQUENCE: 29
gcggctgatg gagaatactg aag                                              23

<210> SEQ ID NO 30
<211> LENGTH: 23
<212> TYPE: DNA
<213> ORGANISM: Rattus norvegicus

<400> SEQUENCE: 30
atcttgtggc actggtggca tac                                              23

<210> SEQ ID NO 31
<211> LENGTH: 22
<212> TYPE: DNA
<213> ORGANISM: Rattus norvegicus

<400> SEQUENCE: 31
tgtgtcgggt cagcactgtg ct                                               22

<210> SEQ ID NO 32
<211> LENGTH: 1620
<212> TYPE: DNA
<213> ORGANISM: Homo sapiens

<400> SEQUENCE: 32
atggattcct tcaaggtagt gctggagggg ccagcaccct tggggcttcc gctgcaaggg      60
ggcaaggact tcaatgtgcc cctctccatt tcccggctca ctcctggggg caaagcggcg     120
```

```
caggccggag tggccgtggg tgactgggtg ctgagcatcg atggcgagaa tgcgggtagc      180
ctcacacaca tcgaagctca gaacaagatc cgggcctgcg gggagcgcct cagcctgggc      240
ctcagcaggg cccagccggt tcagagcaaa ccgcagaagg cctccgcccc cgccgcggac      300
cctccgcggt acacctttgc acccagcgtc tccctcaaca agacggcccg gcccctttggg     360 gcgccccgc  ccgctgacag cgccccgcaa cagaatggac agccgctccg accgctggtc      420
ccagatgcca gcaagcagcg gctgatggag aacacagagg actggcggcc gcggccgggg      480
acaggccagt cgcgttcctt ccgcatcctt gcccacctca caggcaccga gttcatgcaa      540
gacccggatg aggagcacct gaagaaatca agccaggtgc ccaggacaga agccccagcc      600
ccagcctcat ctacacccca ggagccctgg cctggcccta ccgccccag  ccctaccagc      660 cgcccgccct gagctgtgga ccctgcgttt gccgagcgct atgccccgga caaaacgagc      720
acagtgctga cccggcacag ccagccggcc acgcccacgc cgctgcagag ccgcacctcc      780
attgtgcagg cagctgccgg aggggtgcca ggaggggggca gcaacaacgg caagactccc     840
gtgtgtcacc agtgccacaa ggtcatccgg ggccgctacc tggtggcgtt gggccacgcg      900
taccacccgg aggagtttgt gtgtagccag tgtgggaagg tcctggaaga gggtggcttc      960
tttgaggaga agggcgccat cttctgccca ccatgctatg acgtgcgcta tgcacccagc     1020
tgtgccaagt gcaagaagaa gattacaggc gagatcatgc acgccctgaa gatgacctgg     1080
cacgtgcact gctttacctg tgctgcctgc aagacgccca tccggaacag ggccttctac     1140
atggaggagg cgtgcccta  ttgcgagcga gactatgaga gatgtttgg  cacgaaatgc     1200 catggctgtg acttcaagat cgacgctggg gaccgcttcc tggaggccct gggcttcagc     1260
tggcatgaca cctgcttcgt ctgtgcgata tgtcagatca acctggaagg aaagaccttc     1320
tactccaaga aggacaggcc tctctgcaag agccatgcct tctctcatgt gtgagcccct     1380
tctgcccaca gctgccgcgg tggccccctag cctgagggggc ctggagtcgt ggccctgcat     1440
ttctgggtag ggctggcaat ggttgcctta accctggctc ctggcccgag cctgggctcc     1500
cggggccctg cccacccacc ttatcctccc accccactcc ctccaccacc acagcacacc     1560
ggtgctggcc acaccagccc cctttcacct ccagtgccac aataaacctg tacccagctg     1620
```

<210> SEQ ID NO 33
<211> LENGTH: 1665
<212> TYPE: DNA
<213> ORGANISM: Homo sapiens

<400> SEQUENCE: 33

```
cgacgcagag cagcgccctg gccgggccaa gcaggagccg gcatcatgga ttccttcaag       60
gtagtgctgg aggggccagc accttggggc ttccggctgc aagggggcaa ggacttcaat      120
gtgcccctct ccatttcccg gctcactcct gggggcaaag cggcgcaggc cggagtggcc      180
gtgggtgact gggtgctgag catcgatggc gagaatgcgg gtagcctcac acacatcgaa      240
gctcagaaca agatccgggc ctgcggggag cgcctcagcc tgggcctcag cagggcccag      300
ccggttcaga gcaaaccgca gaaggcctcc gcccccgccg cggaccctcc gcggtacacc      360
tttgcaccca gcgtctccct caacaagacg gccggccct  tggggcgcc  ccgcccgct      420 gacagcgccc cgcaacagaa tggacagccg ctccgaccgc tggtcccaga tgccagcaag      480
cagcggctga tggagaacac agaggactgg cggccgcggc cggggacagg ccagtcgcgt      540
tccttccgca tccttgccca cctcacaggc accgagttca tgcaagaccc ggatgaggag      600
cacctgaaga aatcaagcca ggtgcccagg acagaagccc cagccccagc ctcatctaca      660
```

-continued

```
cccaggagc ctggcctgg ccctaccgcc cccagcccta ccagccgccc gccctgagct      720
gtggaccctg cgtttgccga gcgctatgcc ccggacaaaa cgagcacagt gctgacccgg    780
cacagccagc cggccacgcc cacgccgctg cagagccgca cctccattgt gcaggcagct    840
gccggagggg tgccaggagg gggcagcaac aacggcaaga ctcccgtgtg tcaccagtgc    900
cacaaggtca tccggggccg ctacctggtg gcgttgggcc acgcgtacca cccggaggag    960
tttgtgtgta gccagtgtgg gaaggtcctg gaagagggtg gcttctttga ggagaagggc   1020
gccatcttct gccccaccatg ctatgacgtg cgctatgcac ccagctgtgc caagtgcaag   1080
aagaagatta caggcgagat catgcacgcc ctgaagatga cctggcacgt gcactgcttt   1140
acctgtgctg cctgcaagac gcccatccgg aacagggcct tctacatgga ggagggcgtg   1200
ccctattgcg agcgagacta tgagaagatg tttggcacga aatgccatgg ctgtgacttc   1260
aagatcgacg ctggggaccg cttcctggag gccctgggct tcagctggca tgacacctgc   1320
ttcgtctgtg cgatatgtca gatcaacctg gaaggaaaga ccttctactc caagaaggac   1380
aggcctctct gcaagagcca tgccttctct catgtgtgag ccccttctgc ccacagctgc   1440
cgcggtggcc cctagcctga ggggcctgga gtcgtggccc tgcatttctg ggtagggctg   1500
gcaatggttg ccttaaccct ggctcctggc ccgagcctgg gctcccgggc cctgcccac    1560 ccaccttatc ctcccacccc actccctcca ccaccacagc acaccggtgc tggccacacc   1620 agccccttt cacctccagt gccacaataa acctgtaccc agctg                    1665
```

<210> SEQ ID NO 34
<211> LENGTH: 223
<212> TYPE: PRT
<213> ORGANISM: Homo sapiens

<400> SEQUENCE: 34

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
        115                 120                 125

Pro Gln Gln Asn Gly Gln Pro Leu Arg Pro Leu Val Pro Asp Ala Ser
    130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu

```
              195                 200                 205
Pro Trp Pro Gly Pro Thr Ala Pro Ser Pro Thr Ser Arg Pro Pro
    210                 215                 220

<210> SEQ ID NO 35
<211> LENGTH: 20
<212> TYPE: DNA
<213> ORGANISM: Homo sapiens

<400> SEQUENCE: 35
gagccggcat catggattcc                                               20

<210> SEQ ID NO 36
<211> LENGTH: 20
<212> TYPE: DNA
<213> ORGANISM: Homo sapiens

<400> SEQUENCE: 36
gctgcctgca caatggaggt                                               20

<210> SEQ ID NO 37
<211> LENGTH: 1456
<212> TYPE: DNA
<213> ORGANISM: Homo sapiens

<400> SEQUENCE: 37
cgacgcagag cagcgccctg ccgggccaa gcaggagccg gcatcatgga ttccttcaag     60
gtagtgctgg aggggccagc accttggggc ttccggctgc aagggggcaa ggacttcaat   120 gtgccctct  ccatttcccg gctcactcct gggggcaaag cggcgcaggc cggagtggcc   180
gtgggtgact gggtgctgag catcgatggc gagaatgcgg gtagcctcac acacatcgaa   240
gctcagaaca agatccgggc ctgcggggag cgcctcagcc tgggcctcag cagggcccag   300
ccggttcaga gcaaaccgca gaaggtgcag ccccctgaca acagccgct ccgaccgctg    360 gtcccagatg ccagcaagca gcggctgatg gagaacacag aggactggcg gccgcggccg   420
gggacaggcc agtcgcgttc cttccgcatc cttgcccacc tcacaggcac cgagttcatg   480
caagacccgg atgaggagca cctgaagaaa tcaagccagg tgcccaggac agaagcccca   540
gccccagcct catctacacc ccaggagccc tggcctggcc ctaccgcccc cagccctacc   600
agccgcccgc cctgggctgt ggaccctgcg tttgccgagc gctatgcccc ggacaaaacg   660
agcacagtgc tgacccggca cagccagccg gccacgccca cgcgctgca gagccgcacc   720 tccattgtgc aggcagctgc cggaggggtg ccaggagggg gcagcaacaa cggcaagact   780
cccgtgtgtc accagtgcca caaggtcatc cggggccgct acctggtggc gttgggccac   840
gcgtaccacc cggaggagtt tgtgtgtagc cagtgtggga aggtcctgga agagggtggc   900
ttctttgagg agaagggcgc catcttctgc ccaccatgct atgacgtgcg ctatgcaccc   960
agctgtgcca agtgcaagaa gaagattaca ggcgagatca tgcacgccct gaagatgacc  1020
tggcacgtgc actgctttac ctgtgctgcc tgcaagacgc catccggaa cagggccttc  1080 tacatggagg agggcgtgcc ctattgcgag cgagactatg agaagatgtt tggcacgaaa  1140
tgccatggct gtgacttcaa gatcgacgct ggggaccgct tcctggaggc cctgggcttc  1200
agctggcatg acacctgctt cgtctgtgcg atatgtcaga tcaacctgga aggaaagacc  1260
ttctactcca agaaggacag gcctctctgc aagagccatg ccttctctca tgtgtgagcc  1320
ccttctgccc acagctgccg cggtggcccc tagcctgagg ggcctggagt cgtggccctg  1380
catttctggg tagggctggc aatggttgcc ttaaccctgg ctcctggccc gagcctgggc  1440
```
tcccgggccc tgccca                                                                1456

<210> SEQ ID NO 38
<211> LENGTH: 423
<212> TYPE: PRT
<213> ORGANISM: Homo sapiens

<400> SEQUENCE: 38

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
             20                  25                  30

Leu Thr Pro Gly Gly Lys Ala Ala Gln Ala Gly Val Ala Val Gly Asp
         35                  40                  45

Trp Val Leu Ser Ile Asp Gly Glu Asn Ala Gly Ser Leu Thr His Ile
 50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Asn Lys Pro Gln Lys Val Gln Thr
             85                  90                  95

Pro Asp Lys Gln Pro Leu Arg Pro Leu Val Pro Asp Ala Ser Lys Gln
        100                 105                 110

Arg Leu Met Glu Asn Thr Glu Asp Trp Arg Pro Arg Pro Gly Thr Gly
        115                 120                 125

Gln Ser Arg Ser Phe Arg Ile Leu Ala His Leu Thr Gly Thr Glu Phe
    130                 135                 140

Met Gln Asp Pro Asp Glu Glu His Leu Lys Lys Ser Ser Gln Val Pro
145                 150                 155                 160

Arg Thr Glu Ala Pro Ala Pro Ala Ser Ser Thr Pro Gln Glu Pro Trp
                165                 170                 175

Pro Gly Pro Thr Ala Pro Ser Pro Thr Ser Arg Pro Pro Trp Ala Val
            180                 185                 190

Asp Pro Ala Phe Ala Glu Arg Tyr Ala Pro Asp Lys Thr Ser Thr Val
        195                 200                 205

Leu Thr Arg His Ser Gln Pro Ala Thr Pro Thr Pro Leu Gln Ser Arg
    210                 215                 220

Thr Ser Ile Val Gln Ala Ala Gly Gly Val Pro Gly Gly Gly Ser
225                 230                 235                 240

Asn Asn Gly Lys Thr Pro Val Cys His Gln Cys His Gln Val Ile Arg
                245                 250                 255

Ala Arg Tyr Leu Val Ala Leu Gly His Ala Tyr His Pro Glu Glu Phe
            260                 265                 270

Val Cys Ser Gln Cys Gly Lys Val Leu Glu Glu Gly Gly Phe Phe Glu
        275                 280                 285

Glu Lys Gly Ala Ile Phe Cys Pro Pro Cys Tyr Asp Val Arg Tyr Ala
    290                 295                 300

Pro Ser Cys Ala Lys Cys Lys Lys Ile Thr Gly Glu Ile Met His
305                 310                 315                 320

Ala Leu Lys Met Thr Trp His Val Leu Cys Phe Thr Cys Ala Ala Cys
                325                 330                 335

Lys Thr Pro Ile Arg Asn Arg Ala Phe Tyr Met Glu Glu Gly Val Pro
            340                 345                 350

Tyr Cys Glu Arg Asp Tyr Glu Lys Met Phe Gly Thr Lys Cys Gln Trp
        355                 360                 365
```

```
Cys Asp Phe Lys Ile Asp Ala Gly Asp Arg Phe Leu Glu Ala Leu Gly
        370                 375                 380

Phe Ser Trp His Asp Thr Cys Phe Val Cys Ala Ile Cys Gln Ile Asn
385                 390                 395                 400

Leu Glu Gly Lys Thr Phe Tyr Ser Lys Lys Asp Arg Pro Leu Cys Lys
                405                 410                 415

Ser His Ala Phe Ser His Val
                420

<210> SEQ ID NO 39
<211> LENGTH: 1575
<212> TYPE: DNA
<213> ORGANISM: Homo sapiens

<400> SEQUENCE: 39
cgacgcagag cagcgccctg gccgggccaa gcaggagccg gcatcatgga ttccttcaag       60
gtagtgctgg aggggccagc accttggggc ttccggctgc aagggggcaa ggacttcaat      120
gtgcccctct ccatttcccg gctcactcct gggggcaaag cggcgcaggc cggagtggcc      180
gtgggtgact gggtgctgag catcgatggc gagaatgcgg gtagcctcac acacatcgaa      240
gctcagaaca agatccgggc ctgcggggag cgcctcagcc tgggcctcag cagggcccag      300
ccggttcaga gcaaaccgca gaaggcctcc gcccccgccg cggaccctcc gcggtacacc      360
tttgcaccca gcgtctccct caacaagacg gcccggccct tggggcgcc ccgcccgct       420 gacagcgccc gcaacagaa tgggtgcaga ccctgacaa acagccgctc cgaccgctgg       480
tcccagatgc cagcaagcag cggctgatgg agaacacaga ggactggcgg ccgcggccgg      540
ggacaggcca gtcgcgttcc ttccgcatcc ttgcccacct cacaggcacc gagttcatgc      600
aagacccgga tgaggagcac ctgaagaaat caagccaggt gcccaggaca gaagcccag      660 ccccagcctc atctacaccc caggagccct ggcctggccc taccgccccc agccctacca      720
gccgcccgcc ctgggctgtg gaccctgcgt ttgccgagcg ctatgcccg gacaaaacga      780 gcacagtgct gacccggcac agccagccgg ccacgcccac gccgctgcag agccgcacct      840
ccattgtgca ggcagctgcc ggagggggtgc caggagggg cagcaacaac ggcaagactc      900
ccgtgtgtca ccagtgccac aaggtcatcc ggggccgcta cctggtggcg ttgggccacg      960
cgtaccaccc ggaggagttt gtgtgtagcc agtgtgggaa ggtcctggaa gagggtggct     1020
tctttgagga aagggcgcc atcttctgcc caccatgcta tgacgtgcgc tatgcaccca     1080
gctgtgccaa gtcaagaag aagattacag gcgagatcat gcacgccctg aagatgacct     1140
ggcacgtgca ctgctttacc tgtgctgcct gcaagacgcc catccggaac agggccttct     1200
acatggagga gggcgtgccc tattgcgagc gagactatga aagatgttt ggcacgaaat     1260 gccatggctg tgacttcaag atcgacgctg ggaccgctt cctggaggcc ctgggcttca     1320
gctggcatga cacctgcttc gtctgtgcga tatgtcagat caacctggaa ggaaagacct     1380
tctactccaa gaaggacagg cctctctgca agagccatgc cttctctcat gtgtgagccc     1440
cttctgccca cagctgccgc ggtggcccct agcctgaggg gcctggagtc gtggccctgc     1500
atttctgggt agggctggca atggttgcct taaccctggc tcctggcccg agcctgggct     1560
cccgggccct gccca                                                      1575

<210> SEQ ID NO 40
<211> LENGTH: 153
<212> TYPE: PRT
<213> ORGANISM: Homo sapiens
```

<400> SEQUENCE: 40

```
Met Asp Ser Phe Lys Val Val Leu Glu Gly Pro Ala Pro Trp Gly Phe
 1               5                  10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
        115                 120                 125

Pro Gln Gln Asn Gly Cys Arg Pro Leu Thr Asn Ser Arg Ser Asp Arg
    130                 135                 140

Trp Ser Gln Met Pro Ala Ser Ser Gly
145                 150
```

```
<210> SEQ ID NO 41
<211> LENGTH: 24740
<212> TYPE: DNA
<213> ORGANISM: Homo sapiens
<220> FEATURE:
<221> NAME/KEY: unsure
<222> LOCATION: 1..6
<223> OTHER INFORMATION: a or c or g or t
<220> FEATURE:
<221> NAME/KEY: unsure
<222> LOCATION: 8101
<223> OTHER INFORMATION: a or c or g or t
```

<400> SEQUENCE: 41

| | | | | | |
|---|---|---|---|---|---|
| nnnnnntgta | ttttatcata | ttttaaaaat | caaaaaacaa | aaggcagttg | aggttaggca | 60 |
| tggaggttcg | tgcctgtaat | cccagcactt | tgggaagccg | aagcacgtgg | atcacctgag | 120 |
| gtcaggagtt | cgagaccagc | ctgcccaata | tggtaaaacc | ctgtctctac | taaaaataca | 180 |
| aaaaattagc | caggcatggt | ggtgggcacc | tgtaatccca | gctacttggg | agactgaggc | 240 |
| aggagaatca | cttaaacccg | ggaggcgggc | tgggcgcggt | ggctcatgcc | tgtaatccca | 300 |
| gcactttggg | aggccgagac | aggcggatca | tgaggtcagg | agatcgagat | catcctggct | 360 |
| aacatggtga | aaccccatct | ctactaaaaa | tacaaaaaaa | attagccagg | cctggtggcg | 420 |
| ggcacctgta | gtcccagcta | cttgggaggc | tgaggcagga | gaatggcgtg | aacctgggag | 480 |
| gcggcgttgc | agtgagccaa | gatcgcgcca | ctgcactcca | gcctgggcga | caagagtgag | 540 |
| actccatctt | aaagaaaaaa | aacaaacccg | ggaggcggaa | attgcagtca | gccgagatct | 600 |
| cgccattgca | ctcaagtatg | ggtgacgag | caagactcca | tgtcaaaaaa | aaaggcagtt | 660 |
| gacaggagca | aggagcctgg | tgaggaagct | gtggcatttg | acccggctgt | gttgctatgg | 720 |
| gccagggtgg | tgctagtaga | ggagctgagt | gggaaagagc | acaggggaca | tgctgaaggc | 780 |
| ctgggtgtgg | ggatgaggca | gagattgggg | gcaccttgca | gggtcatagc | aggtggctgt | 840 |
| ggtgagatgg | aggaagacac | ctggggtact | gctctaggct | gtcagacata | cagaagctgg | 900 |
| cccagccaag | cccaggggct | gcaagggaca | tcctttgtg | tccccagtga | tctgcagctc | 960 |

```
tcagacaccc tcaagcacag tgcctcttgc ccagcccagc actctcagtg gggagccagg   1020
tgggagaaca ggctcggaag gggacctagg cttatgcagc gagccgggca aagctggaac   1080
tggagcccag gccctggat gccccctggc ttgtggagtt ctgggatact gaggggaggg    1140
gacagggcat gggagtgcgg tgctctcacc tttgacttga actcattccc caggggacag   1200 ggaggcctc ctcaggatcc acagatgccc agtctcccaa gaggggcctg gtccccatgg    1260
aggaaaactc catctactcc tcctggcagg aaggtaagtt ggaggacgtg caagggcagc   1320
ctcagccccc cacacccagg gctgggtctt tttgggactg acggagctgt cctggccacc   1380
tgccacagtg ggcgagtttc ccgtggtggt gcagaggact gaggccgcca cccgctgcca   1440
gctgaagggg ccggccctgc tggtgctggg cccagacgcc atccagctga gggaggccaa   1500
ggcacccagg ccctctacag ctggccctac cacttcctgc gcaagttcgg ctccgacaag   1560
gtgaggtgca ggggtgggaa agggtgaggg gctgacagcc tggaccctcc tgctaatccc   1620
cacccgtgtg ccctgtgccc agggcgtgtt ctcctttgag gccggccgtc gctgccactc   1680
gggtgagggc ctctttgcct tcagcacccc ctgtgcccct gacctgtgca gggctgtggc   1740
cggggccatc gccgccagcg ggagcggctg ccagagctga ccaggcccca gccctgcccc   1800
ctgccacggg ccacctctct gccctccctg gacaccccg gagagcttcg ggagatgcca    1860
ccaggacctg agccacccac gtccaggaaa atgcacctgg ccgagcccgg accccagagc   1920
ctgccgctac tgctaggccc ggagcccaac gatctggcgt ccgggctcta cgcttcagtg   1980
tgcaagcgtg ccagtgggcc cccaggcaat gagcacctct atgagaacct gtgtgtgctg   2040
gaggccagcc ccacgctgca cggtggggaa cctgagccgc acgagggccc cggcagccgc   2100
agccccacaa ccagtcccat ctaccacaac ggccaggact tgagctggcc cggcccggcc   2160
aacgacagta ccctggaggc ccagtaccgg cggctgctgg agctggatca ggtggagggc   2220
acaggccgcc ctgaccctca ggcaggtttc aaggccaagc tggtgaccct gctgagtcgt   2280
gagcggagga agggcccagc cccttgtgac cggccctgaa cgcccagcag agtggtggcc   2340 agagggaga ggtgctcccc ctgggacagg agggtgggct ggtgggcaaa cattgggccc    2400
atgcagacac acgcctgtgt ccaccctggc ctgcaggaac aaggcaggcc gcctgtggag   2460
gacctcagcc ctgccctgcc ctcctcatga atagtgtgca gactcacaga taataaagct   2520
cagagcagct cccggcaggg gcactcacgg cacacgcccc tgcccacgtt cattgcggcc   2580
aacacaagca ccctgtgccg gttccagggg cacaggtgac ctgggcctta cctgccaccc   2640
gtgggctcaa acccactgca gcagacagac gggatgaaaa tcattaggac tccatgttgc   2700
tctgcacggc cgagtgacac gaagaggcag gcggagggag ctgtgaggct tacttgtcag   2760
actcaggaag gagcaacatg agggcccaac tggagacccg gaggcccgag ctgggaggag   2820
gcagtggggg cggggtgcag gtggaaggga tttcagagac accctcgtcc aaaacacttg   2880
ttccctgcta aaactccaac aatttgcaga tacttctggg aaccccaggc gtcagtctcc   2940
tcatctgtaa aggagagaga accgatgacg tatcaggcat aatccttgat gagagtttgc   3000
tgcgtgccta ctcagtgcca ggcgctgggg acacagccg tgttcaggac agccttggtc    3060
ctgttctccg ggagccgaca ttccaggggg agagaagttt cctgaagact ccatgctgc    3120 gttcctcct ctgctcctgc tcctggcgcc atcctaggag ccagccatgc acgcaagcgt    3180
catgcctcca gggctctgac tgcccagccc ctcaccgcaa ctccacctca gctgcacaca   3240
cccttggcac atcctgaacc tcattttcat gacggacaca caattttgc tctctcctgt    3300 ccaagcctca tcctctggcc gccacctcct tccagctcac ttcctttagt gcggccagta   3360
```

```
ccgcccctgc ctaggcatgt cgacctgcag ggaccctttt ctggctcttc gaggcctctg    3420
cccaccatcc cctctttgtt ctccatagtc ccttccccct gttctctctc gtttcatctt    3480
actggtctgg caaagtcccc ggccttgggc gagccagacc tcctcagtgc ctgcacacag    3540
ctgcccacag ccagagaaat ccatttaagc agactgcctg catccttctt aacagtgcaa    3600
ggcaggcact ccctgccaca agagaccctg ttccctagta gggcagcttt tctcctcccc    3660
agaacctcct gtctatcccc acccaatgtc tcctcacagg catattgggg aaacaggtca    3720
ggctctccca ccgtatctgc aagtgtactg gcatccatct gtcttcttcc taccccctaca    3780 gtagaaacag tgtctgtccc cagctgtgct ctgatcccgg ctcctttcac ctcagagctt    3840
ggaaaattga gctgtcccca ctctctcctg cgcccattca tcctaccagc agcttttcca    3900
gccacacgca aacatgctct gtaatttcac attttaaacc ttcccttgac ctcacattcc    3960
tcttcggcca cctctgtttc tctgttcctc ttcacagcaa aaactgttca aaagagttgt    4020
tgattacttt catttccact ttctcacccc cattctctcc tcaattaact ctccttcatc    4080
cccatgatgc cattatgtgg cttttattag agtcaccaac cttattctcc aaaacaaaag    4140
caacaaggac tttgacttct cagcagcact cagctctggt tcttgaaaca ccccgttac    4200 ttgctattcc tcctacctca taacaatctc cttcccagcc tctactgctg ccttctctga    4260
gttcttccca gggtcctagg ctcagatgta gtgtagctca accctgctac acaaagaatc    4320
tcctgaaagc ctgtaaaaat gtccatgcat gttctgtgag tgatctacca agaaaataaa    4380
aaattttaaa aatcaaatgc ccatgcctgg cccacacgc aggggctctg atttcatcag    4440
tctggtaggt gggttctggg catccacgct cactggattt ccggatgatt gtagtatgca    4500
gcctaggctg ggaaccactg gcctcagcaa gccagtcatt ctccaggtgt cacagaccct    4560
ctaggtgcta atgaccccga aggtctgtct tcagtgcaca cctcccctg agctccagat    4620 ttaggaatcc cactgcacac gagacatctg gatgtggaaa agacatctcc agatcccatg    4680
ggtgaaaggg ggttggggga atggagactc gtgttcttcc aggatgtgtg tggacacaga    4740
atgcaaagcc tggagggatg ctagagccat agggaggaag atttcggctc acttattcat    4800
gcaagcactt cctgatgggt aaggtcttag agcaagctga ggccaagagg cgggcagtcg    4860
aggtgctgct gcaggcaccc ccactcccta cagtggcaag cccaagccca gcccttggca    4920
gctcaaatcc caggacacgc tgaaggtcac ccagagagtc aggggcatgg ctagaaccag    4980
aacccaggac tctggggacc cagcatggca tcctttcctt cattacaaat ctgagctgct    5040
ttgtttccta gggatttctg tgatattcca aggggactgt gggaaagaaa gtccttggaa    5100
accaccagga cgctagaggc ctggcctgga gcctcaggag tctcggccac cagagggcgc    5160
tgggtccttg tccaggtcca gttgctacgc aggggctgcc tgtgctggga ggctccccag    5220
gggacacaga ccagagcctt gcaccagccc aaggaatggg agcctggggt cctctctgct    5280
ggaggactgc caggaccccc aggctgccgc ctcttccttt gctcatttgc tgtttcactt    5340
tgtcaatcct tcctttcttc gtgtgttcat tcacatccac tgtgtgctgg ccctgggaa    5400 atgttagata agacacatta gctgtgtgtc ttcattgtcc taacaaagaa cacaccctgg    5460
aaagagcacc gcagagagtc cccattcccc catctccctc cacacatgga atctggagat    5520
gccttttcca catccagatg tctctggtgc tgtgggattc ttaaataaac aaacatttca    5580
tacagaatgt gagatgatgg agatgctatg gggaaaagta aagcagaggg agggcctagt    5640
gtgtgatgcg ggtgaggcat ccagggattg ctgtttcagc tgtgatcagg aaaggccctg    5700
ggaggaggcc acatctgagc agagacctaa ataaagttgg aaacctgttg ctgagatatc    5760
```

```
tggagaagtg tttcaagggc cgggcaccgg gcatggtggc tcacgcctgt aatcccagca    5820
ctttgggagg ccaaggcagg tggatcgctg gaggtcagga gtttgagagc agcctgacca    5880
acatggagaa accccatctc tactaaacat ataaaaatta tccgggcatg gtggttcatg    5940
cctgtagtcc cagctactcg ggaggttgag gcaggagaat cacttgaacg tgggaggcag    6000
aggttgcagc aagccgagat cacaccactg cactccagcc tggatgacag agcgagactc    6060
cgtctcaaaa aaaaaaaga aagaaaaaa gaaaaaaaa gaaaagtgtt tcaagcaggg    6120
gaactggcaa gtggagaggc cctgaggcag aaatatgctt ggcctgctgg aggaaatgtg    6180
agtgaggagg tcagggtggc tggagtggag ggagcgagtg gtaggagtca gacccagttt    6240
attcatattc tgtaggtctt aaggacttca gtttattt gagtgcaata tgagcccact    6300
ggaatgctaa aagctgagag tgacatggtg ctgtgattct ggctttaaaa atatcacttt    6360
ggctgcttcg tgaagactct ggaaggggca agggtgaaag cagggatgcc cgttaggaga    6420
ccgttacagg ggcgcaggca caaaatggca gtggctggga caatggtggc agcagcggtt    6480
agatgtgaac atgttgaagg tggaatttgc agaatctggg ggaggacaga agagaaagga    6540
taacttcatc gttctgctg aaccagttgg ataaatgttg gtggcacttc ttgaagtgag    6600
gaaggagtta ggaaggtggg aaaggcacaa gtttgaattg ggccatgatg gtctgagata    6660
cctagtacag tggttcccca accttttgg cagaagggac cgctttcatg gaagacaatt    6720
tttccacaga ctggggtgg ggtggggatg gtttcagggt ggttcgagtg cagtacattt    6780
atcattagac tctttttttt tttttttt tgagatagag tctcgctctg tcacccacac    6840
tggagtgcag tggagccatc ttggctcact acaacctctg ctgcccaggt tcaagtcatt    6900
ctcctgcctc agcctctcaa gtagctggga ttataggcat atgcgccacc acgcccagct    6960 aattttgta tttttagtag agacgggtt tcaccatatt ggccaggatg gtctcgaact    7020
cctgacctca gtgatcctc cccgcctca acctcccaaa gtgctgggt tacaggcgtg    7080 aaccactgca cccggcccat ttatcattag attctcataa ggaatgagca acctagatcc    7140
ctcgcatgca cagttcacaa tagggttcac gctcctatgg gagtctaatg ctgccgctgc    7200
actcagcttc tctggcttgc cgctgctcac cttctgctgt gcagcccagt tcctaacagg    7260
ccacaaacgg ggagttgggg acccctgatc tagtaaacat ctaggcaggg ttttggataa    7320
tggagttaga gttcctgggg agaggtcagg ctggccatga acatgggat gcctttgcat    7380 ataggtggtg ttgaaagcca caggacagta cggggtctca gggggtgagc ataaagagag    7440
gcgacatcag atggccaagg ccagaggcag aggaggatgg gaaggagggg ccagtggggc    7500 aggggaagc tgtgaagcca gggaaaaagg gtgtttcgcg gaaaaggatc aacctggacc    7560
agtgctgccc ctaggcaggg caggatgaaa cttaaccacc acggattcca tggcccatg    7620 gcctccaggc cacaggggac cttgagaaga gagatctcag gggacgggtg cggacaagag    7680
cccgcctggc atggcttcaa gagataactg aaggaaagca agtggagacg cgataaacag    7740
acaactccct ggaggaattt tactctcgag aggagaatta aagggtagta gctggagagg    7800
gatgtggggt caagagaagg tctttaacga cgagaactct cacggcggtt tgtgcagaac    7860
agggtgggtg tgatgactgt ggatggagag gggagaactg cagcgactct gtcctaggag    7920
gaggtgatgg gccgggacca ccaagcgagt ggagggtgga cgccccttcc ctcacccga    7980 cacccgcatg tgctcagtgt ccgtgccgcc ggccctagtg cctgggctga acgcggggcc    8040
gggactctga ggacgcctcc caggcgcgca gtccgtctgg ccaaggtgga gcggacggc    8100 ngcttccgac ggtgcgcggg tcggctcggg gttgcaggga catccggcgt ccgctcctgc    8160
```

```
cctgttttcc tgccttcgca gagcgttgcg caactctagc tttaaacgcc cctgtccccc    8220
tcaacttgtc tcccccagcc cctctgattt acagattctg cagtcccccga gggttgcgcc    8280
tacgataccg acactcgcgg cagcctgcga ggcgagtatg atcgtcccat ttttcggagt    8340
agcaaactaa ggttcagaga ctactatgtc ccaggtcggt ctggtttgaa ggtccgcttt    8400
cctctccctc cgccagcggg cggtgcgagg gactgggcga ggcagcgctt ccctaaggag    8460
gcgacccgca gccccggccc cctcccgact ccgcccgtt gcagggcccg ggtcggcgag     8520
gcctctcagc tctaagcccg acgggacttg gtgattgggc aggacggaag agctgggtgg    8580
ggctttccac cagcggagaa agtctagtgg gcgtggtcgc gacagggcg tggcctggtg     8640
ccccgccccc gtccgcgcgc tcaaagtgga gggtggctgt gggggcgggg tcagaacact    8700
ggcggccgat cccaacgagg ctccctggag cccgacgcag agcagcgccc tggccgggcc    8760
aagcaggtat cgacgaccgc gcggggcgtc ttgggctgga ccaggcgggc gcccggggcc    8820
tgctgaggac cacaaagggc actggggtc gtggtccagg ctgtgcttcc tcccgctggc     8880
cctggcccct gcctccgccc ccgcccccgc cttcctgccg ctaagccggc tgcggcgggg    8940
ccgattggcg cctgccggct tcctgcgccg gggccagtct aatgcatggg gcccgggcgg    9000
gggactaagg ggaaactgag tcacgtcggt gtgggagcag ttctgtgtgg gaggcaccac    9060
cccccactgg gctcggggaa ggatcccct ccaagctatg cttgagggtc ccagccccca     9120
tctgtctcca caggggccgc accccactcc cgccttcccc ttcttcagca cccagggtc     9180
ccgcctggc tcccagcagc ctcgactggt cccggaatgg ctaggaggat ccgctgcagc     9240
cgcctccctc ccctcccctc ccctcccctc ccctcccctc ccctcccctc ccctcccctc    9300
ccctcgcgt cccaagcccc cgtgtgctcc ctccgctggc tctccgcaca gtgtcagctt     9360
acacgcctta tatagtccga gcaggctcca gccgcgccct gctgccggga cctggggcg     9420
ggggagagga gagccggccc ctgactcacc cggaccgccc gaggctccag gctggcttgg    9480
ggggaggccg cgccagttta gtccctcggc ccaccctgg ttgcaaagaa cctcaagcct     9540
ggattcaggc acccctcacc gttccagtcc caggggagg ggggctgctc ctgtctttcc     9600
aaagtgaggt ccgccagcca gcagcccagg ccagcctgac aaaatacctg cctcctatgg    9660
cttgggcgtg ctcaggggct gcccgtgcct gcctggcccc tgtccaaggc tggtatcctg    9720
agctggcccg gcctgcctgc ctgcccgccc accatgctgg ccactcacct tctcttctct    9780
cctctcagga gccggcatca tggattcctt caaagtagtg ctggaggggc cagcaccttg    9840
gggcttccgc ctgcaagggg gcaaggactt caatgtgccc ctctccattt cccgggtgag    9900
cctaggtttg gggagggggc tcccccagcg gtctttcggt gcttaggtct ccagagggtg    9960
atgggggag tcctaacagg agctggtcag gggccagcag gccaggagat gtctaggtcc    10020
ggagatgtag tggtacctgc ctgccacaag gactcccaat gaggtggata ctgggaggga   10080
gcacccaggc ttctccagcc ctgcactgta cccgatgctg ttctcccaag ctcctgtggc   10140
cacctctgag ggctggaggg aggctcattg tgcaggatgg gagcctaaca tttcaggagg   10200
tatctaaact tgaggtggca atgcttggag ccaggcccca gcaggacac tgtgactata    10260
ggatttcact tcagcctcac tgccgcccag ggaatagcaa tcctcatccc gttttttccag   10320
atgagagaag aactcatgga gaggtggcgg ggctcgctca tcgagtccat ggtgaagcag   10380
ggattggaat tgaggcacag catggcgtac attttttgtg ggtagaaggg gtctctcccc   10440
agcctatgta aggacccaca tccactgttc ccattcagga tgtggtggcc tttgacccca   10500
agcagaagtg taggacaggg ctccattcta ggggcttaac ttcagcttcc aagagcctgc   10560
```

```
cctggtgtgg gtggagctgg aggctggctc ctccctgtag caggggggatt gccttataag   10620 cccaagaatg cagccccacg ctgggatggc aacagtggc tgcggtctgc agagctgaaa    10680
agggctggcc taggcctggc cccctgaacc ccactggtgg gcctctcagc tggtcaccag    10740
gctgcagctc cagctgtatg gtccagttgt gagacacaac aaattgcctg cccagagtgg    10800
gtgaggccag cctgtcggct ggcatctctg actggcctgg gggtcaggag ggggtgggga    10860
cttcctgccc ctatatccgc ctgccccgag agacccaccc aggcgccggg tgggcaggca    10920
gctgttgtca ggaagcccaa ggcaagccca gcctggaggg gcccagaggg tcgtggcctg    10980
aggaggggct caagctggag tctgtctgta ggagctgggc gtggggtta gggtgggcag    11040 gccagcagtg ctcttctcag gggtcctttg atggcattct cctggaacct gccccgccag    11100
cagggtagta aggcagtggt tgccctatga cacacgtccc actacatagc cctcacacag    11160
ccctgaaacc tacctgacgt cctgctccct gggaaagtgc tggcccagtg tgtctgggga    11220
gcctgaacct cagtttcttc cctgatggag atgactttca gatatggcct gttgggggca    11280
ctccgggctc cagctccctg gtcagcatcc ctggcatgtg ggcgggggcca ctagctgatc    11340 ccagccctgg agttggacct gggcccacat gggtgggtga ggtgggcttt tctgagttag    11400
gccagccccc tcccctccc ctgaccccag aatggaggga ggtgggaggg gcaagggctg    11460
gctgtgggcc caggcctggg agatgaggta acgtctggga ctgggggggct gggctgctca    11520 ggctgactca ccccaccctc atgcagggtc cagccccctg gcttttccc tccttggttc    11580 ctctggcctt accctgcccc tggcttgagc ccctccctgc ctctctccag ccacccgccc    11640
agcgctgtct tctgctctcc tgctgccctc cccacgctct gaacacccct catcctctgt    11700
gcttcctgcc ctcctcactc tgggaaggga agccgtcccc gccccccacc ccctctccag    11760
gagccagcta gctgcacccc aagaccccca cctcgggctc agcccacagc tcccaggagc    11820
cagccctgtg ggcagggagt ggctgggcca ggtttccctt ctactgactc accatgacct    11880
tgagtaagtc acttcccctc tggggtgtca cttccccata cacagtataa ggggttgatt    11940
tagttggatt gaactaaagg tgagggagtg gctcagggtg tctccaggtg ggctgacccc    12000
tcagttgggc cccatgctc agcagaggtg gcccacagtg gtggagcctt agggtcagag    12060
acacttcctg gctctgcctc ttactagctg ggtgacttga ggcaagttgt ttaacctctc    12120
tgtgtacatt tgcaagtgca aaatgggtaa aatcccagat tactccacaa ggttgttgga    12180
agattcagtg tcaatatgta gcatagttgg tgctcaataa actgaagcaa gtcttcttat    12240
ttagcgagtg aggaagggc cgccgagctc tcttagcctt ctgacctcct acgcaagcaa    12300
gaggtcatgt tgagcccagc tcgccttttct tttcccagtg ctgtcaagct ctgtgcctgg    12360 ctgcctgcc ctctgacatc tctctgaaac ctcttgcctc ccctctccct gcctcagctc    12420
agtctgtgca ctgacccacc tgaggagcct cctggggcca ctggcagcct gggaccccccc    12480 agatcccccc cacccagtga aattgtcttc cagcactgcc tcacaaaagc ctacttgatg    12540
cagtgccagg cctcttgcca gatggctggg tggtccctta ggcttggacc cagtcaagct    12600
gccctgcctg tgttgctggg gctgggctag aggcctggaa ggggtttatc agggtcaccc    12660
tctcagggcc tgggagatac ccaatcccag acattaaaac tgccagtagc ccctctacct    12720
tcaaagccaa gtcctggtcc cttccctgg cattcaaagc catcgtaagt gaactctcac    12780
ccgctaggca gcacacgcca ttctcccttta ccgaggccca ccgcttcctc aaagtcattc    12840
ctgatggtct cagctcatgc tggtggcagc catttctccc agcctactgt ctctactcat    12900
tgccacagga accagggact cccagctcaa gagcctgaag gattggggtc agggaaatt    12960
```

```
ggcagtcgag ggcttgggag tgacagccat gtatggccta cgaagtccca gctgtcaact    13020
taggtcccat tcaggcagtg ttcacaggga accgggagat aacagggcct gttcctggct    13080
ctcaaagggt cccagcagac ccctatagat ggcccccgac agggtgctgg ggggtgagag    13140
gtccataaga gcccccggtg gtttcgggga ggaagctgcc ccctgcatgg gccagagggc    13200
atatctggta ggtggagtgg cctgggcagg aggccagcag gagcctcaaa aggcaatggt    13260
cctcctgaaa cacttgggct ttagcctgag cgtggctgtt tgtggacatc atagcaattt    13320
ctggactgtg ggggagggtg gtggcggtga atagataagc atcgtgactg gggaagctca    13380
ggtgagcacc acctgaggga gagggtctgg cagtgaataa ataagcagtg tgactgggaa    13440
attgtgaagc tcaggtgagc gccaccacct cctgggttgc tttagtgtcc agcagctgcc    13500
tagaactatg ttgaatgaag agctctctgg gttctggaag tgggacagct ttgggtgggg    13560
cagtgttacc accgtcagcc tggcttgggt ctgcagggtc cagggcctcg gtcactttgc    13620
ttctctctcc acagctcact cctggggcaa aagcggcgca ggccgagtg gccgtgggtg    13680 actgggtgct gagcatcgat ggcgagaatg cgggtagcct cacacacatc gaagctcaga    13740
acaagatccg ggcctgcggg gagcgcctca gcctgggcct cagcaggtat gcgggtggac    13800
atggatgggt gcgcccgcgc tggcagtggg gatccctgcg gccggcccg ctgtcacgct    13860 ttccttctcc tccagggccc agccggttca gagcaaaccg cagaaggtac gaggctggcc    13920
gggacatccg ggcggtgggc ggtgtgggct tggacggcca ggcctgctcg ccctcctggc    13980
acattctcgg tacccccaatc cctggccggg agtggagggc agaaaccgga gctaaggcgg    14040
gtctagggcc ctggagttga gccaggggct gctgcacggt cctggcacca cgcatgtccg    14100
cctgtctgtc cgcctgtctg tccgcctgct gcctcccgcc gccggcgctg cgtgctcgcc    14160
cgcactcggt cagccctcgg tcctgcgtgg actgagatcg ccactcccaa atgggcccct    14220
tgaaacctga gtcgtcctct ccccgtagcc tccaaataga tgtagggggt ggggtggggg    14280 tgggggctg gagctgccgc tgtcctctgc tgcaggcgcc ccacttccac ccaggcccc    14340 accttacccct gcccgcccgc cctgccggg tgtgtctctg cccaggcctc cgcccccgcc    14400
gcggaccctc cgcggtacac ctttgcaccc agcgtctccc tcaacaagac ggcccggcct    14460
ttgggcgccc ccgcccgctg acagcgcccc gcagcagaat gggtacgtcg ccccctgccc    14520
gcccgcgccc acgccatcag gcccactgtg gccccacgcc cgctgcccgc tgctgctcag    14580
tctgtgctgc gccccagccc ggcggaaccg tgcggcacgc ccctggcgg ccggggtggg    14640 gctgcaggca cagggcccct cccgaggctg tggcgccttg cagggcaccg cctggggagg    14700
ggtctctgaa tgacgccgcg ccccctgctg gcggctgggg gttgggttgt ggtgtcgggc    14760
cagctgagcc ccagacactc agtgccgcct tgtccccggc tgttctgacc cctccccgtc    14820
tttcttcctc tcctgtgtct gtcccttttgt ccctttatct gtctgtctgt cttatttcct    14880
tcacaggtgc agaccctga caagtcagtg agccccctc tgcctgtgcc tttcttcttc    14940
cttttggcac tctgggtggc ggcccctccc caccctggct gccctcctct ccacttcgcc    15000
ctcctgtcct ctcacctacc cgcccagcag ggctcctggc ctcaccctta cccactccct    15060
cccatcactg taacccaaac ccacatgcac caaatcctgg gaggggctgc cccaccgcc    15120 caccccagt gtgggttct gagccacacc ctccccacag acagccgctc cgaccgctgg    15180
tcccagatgc cagcaagcag cggctgatgg agaacacaga ggactggcgg ccgcggccgg    15240
ggacaggcca gtcgcgttcc ttccgcatcc ttgcccacct cacaggcacc gagttcagta    15300
agtgccagcc cagggcaggg ggtactttcc tcgcccccag cccaggcgtg atccctgacc    15360
```

```
ctgtgtcttt tttggtcaat gcctgcctct gctctctcag tgcaagaccc ggatgaggag    15420
cacctgaaga aatcaaggta cagggacggg caccagcccc tctcccacct cctgcctctt    15480
ccattccagc tactgccctg tgtctactcc tgaggctccc agctggggct ctcaattctc    15540
ccttccttcc ttccttcctt ccttccttcc ttccttcctt ccttccttcc ttccttcctt    15600
cccttcctcc ttccttcctt ctttcatttc ttccctccct ccttccttcc ctcctccctc    15660
cctgcctccc ttccatctct ccttccttcc acttcttcct ccctctctct ctgcccctca    15720
gggaaaagta tgtcctggag ctgcagagcc cacgctacac ccgcctccgg gactggcacc    15780
accagcgctc tgcccacgtg ctcaacgtgc agtcgtagcc cggccctctc cagccggctg    15840
ccctctctgc ctccctcttt ctgttcctcc tgcccagggc accccttag tgcctccagc    15900 ttctgcctac ctcaccccc ctttcgtgcc cctggcctga cctcctgct ggcctggccc    15960 tggccgccca cctgggttca tctgacactg ccttccctct ttgccctgtg gtactgctgt    16020
ctgccaggtc tgtgctgcct tgggcatgga ataaacattc tcagccctgc ttgctctgcc    16080
tgtcttctat ctttgtggac ctggtttgca tttggggtgt gggggtgttt cgtggttcgg    16140
actgtttggg ccctgccgtc cttgttttca gtgggagggg gtacctggca aaggggccct    16200
gccctgccat cacagatggc ttcctggcat gaggggagcc ccaggagctg cctcagaagc    16260
gggagccctg cctcgtctcc cagctagaga ccgcacacca gctaactgga cattgctagg    16320
agaagctgcc cttcccatcc ctaccccagt gggacctgga atccaactcg gcagtttcca    16380
cgcccccagt catctcccgt ggggccagca ggacccaggt tggggggtgg ggccatgtca    16440
ggaagctcag ccatgcaggg ccttgaatgg cagatcttgc agccaggtgc ccaggacaga    16500
agccccagcc ccagcctcat ctacacccca ggagccctgg cctggtgaga gggagtgggc    16560
tcgggcctgg gcaagggtgg gcagcctcca ggggcatggg ggtggtgggc ttctctcagc    16620
tgcctggggc tccaccccg tcctttgggg tccctgggca ccctttaga gtcactttcc    16680 ccggcaggcc ctaccgcccc cagccctacc agccgcccgc cctgggctgt ggaccctgcg    16740
tttgccgagc gctatgcccc ggacaaaacg agcacagtgc tgacccggca cagccagccg    16800
gccacgccca cgccgctgca gagccgcacc tccattgtgc aggcagctgc cggagggtg    16860 ccaggagggg gcagcaacaa cggcaagact cccgtgtgtc accagtgcca caaggtcatc    16920
cggtgggtgg cctgttcctg tccgaccctg gctttcccat cctgcagccc agccccacct    16980
gtctgcccac ctgtcttgcc tcagctgcga ctggggggaa taaggattca gttctcagct    17040
ggagtaggag tagggacctg ggctgggtcc tcccattctt aatcccacgc tacctacccc    17100
agcccaccca caacaactgc tagcagcatc tgccgtggcg aaatagccga agggccaacc    17160
ataggctgaa gctgcacccc tacctttgct gctctctggg caaagagggg cctgccccct    17220
cccagcgcgt ctgcccctcc ctcctgctct ctgtctccct ctgctctcag agcatacagg    17280
cctggagcca ctccctctgt gcactgcccc gtggggccaa gcagcatcaa acacccccca    17340
gcatcagcgt gccggattct agagccttcc taattcgcag gcctggcctg ctctcatctc    17400
tgtcagctct ttttttttt ttttgaaac agagtctcac tgtgttgccc acgttggcgt    17460
gcagtggcgc gatctcggct cactgcaacc tctgcctcct gggttcaaga gattctcctg    17520
cctcagcctc ctgagtagct gggattacag gcacccgcca ccatgcctgg ctaattttgt    17580
atttttagta gagacggggt tttaccatgt tggccaggct ggtctcaaac tcctcacctc    17640
aggtgatctc aggcctgcct tggcctccca aagtgctggg actacaggtg tgagccactg    17700
tgcccagccg actctatcag ctcttgccag gtagaacagg caggccagca ggacagggca    17760
```

```
gctccagggt tgcccaggg gcggctcagc ttttatgagg ctccagtcgt cagcccttcc    17820
tcccggggtc ctccctgctc taaagctgcc tctcctgtca ccagcagttc agtgtggcgg    17880
actggctctg taagcttcat ggctgccacg gtcacttccc aagcctgtct tctatcctat    17940
gtggaaaatg gggagaatga actgtccctc ccaaggcctc ctggtgggtg gtcagtcaac    18000 ctgaagggg ccaagacccc cacctctctg cgtgtgctcc ctctgaccgc tctcgcctcc    18060
ctgcaggggc cgctacctgg tggcgctggg ccacgcgtac cacccggagg agtttgtgtg    18120
tagccagtgt gggaaggtcc tggaagaggg tggcttcttt gaggagaagg gcgccatctt    18180
ctgcccacca tgctatgacg tgcgctatgc acccagctgt gccaagtgca agaagaagat    18240
tacaggcgtg agtagggctg gctggcgggg aggtggtccc aagcctgtca gtgggaacga    18300
gggctgctgg gaaacccaca gtccaggtct ctccccgagt gagcctccgg gtccttacca    18360
gcgtaataaa tgggctgctg tactggcctc accctgcatt agtcaggatg ctcttaacaa    18420
atgaccatgt tcctgctcag aaaccgccca aggctgcaaa gagcaggagg accaagccag    18480
gagaagccct gggccctcct gactcccact ttgggctctc cctgccctgg tgaaatgaca    18540
gaacggccaa cttgacacgc tgaagctgct ctgtctcatg cgtcctcctc atttctggat    18600
ccagagccag ggctgccagg agtagccaga gagctctgtg tggtgatgtt catattagtg    18660
aggtttacct tgaccacgag cagtgggaaa ctcaaaataa tggtggctta tttctcatct    18720
aaaaacatcc cggggtgggt ggtctgggac tgatctggtg gacccaggct ccgccttgtt    18780
gcttgactgt tggcagcacc tgcttactta ccactcatgg tgcaagatga cacttcagcc    18840
tccgccaaaa tgctcacctt ccagccagca ggaagtcgga aggagaagaa aggggacaga    18900
gccccatggc gtccatcctt agaggatgct gccacctgaa cctctgcttt catcctgttg    18960
gtcagaaccc agtcacatga ccacacccag tggcaacgga ggctgggaaa tatagtcttt    19020
attttgggca cccatgtgtc cagcaaaact gggggttcca tcagtcggca agaacgggag    19080
agtggccgat gcagtggctg atgcttgtat cccagcactt tgggaggtcg aggtgggcag    19140
atcacctgag gtcaggagtt caagaccagc ctggccaata tggtgaaacc ctgtctctac    19200
taaaaataaa aaaattagct gggtgtgctg gcgcacctgt agtcccagct acttgggagg    19260
ctgaggcagg agaatcgctt gatcttgaga ggtggaggtt gcagtgagcc aagattgtgc    19320
cactgccttc cagcctggga gacagcaaaa aaaaaaaaa aaaaaaaaa aaaagggcc    19380 aggcacggtg gctcacacct gtaatcccag cactttggga ggccgagatg gcggatcac    19440 gaggtcagga gattgagacc atcctggcta acacggtgaa accccatctc tactaaaaat    19500
acaaaaaaat tggccgggca tggtggagta gtcccagcta ctcgggaggc tgaggcagga    19560
gaatggcgtg aacctgggag gcagagcttg cagtgagccg agatcgcgcc actgcactcc    19620
agcctgggca acagagcgag actcttgtct caaaaagaaa aaagaaaga gaaatctgcc    19680 tcccagcctt gggctcctgc cctaccagcc cacaccctg gtagagcctc ctctcccacc    19740
agctcaaagc ccaagttcct tcactgtgac cttgtctgct cctctaaaac aggcaacacc    19800
agacagtgag aagagccagc cagacatggg cagaaaacct atttctgtga tctactggct    19860
gtgtgagcag gggctagttg ctctctctgg gcctcactga agagaagggt ggcactatgc    19920
tagggccggc acggttgcaa ggtagatgta agatgggta caggtgttgt ggagggcaga    19980
aatgcaccat ccgaaggcta catgtccccc acacttatgt cttgcttggc ccacactgtt    20040 tcatttaaa atcagtagca aacaattaa aaaatcagaa gatttgcctg catgatgcag    20100
tggctcatgc ctgtaatccc agcactttgg gaggccaagg tgggaggatt gcttgagccc    20160
```

```
aggagttcaa gaccagcatg ggcaccatag caagacccct gtttctacaa aaaaaaaaaa   20220
attagaaaat tagccaagtg tggtggcatg cacctgtggt cccagctact tgggaggcag   20280
agggaaagtg agatctcctg ctttttattt ctttatgtat aatgataggg tcttgctctg   20340
ttgcccaggc tggagtgcag tggcatgatc actgctcact gcagccttga tctcctgggc   20400
tcagaggatc ctcccacctc agcctcccaa atagctagga ctagaggtgc ccaccagcat   20460
gctcagcaga ttttaaatc tttttgtaga gatgaggttt tgctatgttg cccaggctgg   20520
tctcgaactc ctggcctcga gcgatcctcc caccttggcc tcccaaagca ctgggattac   20580
agacgtgagc cactgcgccc agcagatttc tctttaacac ctagatttca gcctgagcca   20640
ggcaggcatt cctgaatgaa ccagtagtac tgctcccaga agaagaggtc ctcctccgtg   20700
tgacacagtc cccacttggc ccttgcaggg attggatctg ggatccctgg atttaaactc   20760
agggccatcc tcataacagc ctcacaaggc tgggattagc ttcccagttc acaagggaag   20820 aaaccagagac ttgagaaggt caaggtctgg ccagacccac acatcttgga ccctcatacc   20880
gcctcgaggc cccatgctgc cctctgcctg ctccagatgt gaatactgct ggccctggct   20940
ggccccggct ggccccgagg gtcctaggga tgaacagccc agcccaggga gagctcagcc   21000
ccttgtgcct ctgccccttc ccacctcctg cggaggccag tcgactcacc cacaaagggc   21060
caggcactgt ggggatagat cagctaacaa aacagttgat gcttcctgcc cttctgggcc   21120
ttacattttg gctggaagaa gaggggagag gcagactgta agcaataagc gcaataagta   21180
ggttgcctgg aagtaatgtt agatcacgtt acggaaaaca ggaaagagca gagcgacaag   21240
tgctggggtg cgtggtgcag ggaaggcagc tggctgctgc tggtgtggtc agagtgggcc   21300
ctcatggaga agactgcatt cgagcagaaa cttgaagggg gtgaggggtg agcctagaga   21360
tatctggggc agagcagtcc aggcagaggg gacagccggt gtcaagccca ggacaggagt   21420
gtgcctggtg tgccagtttc aggcaagagg ccagtgtgca gaggcaaggt gagaacgcaa   21480
gggagagcag tggcggagac gggtgggaac gaggtcagac ctgctggcct ccagcctctg   21540 catgggctt ggctcttgct gggagcaatg ggaagcagta cacagtttca tgcaggggga   21600
gaaggcctgt cttgggttgc aggggcacgc tgtggcagct gggatcagag agaggagctt   21660
gtaggccagt tgttatgtgg tcccacgggc cagatggcca tggcttacct cacttcaggg   21720
aggctgtgag aagcactcag aatctggatg tgccttgggg gtgggcccca ctggatttcc   21780
tggtggacct ggtgtggggt gtgagaggag ggtgtgtttg gctgcagcag acaggagaat   21840
ggagttgcca tccgcgtgat ggggatggct gtgggaggag aggtttgggg tgagggaatc   21900
aggaactgag tgctggacat ggcaagtctg aaggcgcagt ggtcgtccac tcagagacct   21960
tggagttgga gatggaggtg tgggagtcct gaacagttag atgtagtgtt taccgcgaga   22020
aggaacaggg cttgcggcca gccctcctgt gttcccgtga cccagggcag ggcaggaggg   22080
gcctgagcct gccgagtgac tgggacctcc ttccaggaga tcatgcacgc cctgaagatg   22140
acctggcacg tgcactgctt tacctgtgct gcctgcaaga cgcccatccg gaacagggcc   22200
ttctacatgg aggagggcgt gccctattgc gagcgaggta cccactggcc agtgagggtg   22260
aggagggatg gtgcatgggg caggcatgaa tccaggtcct ctttctctct gcccccattc   22320
tcagactatg agaagatgtt tggcacgaaa tgccatggct gtgacttcaa gatcgacgct   22380
ggggaccgct tcctggaggc cctgggcttc agctggcatg acacctgctt cgtctgtgcg   22440
gtgagagccc cgcccctcga actgagcccc aagcccaccg gccctctgtt cattccccag   22500
gagatgcagg agaagttggg aagggggcctc tcctgctgcc cccaacccca tgtgactggg   22560
```

```
cctttgctgt ccttagatat gtcagatcaa cctggaagga aagaccttct actccaagaa    22620
ggacaggcct ctctgcaaga gccatgcctt ctctcatgtg tgagcccctt ctgcccacag    22680
ctgccgcggt ggcccctagc ctgaggggcc tggagtcgtg ccctgcatt  tctgggtagg    22740
gctggcaatg gttgccttaa ccctggctcc tggcccgagc ctggggctcc ctgggccctg    22800
ccccacccac cttatcctcc caccccactc cctccaccac cacagcacac cgatgctggc    22860
cacaccagcc cccttcacc  tccagtgcca caataaacct gtacccagct gtgtcttgtg    22920
tgcccttccc ctgtgcatcc ggaggggcag aatttgaggc acgtggcagg gtggagagta    22980
agatggtttt cttgggctgg ccatctgggt ggtcctcgtg atgcagacat ggcgggctca    23040
tggttagtgg aggaggtaca ggcgagaccc catgtgccag gcccggtgcc cacagacatg    23100
aggggagcca ctggtctggc ctggcttgga ggttagagaa gggtagttag aagggtagt    23160
tagcatggtg gctcatgcct gtgatcccag cactttggaa ggccaaggtg ggcagatcgc    23220
ttgaggtcag gagttcgaga cctcatggcc aacacggtga aacagcgtct ctagtaaaaa    23280
tacaaaaatt agccgagtgt ggtggggcat gcctgtaatc ccagccactc aggaggctga    23340
ggcgggaaaa tcacttgaac ctgggaagtg gaggttgcag tgagctgaga tcacaccact    23400
gcgcgcgagc ctgggtggca gatggcagag cgagaccctg cttcaaaaaa aaaaaaaaaa    23460
aaaaaaaaaa gaagggtagt tgtagttggg ggtggatctg cagagatatg gtgtggaaaa    23520
cagcaatggc cacagcaaag tcctggaggg gccagctgcc gtccaaacag aagaaggcag    23580
ggctggagag ggtagcccct aggtcctggg aagccacgag tgccaggcag tagagctggg    23640
gctgtctctt gaggttaggg cagggcaagg cacagcagag tttgaaatag gtttgtgttg    23700
tattgcagaa aagaggcccc agaacactga gggagtgcag gagggaggct gggaggagga    23760
gttgcagcag ggcctagggg cgggggccag gcaagggagg ggcagagagt aatatggcag    23820
agatgggacc cagtggcagg tccgggggat gagggatgga gagaaggaca ggagcgttgc    23880
caggcatctg gcctatacca gacatgctca cgctgtctcc cgcgaacctc ctagcaacct    23940
tgcgccgttg tctgcaatca cttatttcat ttttctttt  ttaacttaa  ttttttttgt    24000
ttttaagaga caggatctcc ctaggttgcc cgggctggtt tcaaactcct gggctcaagc    24060
aattcttcct ccttagcccc aaagtgctgg cattacaggt gtgagccacc atgcctggcc    24120
cacttatttt ctagatgagg cacagaaaga ttgggagact tgaccaaggt cacgctgtca    24180
ttgagccatg agccagacta gaatccaggc ctgaagctgg gtgcgctgtc ccaggactgg    24240
ctggcactga gtaccatttg ccagcgagca tctctctggg aagctgactt ctgcccgta   24300
cctggaggac tgtagacctt ggtggtggcg ccgtcactct ggggcttcct gcctcccact    24360
gatgcccgca ccaccctaga gggactgtca tctctcctgt cccaagcctg gactggaaag    24420
actgaagaga agccttaagt aggccaggac agctcagtgt gccatggctg cccgtccttc    24480
agtggtccct ggcatgagga cctgcaacac atctgttagt cttctcaaca ggcccttggc    24540
ccggtcccct ttaagagacg agaagggctg ggcacggtga ctcacacctc taatcccagc    24600
actttgaag  gctgaggctg gagaagggct ccagcttagg agttcaggac cagcctggcc    24660
aacatggtga gaccctgttt tgttttgttt tttgttttt  tgagatggag tcttgctctg    24720
tcgcccaggc tggagtgcag                                                24740
```

<210> SEQ ID NO 42
<211> LENGTH: 25
<212> TYPE: DNA
<213> ORGANISM: Rattus norvegicus

```
<400> SEQUENCE: 42
gcactacctt gaaggaatcc atggt                                          25

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: primer for
      RT-PCR & Real-time PCR of SYBR Green - Aggrecan (forward)

<400> SEQUENCE: 43
aggatggctt ccaccagtgc                                                20

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: primer for
      RT-PCR & Real-time PCR of SYBR Green - Aggrecan (reverse)

<400> SEQUENCE: 44
tgcgtaaaag acctcaccct cc                                             22

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: primer for
      RT-PCR & Real-time PCR of SYBR Green - BMP-2 (forward)

<400> SEQUENCE: 45
cacaagtcag tgggagagc                                                 19

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: primer for
      RT-PCR & Real-time PCR of SYBR Green - BMP-2 (reverse)

<400> SEQUENCE: 46
gcttccgctg tttgtgtttg                                                20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: primer for
      RT-PCR & Real-time PCR of SYBR Green - GAPDH (forward)

<400> SEQUENCE: 47
accacagtcc atgccatcac                                                20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: primer for
      RT-PCR & Real-time PCR of SYBR Green - GAPDH (reverse)

<400> SEQUENCE: 48
```

-continued

```
tccaccaccc tgttgctgta                                              20

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: primer for
      real-time PCR of TaqMan - Overexpression of LMP-1 (forward)

<400> SEQUENCE: 49
aatacgactc actatagggc tcga                                         24

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: primer for
      real-time PCR of TaqMan - Overexpression of LMP-1 (reverse)

<400> SEQUENCE: 50
ggaagcccca aggtgct                                                 17

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: probe for
      real-time PCR of TaqMan - Overexpression of LMP-1 (reverse)

<400> SEQUENCE: 51
agccggcatc atggattcct tcaa                                         24
```

METHODS OF EXPRESSING LIM MINERALIZATION PROTEIN IN NON-OSSEOUS CELLS

This application claims priority from U.S. Provisional Application Ser. No. 60/331,321 filed Nov. 14, 2001. The entirety of that provisional application is incorporated herein by reference.

This application is related to U.S. patent application Ser. No. 09/124,238, filed Jul. 29, 1998, now U.S. Pat. No. 6,300,127, this application is also a continuation-in-part of U.S. patent application Ser. No. 09/959,578, filed Apr. 28, 2000, issued as U.S. Pat. No. 7,045,614. Each of these applications is incorporated by reference herein in its entirety. The instant application is also a continuation-in-part application of U.S. patent application Ser. No. 09/986,625 filed on Nov. 9, 2001 and issued on Feb. 22, 2005 as U.S. Pat. No. 6,858,431, which application is a divisional of, and claims the benefit of U.S. patent application Ser. No. 09/721,975, filed Nov. 27, 2000, now U.S. Pat. No. 6,444,803, which is a continuation of, and claims the benefit of, application Ser. No. 09/124,238, filed Jul. 29, 1998, now U.S. Pat. No. 6,300,127, which claimed the benefit of U.S. Provisional Application Nos. 60/054,219, filed Jul. 30, 1997, and 60/080,407, filed Apr. 2, 1998.

BACKGROUND OF THE INVENTION

1. Field of the Invention

The field of the invention relates generally to methods for expressing LIM mineralization proteins in non-osseous cells such as intervertebral disc cells or cells of the nucleus pulposus. More specifically, the field of the invention relates to transfecting non-osseous cells such as intervertebral disc cells with a nucleic acid encoding a LIM mineralization protein.

2. Background of the Technology

Osteoblasts are thought to differentiate from pluripotent mesenchymal stem cells. The maturation of an osteoblast results in the secretion of an extracellular matrix which can mineralize and form bone. The regulation of this complex process is not well understood but is thought to involve a group of signaling glycoproteins known as bone morphogenetic proteins (BMPs). These proteins have been shown to be involved with embryonic dorsal-ventral patterning, limb bud development, and fracture repair in adult animals. B. L. Hogan, Genes & Develop., 10, 1580 (1996). This group of transforming growth factor-beta superfamily secreted proteins has a spectrum of activities in a variety of cell types at different stages of differentiation; differences in physiological activity between these closely related molecules have not been clarified. D. M. Kingsley, Trends Genet., 10, 16 (1994).

To better discern the unique physiological role of different BMP signaling proteins, we recently compared the potency of BMP-6 with that of BMP-2 and BMP-4, for inducing rat calvarial osteoblast differentiation. Boden, et al., Endocrinology, 137, 3401 (1996). We studied this process in first passage (secondary) cultures of fetal rat calvaria that require BMP or glucocorticoid for initiation of differentiation. In this model of membranous bone formation, glucocorticoid (GC) or a BMP will initiate differentiation to mineralized bone nodules capable of secreting osteocalcin, the osteoblast-specific protein. This secondary culture system is distinct from primary rat osteoblast cultures which undergo spontaneous differentiation. In this secondary system, glucocorticoid resulted in a ten-fold induction of BMP-6 mRNA and protein expression which was responsible for the enhancement of osteoblast differentiation. Boden, et al., Endocrinology, 138, 2920 (1997).

In addition to extracellular signals, such as the BMPs, intracellular signals or regulatory molecules may also play a role in the cascade of events leading to formation of new bone. One broad class of intracellular regulatory molecules are the LIM proteins, which are so named because they possess a characteristic structural motif known as the LIM domain. The LIM domain is a cysteine-rich structural motif composed of two special zinc fingers that are joined by a 2-amino acid spacer. Some proteins have only LIM domains, while others contain a variety of additional functional domains. LIM proteins form a diverse group, which includes transcription factors and cytoskeletal proteins. The primary role of LIM domains appears to be in mediating protein-protein interactions, through the formation of dimers with identical or different LIM domains, or by binding distinct proteins.

In LIM homeodomain proteins, that is, proteins having both LIM domains and a homeodomain sequence, the LIM domains function as negative regulatory elements. LIM homeodomain proteins are involved in the control of cell lineage determination and the regulation of differentiation, although LIM-only proteins may have similar roles. LIM-only proteins are also implicated in the control of cell proliferation since several genes encoding such proteins are associated with oncogenic chromosome translocations.

Humans and other mammalian species are prone to diseases or injuries that require the processes of bone repair and/or regeneration. For example, treatment of fractures would be improved by new treatment regimens that could stimulate the natural bone repair mechanisms, thereby reducing the time required for the fractured bone to heal. In another example, individuals afflicted with systemic bone disorders, such as osteoporosis, would benefit from treatment regimens that would results in systemic formation of new bone. Such treatment regimens would reduce the incidence of fractures arising from the loss of bone mass that is a characteristic of this disease.

For at least these reasons, extracellular factors, such as the BMPs, have been investigated for the purpose of using them to stimulate formation of new bone in vivo. Despite the early successes achieved with BMPs and other extracellular signalling molecules, their use entails a number of disadvantages. For example, relatively large doses of purified BMPs are required to enhance the production of new bone, thereby increasing the expense of such treatment methods. Furthermore, extracellular proteins are susceptible to degradation following their introduction into a host animal. In addition, because they are typically immunogenic, the possibility of stimulating an immune response to the administered proteins is ever present.

Due to such concerns, it would be desirable to have available treatment regimens that use an intracellular signaling molecule to induce new bone formation. Advances in the field of gene therapy now make it possible to introduce into osteogenic precursor cells, that is, cells involved in bone formation, or peripheral blood leukocytes, nucleotide fragments encoding intracellular signals that form part of the bone formation process. Gene therapy for bone formation offers a number of potential advantages: (1) lower production costs; (2) greater efficacy, compared to extracellular treatment regiments, due to the ability to achieve prolonged expression of the intracellular signal; (3) it would by-pass the possibility that treatment with extracellular signals might be hampered due to the presence of limiting numbers of receptors for those signals; (4) it permits the delivery of transfected potential osteoprogenitor cells directly to the site where localized bone formation is required; and (5) it would permit systemic bone formation, thereby providing a treatment regimen for osteoporosis and other metabolic bone diseases.

In addition to diseases of the bone, humans and other mammalian species are also subject to intervertebral disc degeneration, which is associated with, among other things, low back pain, disc herniations, and spinal stenosis. Disc degeneration is associated with a progressive loss of proteoglycan matrix. This may cause the disc to be more susceptible to bio-mechanical injury and degeneration. Accordingly, it would be desirable to have a method of stimulating proteoglycan and/or collagen synthesis by the appropriate cells, such as, for example, cells of the nucleous pulposus, cells of the annulus fibrosus, and cells of the intervertebral disc.

SUMMARY OF THE INVENTION

According to a first aspect of the invention, a method of expressing a LIM mineralization protein in a non-osseous mammalian cell is provided. According to this aspect of the invention, the method comprises transfecting the cell with an isolated nucleic acid comprising a nucleotide sequence encoding the LIM mineralization protein operably linked to a promoter. The cell can be a cell capable of producing proteoglycan and/or collagen such that the expression of the LIM mineralization protein stimulates proteoglycan and/or collagen synthesis in the cell. The isolated nucleic acid according to this aspect of the invention can be a nucleic acid which can hybridize under standard conditions to a nucleic acid molecule complementary to the full length of SEQ. ID NO: 25; and/or a nucleic acid molecule which can hybridize under highly stringent conditions to a nucleic acid molecule complementary to the full length of SEQ. ID NO: 26. The cell can be a stem cell, an intervertebral disc cell, a cell of the annulus fibrosus, or a cell of the nucleus pulposus.

According to a second aspect of the invention, a non-osseous mammalian cell comprising an isolated nucleic acid sequence encoding a LIM mineralization protein is provided. According to this aspect of the invention, the cell can be a stem cell, a cell of the nucleus pulposus, a cell of the annulus fibrosus, or an intervertebral disc cell.

According to a third aspect of the invention, a method of treating intervertebral disc injury or disease is provided. According to this aspect of the invention, the method comprises transfecting an isolated nucleic acid into a mammalian cell capable of producing proteoglycan and/or collagen. The isolated nucleic acid comprises a nucleotide sequence encoding a LIM mineralization protein operably linked to a promoter. The LIM mineralization protein stimulates proteoglycan and/or collagen synthesis in the cell.

According to a fourth aspect of the invention, an intervertebral disc implant is provided. According to this aspect of the invention, the implant comprises a carrier material and a plurality of mammalian cells comprising an isolated nucleic acid sequence encoding a LIM mineralization protein. Also according to this aspect of the invention, the carrier material comprises a porous matrix of biocompatible material and the mammalian cells are incorporated into the carrier material.

BRIEF DESCRIPTION OF THE DRAWINGS

The present invention may be better understood with reference to the accompanying drawings in which.

DETAILED DESCRIPTION OF THE PREFERRED EMBODIMENTS

Figure 1:
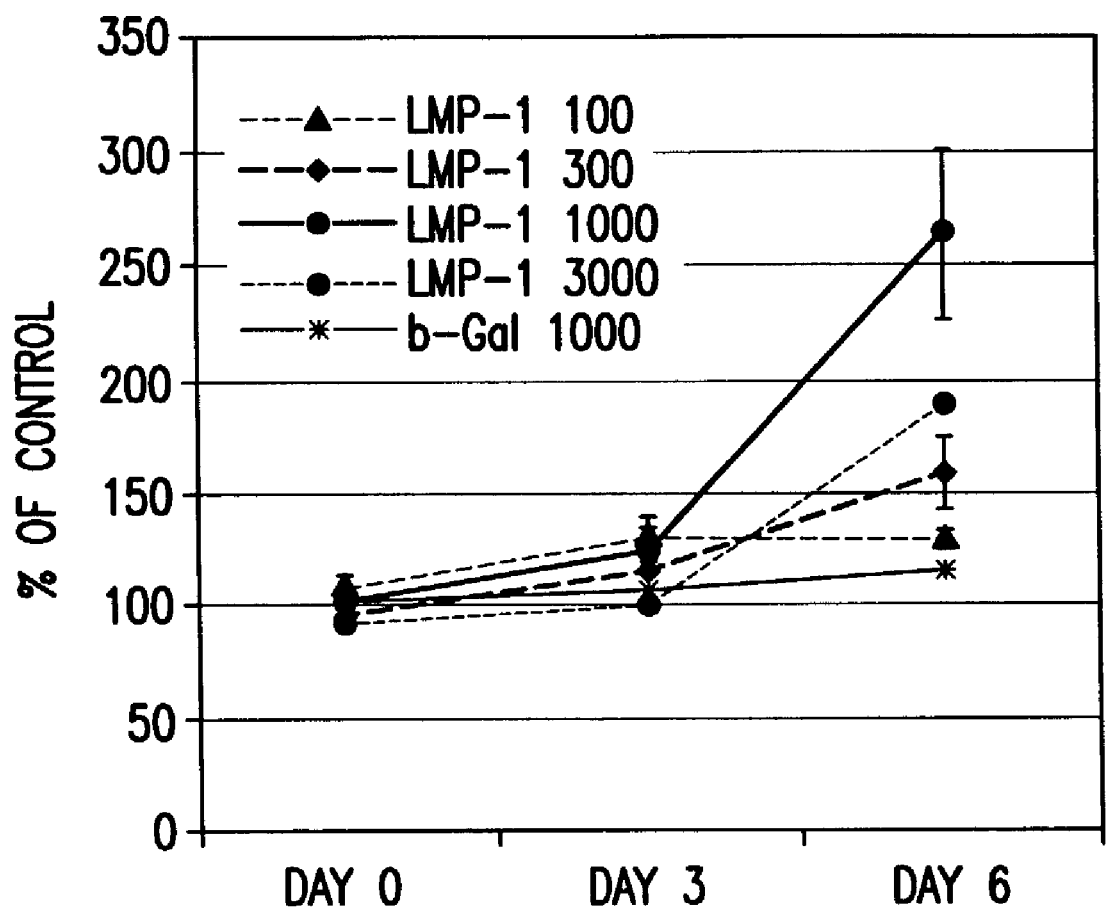
FIG. 1 is a graph showing the production of sulfated glycosaminoglycan (sGAG) after expression of HLMP-1 by rat intervertebral disc cells transfected with different MOIs.

The present invention relates to the transfection of non-osseous cells with nucleic acids encoding LIM mineralization proteins. The present inventors have discovered that transfection of non-osseous cells such as intervertebral disc cells with nucleic acids encoding LIM mineralization proteins can result in the increased synthesis of proteoglycan, collagen and other intervertebral disc components and tissue. The present invention also provides a method for treating intervertebral disc disease associated with the loss of proteoglycan, collagen, or other intervertebral disc components.

It is to be understood that both the foregoing general description and the following detailed description are exemplary and explanatory and are intended to provide further explanation of the invention as claimed.

| ABBREVIATIONS AND DEFINITIONS | |
|---|---|
| BMP | Bone Morphogenetic Protein |
| HLMP-1 | Human LMP-1, also designated as Human LIM Protein or HLMP |
| HLMP-1s | Human LMP-1 Short (truncated) protein |
| HLMPU | Human LIM Protein Unique Region |
| LMP | LIM mineralization protein |
| MEM | Minimal essential medium |
| Trm | Triamcinolone |
| β-GlyP | Beta-glycerolphosphate |
| RACE | Rapid Amplification of cDNA Ends |
| RLMP | Rat LIM mineralization protein, also designated as RLMP-1 |
| RLMPU | Rat LIM Protein Unique Region |
| RNAsin | RNase inhibitor |
| ROB | Rat Osteoblast |
| 10-4 | Clone containing cDNA sequence for RLMP (SEQ ID NO: 2) |
| UTR | Untranslated Region |
| HLMP-2 | Human LMP Splice Variant 2 |

-continued

| ABBREVIATIONS AND DEFINITIONS | |
|---|---|
| HLMP-3 | Human LMP Splice Variant 3 |
| MOI | multiplicity of infection |
| sGAG | sulfated glycosaminoglycan |
| AdHLMP-1 | Recombinant Type 5 Adenovirus comprising nucleotide sequence encoding HLMP-1 |

A LIM gene (10-4/RLMP) has been isolated from stimulated rat calvarial osteoblast cultures (SEQ. ID NO: 1, SEQ. ID NO: 2). See U.S. Pat. No. 6,300,127. This gene has been cloned, sequenced and assayed for its ability to enhance the efficacy of bone mineralization in vitro. The protein RLMP has been found to affect the mineralization of bone matrix as well as the differentiation of cells into the osteoblast lineage. Unlike other known cytokines (e.g., BMPs), RLMP is not a secreted protein, but is instead an intracellular signaling molecule. This feature has the advantage of providing intracellular signaling amplification as well as easier assessment of transfected cells. It is also suitable for more efficient and specific in vivo applications. Suitable clinical applications include enhancement of bone repair in fractures, bone defects, bone grafting, and normal homeostasis in patients presenting with osteoporosis.

The amino acid sequence of a corresponding human protein, named human LMP-1 ("HLMPI"), has also been cloned, sequenced and deduced. See U.S. Pat. No. 6,300,127. The human protein has been found to demonstrate enhanced efficacy of bone mineralization in vitro and in vivo.

Additionally, a truncated (short) version of HLMP-1, termed HLMP-1s, has been characterized. See U.S. Pat. No. 6,300,127. This short version resulted from a point mutation in one source of a cDNA clone, providing a stop codon which truncates the protein. HLMP-1s has been found to be fully functional when expressed in cell culture and in vivo.

Using PCR analysis of human heart cDNA library, two alternative splice variants (referred to as HLMP-2 and HLMP-3) have been identified that differ from HLMP-1 in a region between base pairs 325 and 444 in the nucleotide sequence encoding HLMP-1. See U.S. patent application Ser. No. 09/959,578, filed Apr. 28, 2000, pending. The HLMP-2 sequence has a 119 base pair deletion and an insertion of 17 base pairs in this region. Compared to HLMP-1, the nucleotide sequence encoding HLMP-3 has no deletions, but it does have the same 17 base pairs as HLMP-2, which are inserted at position 444 in the HLMP-1 sequence.

LMP is a pluripotent molecule, which regulates or influences a number of biological processes. The different splice variants of LMP are expected to have different biological functions in mammals. They may play a role in the growth, differentiation, and/or regeneration of various tissues. For example, some form of LMP is expressed not only in bone, but also in muscle, tendons, ligaments, spinal cord, peripheral nerves, and cartilage.

According to one aspect, the present invention relates to a method of stimulating proteoglycan and/or collagen synthesis in a mammalian cell by providing an isolated nucleic acid comprising a nucleotide sequence encoding LIM mineralization protein operably linked to a promoter; transfecting said isolated nucleic acid sequence into a mammalian cell capable of producing proteoglycan; and expressing said nucleotide sequence encoding LIM mineralization protein, whereby proteoglycan synthesis is stimulated. The mammalian cell may be a non-osseous cell, such as an intervertebral disc cell, a cell of the annulus fibrosus, or a cell of the nucleus pulposus. Transfection may occur either ex vivo or in vivo by direct injection of virus or naked DNA, such as, for example, a plasmid. In certain embodiments, the virus is a recombinant adenovirus, preferably AdHLMP-1.

Another embodiment of the invention comprises a non-osseous mammalian cell comprising an isolated nucleic acid sequence encoding a LIM mineralization protein. The non-osseous mammalian cell may be a stem cell (e.g., a pluripotential stem cell or a mesenchymal stem cell) or an intervertebral disc cell, preferably a cell of the nucleus pulposus or a cell of the annulus fibrosus.

In a different aspect, the invention is directed to a method of expressing an isolated nucleotide sequence encoding LIM mineralization protein in a non-osseous mammalian cell, comprising providing an isolated nucleic acid comprising a nucleotide sequence encoding LIM mineralization protein operably linked to a promoter; transfecting said isolated nucleic acid sequence into a non-osseous mammalian cell; and expressing said nucleotide sequence encoding LIM mineralization protein. The non-osseous mammalian cell may be a stem cell or an intervertebral disc cell (e.g., a cell of the nucleus pulposus or annulus fibrosus). Transfection may occur either ex vivo or in vivo by direct injection of virus or naked DNA, such as, for example, a plasmid. The virus can be a recombinant adenovirus, preferably AdHLMP-1.

In yet another embodiment, the invention is directed to a method of treating intervertebral disc disease by reversing, retarding or slowing disc degeneration, comprising providing an isolated nucleic acid comprising a nucleotide sequence encoding LIM mineralization protein operably linked to a promoter; transfecting said isolated nucleic acid sequence into a mammalian cell capable of producing proteoglycan; and stimulating proteoglycan synthesis in said cell by expressing said nucleotide sequence encoding LIM mineralization protein, whereby disc degeneration is reversed, halted or slowed. The disc disease may involve lower back pain, disc herniation, or spinal stenosis. The mammalian cell may be a non-osseous cell, such as a stem cell or an intervertebral disc cell (e.g., a cell of the annulus fibrosus, or a cell of the nucleus pulposus).

Transfection may occur either ex vivo or in vivo by direct injection of virus or naked DNA, such as, for example, a plasmid. In certain embodiments, the virus is a recombinant adenovirus, preferably AdHLMP-1.

The present invention relates to novel mammalian LIM proteins, herein designated LIM mineralization proteins, or LMPs. The invention relates more particularly to human LMP, known as HLMP or HLMP-1, or alternative splice variants of human LMP, which are known as HLMP-2 or HLMP-3. The Applicants have discovered that these proteins enhance bone mineralization in mammalian cells grown in vitro. When produced in mammals, LMP also induces bone formation in vivo.

Ex vivo transfection of bone marrow cells, osteogenic precursor cells, peripheral blood cells, and stem cells (e.g., pluripotential stem cells or mesenchymal stem cells) with nucleic acid that encodes a LIM mineralization protein (e.g., LMP or HLMP), followed by reimplantation of the transfected cells in the donor, is suitable for treating a variety of bone-related disorders or injuries. For example, one can use this method to: augment long bone fracture repair; generate bone in segmental defects; provide a bone graft substitute for fractures; facilitate tumor reconstruction or spine fusion; and provide a local treatment (by injection) for weak or osteoporotic bone, such as in osteoporosis of the hip, vertebrae, or wrist. Transfection with LMP or HLMP-encoding nucleic acid is also useful in: the percutaneous injection of transfected marrow cells to accelerate the repair of fractured long bones; treatment of delayed union or non-unions of long bone fractures or pseudoarthrosis of spine fusions; and for inducing new bone formation in avascular necrosis of the hip or knee.

In addition to ex vivo methods of gene therapy, transfection of a recombinant DNA vector comprising a nucleic acid sequence that encodes LMP or HLMP can be accomplished in vivo. When a DNA fragment that encodes LMP or HLMP is inserted into an appropriate viral vector, for example, an adenovirus vector, the viral construct can be injected directly into a body site were endochondral bone formation is desired. By using a direct, percutaneous injection to introduce the LMP or HLMP sequence stimulation of bone formation can be accomplished without the need for surgical intervention either to obtain bone marrow cells (to transfect ex vivo) or to reimplant them into the patient at the site where new bone is required. Alden, et al., Neurosurgical Focus (1998), have demonstrated the utility of a direct injection method of gene therapy using a cDNA that encodes BMP-2, which was cloned into an adenovirus vector.

It is also possible to carry out in vivo gene therapy by directly injecting into an appropriate body site, a naked, that is, unencapsulated, recombinant plasmid comprising a nucleic acid sequence that encodes HLMP. In this embodiment of the invention, transfection occurs when the naked plasmid DNA is taken up, or internalized, by the appropriate target cells, which have been described. As in the case of in vivo gene therapy using a viral construct, direct injection of naked plasmid DNA offers the advantage that little or no surgical intervention is required. Direct gene therapy, using naked plasmid DNA that encodes the endothelial cell mitogen VEGF (vascular endothelial growth factor), has been successfully demonstrated in human patients. Baumgartner, et al., Circulation, 97, 12, 1114-1123 (1998).

For intervertebral disc applications, ex vivo transfection may be accomplished by harvesting cells from an intervertebral disc, transfecting the cells with nucleic acid encoding LMP in vitro, followed by introduction of the cells into an intervertebral disc. The cells may be harvested from or introduced back into the intervertebral disc using any means known to those of skill in the art, such as, for example, any surgical techniques appropriate for use on the spine. In one embodiment, the cells are introduced into the intervertebral disc by injection.

Also according to the invention, stem cells (e.g., pluripotential stem cells or mesenchymal stem cells) can be transfected with nucleic acid encoding a LIM Mineralization Protein ex vivo and introduced into the intervertebral disc (e.g., by injection).

The cells transfected ex vivo can also be combined with a carrier to form an intervertebral disc implant. The carrier comprising the transfected cells can then be implanted into the intervertebral disc of a subject. Suitable carrier materials are disclosed in Helm, et al., "Bone Graft Substitutes for the Promotion of Spinal Arthrodesis", Neurosurg Focus, Vol. 10 (4): April 2001. The carrier preferably comprises a biocompatible porous matrix such as a demineralized bone matrix (DBM), a biocompatible synthetic polymer matrix or a protein matrix. Suitable proteins include extracellular matrix proteins such as collagen. The cells transfected with the LMP ex vivo can be incorporated into the carrier (i.e., into the pores of the porous matrix) prior to implantation.

Similarly, for intervertebral disc applications where the cells are transfected in vivo, the DNA may be introduced into the intevertebral disc using any suitable method known to those of skill in the art. In one embodiment, the nucleic acid is directly injected into the intervertebral space.

By using an adenovirus vector to deliver LMP into osteogenic cells, transient expression of LMP is achieved. This occurs because adenovirus does not incorporate into the genome of target cells that are transfected. Transient expression of LMP, that is, expression that occurs during the lifetime of the transfected target cells, is sufficient to achieve the objects of the invention. Stable expression of LMP, however, can occur when a vector that incorporates into the genome of the target cell is used as a delivery vehicle. Retrovirus-based vectors, for example, are suitable for this purpose.

Stable expression of LMP is particularly useful for treating various systemic bone-related disorders, such as osteoporosis and osteogenesis imperfecta. For this embodiment of the invention, in addition to using a vector that integrates into the genome of the target cell to deliver an LMP-encoding nucleotide sequence into target cells, LMP expression can be placed under the control of a regulatable promoter. For example, a promoter that is turned on by exposure to an exogenous inducing agent, such as tetracycline, is suitable.

Using this approach, one can stimulate formation of new bone on a systemic basis by administering an effective amount of the exogenous inducing agent. Once a sufficient quantity of bone mass is achieved, administration of the exogenous inducing agent can be discontinued. This process may be repeated as needed to replace bone mass lost, for example, as a consequence of osteoporosis. Antibodies specific for HLMP are particularly suitable for use in methods for assaying the osteoinductive, that is, bone-forming, potential of patient cells. In this way one can identify patients at risk for slow or poor healing of bone repair. Also, HLMP-specific antibodies are suitable for use in marker assays to identify risk factors in bone degenerative diseases, such as, for example, osteoporosis.

Following well known and conventional methods, the genes of the present invention are prepared by ligation of nucleic acid segments that encode LMP to other nucleic acid sequences, such as cloning and/or expression vectors. Methods needed to construct and analyze these recombinant vectors, for example, restriction endonuclease digests, cloning protocols, mutagenesis, organic synthesis of oligonucleotides and DNA sequencing, have been described. For DNA sequencing DNA, the dieoxyterminator method is the preferred.

Many treatises on recombinant DNA methods have been published, including Sambrook, et al., Molecular Cloning: A Laboratory Manual, $2^{nd}$ edition, Cold Spring Harbor Press, (1988), Davis. et al., Basic Methods in Molecular Biology, Elsevier (1986), and Ausubel, et al., Current Protocols in Molecular Biology, Wiley Interscience (1988). These reference manuals are specifically incorporated by reference herein.

Primer-directed amplification of DNA or cDNA is a common step in the expression of the genes of this invention. It is typically performed by the polymerase chain reaction (PCR). PCR is described in U.S. Pat. No. 4,800,159 to Mullis, et al. and other published sources. The basic principle of PCR is the exponential replication of a DNA sequence by successive cycles of primer extension. The extension products of one primer, when hybridized to another primer, becomes a template for the synthesis of another nucleic acid molecule. The primer-template complexes act as substrate for DNA polymerase, which in performing its replication function, extends the primers. The conventional enzyme for PCR applications is the thermostable DNA polymerase isolated from *Thermus aquaticus*, or Taq DNA polymerase.

Numerous variations of the basic PCR method exist, and a particular procedure of choice in any given step needed to construct the recombinant vectors of this invention is readily performed by a skilled artisan. For example, to measure cellular expression of 10-4/RLMP, RNA is extracted and reverse transcribed under standard and well known procedures. The resulting cDNA is then analyzed for the appropriate mRNA sequence by PCR.

The gene encoding the LIM mineralization protein is expressed in an expression vector in a recombinant expression system. Of course, the constructed sequence need not be the same as the original, or its complimentary sequence, but instead may be any sequence determined by the degeneracy of the DNA code that nonetheless expresses an LMP having bone forming activity. Conservative amino acid substitutions, or other modifications, such as the occurrence of an amino-terminal methionine residue, may also be employed.

A ribosome binding site active in the host expression system of choice is ligated to the 5' end of the chimeric LMP coding sequence, forming a synthetic gene. The synthetic gene can be inserted into any one of a large variety of vectors for expression by ligating to an appropriately linearized plasmid. A regulatable promoter, for example, the *E. coli* lac promoter, is also suitable for the expression of the chimeric coding sequences. Other suitable regulatable promoters include trp, tac, recA, T7 and lambda promoters.

DNA encoding LMP is transfected into recipient cells by one of several standard published procedures, for example, calcium phosphate precipitation, DEAE-Dextran, electroporation or protoplast fusion, to form stable transformants. Calcium phosphate precipitation is preferred, particularly when performed as follows.

DNAs are coprecipitated with calcium phosphate according to the method of Graham and Van Der, Virology, 52, 456 (1973), before transfer into cells. An aliquot of 40-50 µg of DNA, with salmon sperm or calf thymus DNA as a carrier, is used for $0.5 \times 10^6$ cells plated on a 100 mm dish. The DNA is mixed with 0.5 ml of 2× Hepes solution (280 mM NaCl, 50 mM Hepes and 1.5 mM $Na_2HPO_4$, pH 7.0), to which an equal volume of 2× $CaCl_2$ (250 mM $CaCl_2$ and 10 mM Hepes, pH 7.0) is added. A white granular precipitate, appearing after 30-40 minutes, is evenly distributed dropwise on the cells, which are allowed to incubate for 4-16 hours at 37° C. The medium is removed and the cells shocked with 15% glycerol in PBS for 3 minutes. After removing the glycerol, the cells are fed with Dulbecco's Minimal Essential Medium (DMEM) containing 10% fetal bovine serum.

DNA can also be transfected using: the DEAE-Dextran methods of Kimura, et al., Virology, 49:394 (1972) and Sompayrac et al., Proc. Natl. Acad. Sci. USA, 78, 7575 (1981); the electroporation method of Potter, Proc. Natl. Acad. Sci. USA, 81, 7161 (1984); and the protoplast fusion method of Sandri-Goddin et al., Molec. Cell. Biol., 1, 743 (1981).

Phosphoramidite chemistry in solid phase is the preferred method for the organic synthesis of oligodeoxynucleotides and polydeoxynucleotides. In addition, many other organic synthesis methods are available. Those methods are readily adapted by those skilled in the art to the particular sequences of the invention.

The present invention also includes nucleic acid molecules that hybridize under standard conditions to any of the nucleic acid sequences encoding the LIM mineralization proteins of the invention. "Standard hybridization conditions" will vary with the size of the probe, the background and the concentration of the nucleic acid reagents, as well as the type of hybridization, for example, in situ, Southern blot, or hybrization of DNA-RNA hybrids (Northern blot). The determination of "standard hybridization conditions" is within the level of skill in the art. For example, see U.S. Pat. No. 5,580,775 to Fremeau, et al., herein incorporated by reference for this purpose. See also, Southern, J. Mol. Biol., 98:503 (1975), Alwine, et al., Meth. Enzymol., 68:220 (1979), and Sambrook, et al., Molecular Cloning: A Laboratory Manual, $2^{nd}$ edition, Cold Spring Harbor Press, 7.19-7.50 (1989).

One preferred set of standard hybrization conditions involves a blot that is prehybridized at 42° C. for 2 hours in 50% formamide, 5×SSPE (150 nM NaCl, 10 mM Na $H_2PO_4$ [pH 7.4], 1 mM EDTA [pH 8.0]) 1 5× Denhardt's solution (20 mg Ficoll, 20 mg polyvinylpyrrolidone and 20 mg BSA per 100 ml water), 10% dextran sulphate, 1% SDS and 100 µg/ml salmon sperm DNA. A $^{32}$P-labeled cDNA probe is added, and hybridization is continued for 14 hours. Afterward, the blot is washed twice with 2×SSPE, 0.1% SDS for 20 minutes at 22° C., followed by a 1 hour wash at 65° C. in 0.1×SSPE, 0.1% SDS. The blot is then dried and exposed to x-ray film for 5 days in the presence of an intensifying screen.

Under "highly stringent conditions," a probe will hybridize to its target sequence if those two sequences are substantially identical. As in the case of standard hybridization conditions, one of skill in the art can, given the level of skill in the art and the nature of the particular experiment, determine the conditions under which only susbstantially identical sequences will hybridize.

According to one aspect of the present invention, an isolated nucleic acid molecule comprising a nucleic acid sequence encoding a LIM mineralization protein is provided. The nucleic acid molecule according to the invention can be a molecule which hybridizes under standard conditions to a nucleic acid molecule complementary to the full length of SEQ. ID NO: 25 and/or which hybridizes under highly stringent conditions to a nucleic acid molecule complementary to the full length of SEQ. ID NO: 26. More specifically, the isolated nucleic acid molecule according to the invention can encode HLMP-1, HLMP-1s, RLMP, HLMP-2, or HLMP-3.

Another aspect of the invention includes the proteins encoded by the nucleic acid sequences. In still another embodiment, the invention relates to the identification of such proteins based on anti-LMP antibodies. In this embodiment, protein samples are prepared for Western blot analysis by lysing cells and separating the proteins by SDS-PAGE. The proteins are transferred to nitrocellulose by electrobloffing as described by Ausubel, et al., Current Protocols in Molecular Biology, John Wiley and Sons (1987). After blocking the filter with instant nonfat dry milk (1 gm in 100 ml PBS), anti-LMP antibody is added to the filter and incubated for 1 hour at room temperature. The filter is washed thoroughly with phosphate buffered saline (PBS) and incubated with horseradish peroxidase (HRPO)-antibody conjugate for 1 hour at room temperature. The filter is again washed thoroughly with PBS and the antigen bands are identified by adding diaminobenzidine (DAB).

Monospecific antibodies are the reagent of choice in the present invention, and are specifically used to analyze patient cells for specific characteristics associated with the expression of LMP. "Monospecific antibody" as used herein is defined as a single antibody species or multiple antibody species with homogenous binding characteristics for LMP. "Homogeneous binding" as used herein refers to the ability of the antibody species to bind to a specific antigen or epitope, such as those associated with LMP, as described above. Monospecific antibodies to LMP are purified from mammalian antisera containing antibodies reactive against LMP or are prepared as monoclonal antibodies reactive with LMP using the technique of Kohler and Milstein. Kohler et al., Nature, 256, 495-497 (1975). The LMP specific antibodies are raised by immunizing animals such as, for example, mice, rats, guinea pigs, rabbits, goats or horses, with an appropriate concentration of LMP either with or without an immune adjuvant.

In this process, pre-immune serum is collected prior to the first immunization. Each animal receives between about 0.1 mg and about 1000 mg of LMP associated with an acceptable immune adjuvant, if desired. Such acceptable adjuvants include, but are not limited to, Freund's complete, Freund's incomplete, alum-precipitate, water in oil emulsion containing *Corynebacterium parvum* and tRNA adjuvants. The initial immunization consists of LMP in, preferably, Freund's complete adjuvant injected at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with LMP are prepared by immunizing inbred mice, preferably Balb/c mice, with LMP. The mice are immunized by the IP or SC route with about 0.1 mg to about 10 mg, preferably about 1 mg, of LMP in about 0.5 ml buffer or saline incorporated in an equal volume of an acceptable adjuvant, as discussed above. Freund's complete adjuvant is preferred. The mice receive an initial immunization on day 0 and are rested for about 3-30 weeks. Immunized mice are given one or more booster immunizations of about 0.1 to about 10 mg of LMP in a buffer solution such as phosphate buffered saline by the intravenous (IV) route. Lymphocytes from antibody-positive mice, preferably splenic lymphocytes, are obtained by removing the spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1,000 mol. wt., at concentrations from about 30% to about 50%. Fused hybridoma cells are selected by growth in hypoxanthine, thymidine and aminopterin in supplemented Dulbecco's Modified Eagles Medium (DMEM) by procedures known in the art. Supernatant fluids are collected from growth positive wells on about days 14, 18, and 21, and are screened for antibody production by an immunoassay such as solid phase immunoradioassay (SPIRA) using LMP as the antigen. The culture fluids are also tested in the Ouchterlony precipitation assay to determine the isotype of the mAb. Hybridoma cells from antibody positive wells are cloned by a technique such as the soft agar technique of MacPherson, "Soft Agar Techniques: Tissue Culture Methods and Applications", Kruse and Paterson (eds.), Academic Press (1973). See, also, Harlow, et al., Antibodies: A Laboratory Manual, Cold Spring Laboratory (1988).

Monoclonal antibodies may also be produced in vivo by injection of pristane-primed Balb/c mice, approximately 0.5 ml per mouse, with about $2 \times 10^6$ to about $6 \times 10^6$ hybridoma cells about 4 days after priming. Ascites fluid is collected at approximately 8-12 days after cell transfer and the monoclonal antibodies are purified by techniques known in the art.

In vitro production in anti-LMP mAb is carried out by growing the hydridoma cell line in DMEM containing about 2% fetal calf serum to obtain sufficient quantities of the specific mAb. The mAb are purified by techniques known in the art.

Antibody titers of ascites or hybridoma culture fluids are determined by various serological or immunological assays, which include, but are not limited to, precipitation, passive agglutination, enzyme-linked immunosorbent antibody (ELISA) technique and radioimmunoassay (RIA) techniques. Similar assays are used to detect the presence of the LMP in body fluids or tissue and cell extracts.

It is readily apparent to those skilled in the art that the above described methods for producing monospecific antibodies may be utilized to produce antibodies specific for polypeptide fragments of LMP, full-length nascent LMP polypeptide, or variants or alleles thereof.

In another embodiment, the invention is directed to alternative splice variants of HLMP-1. PCR analysis of human heart cDNA revealed mRNA for two HLMP alternative splice variants, named HLMP-2 and HLMP-3, that differ from HLMP-1 in a region between base pairs 325 and 444 in the HLMP-1 sequence. The HLMP-2 sequence has a 119 base pair deletion and an insertion of 17 base pairs in this region. These changes preserve the reading frame, resulting in a 423 amino acid protein, which compared to HLMP-1, has a net loss of 34 amino acids (40 amino acids deleted plus 6 inserted amino acids). HLMP-2 contains the c-terminal LIM domains that are present in HLMP-1.

Compared to HLMP-1, HLMP-3 has no deletions, but it does have the same 17 base pair insertion at position 444. This insertion shifts the reading frame, causing a stop codon at base pairs 459-461. As a result, HLMP-3 encodes a protein of 153 amino acids. This protein lacks the c-terminal LIM domains that are present in HLMP-1 and HLMP-2. The predicted size of the proteins encoded by HLMP-2 and HLMP-3 was confirmed by western blot analysis.

PCR analysis of the tissue distribution of the three splice variants revealed that they are differentially expressed, with specific isoforms predominating in different tissues. HLMP-1 is apparently the predominant form expressed in leukocytes, spleen, lung, placenta, and fetal liver. HLMP-2 appears to be the predominant isoform in skeletal muscle, bone marrow, and heart tissue. HLMP-3, however, was not the predominant isoform in any tissue examined.

Over-expression of HLMP-3 in secondary rat osteoblast cultures induced bone nodule formation (287±56) similar to the effect seen for glucicorticoid (272±7) and HLMP-1 (232±200). Since HLMP-3 lacks the C-terminal LIM domains, there regions are not required for osteoinductive activity.

Over-expression of HLMP-2, however, did not induce nodule formation (11±3). These data suggest that the amino acids encoded by the deleted 119 base pairs are necessary for osteoinduction. The data also suggest that the distribution of HLMP splice variants may be important for tissue-specific function. Surprisingly, we have shown that HLMP-2 inhibits steroid-induced osteoblast formation in secondary rat osteoblast cultures. Therefore, HLMP-2 may have therapeutic utility in clinical situations where bone formation is not desirable.

On Jul. 22, 1997, a sample of 10-4/RLMP in a vector designated pCMV2/RLMP (which is vector pRc/CMV2 with insert 10-4 clone/RLMP) was deposited with the American Type Culture Collection (ATCC), 12301 Parklawn Drive, Rockville, Md. 20852. The culture accession number for that deposit is 209153. On Mar. 19, 1998, a sample of the vector pHis-A with insert HLPM-1s was deposited at the American Type Culture Collection ("ATCC"). The culture accession number for that deposit is 209698. On Apr. 14, 2000, samples of plasmids pHAhLMP-2 (vector pHisA with cDNA insert derived from human heart muscle cDNA with HLMP-2) and pHAhLMP-3 (vector pHisA with cDNA insert derived from human heart muscle cDNA with HLMP-3) were deposited with the ATCC, 10801 University Blvd., Manassas, Va., 20110-2209, USA, under the conditions of the Budapest treaty. The accession numbers for these deposits are PTA-1698 and PTA-1699, respectively. These deposits, as required by the Budapest Treaty, will be maintained in the ATCC for at least 30 years and will be made available to the public upon the grant of a patent disclosing them. It should be understood that the availability of a deposit does not constitute a license to practice the subject invention in derogation of patent rights granted by government action.

In assessing the nucleic acids, proteins, or antibodies of the invention, enzyme assays, protein purification, and other conventional biochemical methods are employed. DNA and RNA are analyzed by Southern blotting and Northern blotting techniques, respectively. Typically, the samples analyzed are size fractionated by gel electrophoresis. The DNA or RNA in the gels are then transferred to nitrocellulose or nylon membranes. The blots, which are replicas of sample patterns in the gels, were then hybridized with probes. Typically, the probes are radio-labeled, preferably with $^{32}P$, although one could label the probes with other signal-generating molecules known to those in the art. Specific bands of interest can then be visualized by detection systems, such as autoradiography.

For purposes of illustrating preferred embodiments of the present invention, the following, non-limiting examples are included. These results demonstrate the feasibility of inducing or enhancing the formation of bone using the LIM mineralization proteins of the invention, and the isolated nucleic acid molecules encoding those proteins.

Example 1

Calvarial Cell Culture

Rat calvarial cells, also known as rat osteoblasts ("ROB"), were obtained from 20-day pre-parturition rats as previously described. Boden. et al., Endocrinology, 137, 8, 3401-3407 (1996). Primary cultures were grown to confluence (7 days), trypsinized, and passed into 6-well plates ($1\times10^5$ cells/35 mm well) as first subculture cells. The subculture cells, which were confluent at day 0, were grown for an additional 7 days. Beginning on day 0, media were changed and treatments (Trm and/or BMPs) were applied, under a laminar flow hood, every 3 or 4 days. The standard culture protocol was as follows: days 1-7, MEM, 10% FBS, 50 µg/ml ascorbic acid, ±stimulus; days 8-14, BGJb medium, 10% FBS, 5 mM β-GlyP (as a source of inorganic phosphate to permit mineralization). Endpoint analysis of bone nodule formation and osteocalcin secretion was performed at day 14. The dose of BMP was chosen as 50 ng/ml based on pilot experiments in this system that demonstrated a mid-range effect on the dose-response curve for all BMPs studied.

Example 2

Antisense Treatment and Cell Culture

To explore the potential functional role of LMP-1 during membranous bone formation, we synthesized an antisense oligonucleotide to block LMP-1 mRNA translation and treated secondary osteoblast cultures that were undergoing differentiation initiated by glucocorticoid. Inhibition of RLMP expression was accomplished with a highly specific antisense oligonucleotide (having no significant homologies to known rat sequences) corresponding to a 25 bp sequence spanning the putative translational start site (SEQ. ID NO: 42). Control cultures either did not receive oligonucleotide or they received sense oligonucleotide. Experiments were performed in the presence (preincubation) and absence of lipofectamine. Briefly, 22 µg of sense or antisense RLMP oligonucleotide was incubated in MEM for 45 minutes at room temperature. Following that incubation, either more MEM or pre-incubated lipofectamine/MEM (7% v/v; incubated 45 minutes at room temperature) was added to achieve an oligonucleotide concentration of 0.2 µM. The resulting mixture was incubated for 15 minutes at room temperature. Oligonucleotide mixtures were then mixed with the appropriate medium, that is, MEM/Ascorbate/±Trm, to achieve a final oligonucleotide concentration of 0.1 µM.

Cells were incubated with the appropriate medium (±stimulus) in the presence or absence of the appropriate oligonucleotides. Cultures originally incubated with lipofectamine were re-fed after 4 hours of incubation (37° C.; 5% $CO_2$) with media containing neither lipofectamine nor oligonucleotide. All cultures, especially cultures receiving oligonucleotide, were re-fed every 24 hours to maintain oligonucleotide levels.

LMP-1 antisense oligonucleotide inhibited mineralized nodule formation and osteocalcin secretion in a dose-dependent manner, similar to the effect of BMP-6 oligonucleotide. The LMP-1 antisense block in osteoblast differentiation could not be rescued by addition of exogenous BMP-6, while the BMP-6 antisense oligonucleotide inhibition was reversed with addition of BMP-6. This experiment further confirmed the upstream position of LMP-1 relative to BMP-6 in the osteoblast differentiation pathway. LMP-1 antisense oligonucleotide also inhibited spontaneous osteoblast differentiation in primary rat osteoblast cultures.

Example 3

Quantitation of Mineralized Bone Nodule Formation

Cultures of ROBs prepared according to Examples 1 and 2 were fixed overnight in 70% ethanol and stained with von Kossa silver stain. A semi-automated computerized video image analysis system was used to quantitate nodule count and nodule area in each well. Boden. et al., Endocrinology, 137, 8, 3401-3407 (1996). These values were then divided to calculate the area per nodule values. This automated process was validated against a manual counting technique and demonstrated a correlation coefficient of 0.92 (p<0.000001). All data are expressed as the mean±standard error of the mean (S.E.M.) calculated from 5 or 6 wells at each condition. Each experiment was confirmed at least twice using cells from different calvarial preparations.

Example 4

Quantitation of Osteocalcin Secretion

Osteocalcin levels in the culture media were measured using a competitive radioimmunoassay with a monospecific polygonal antibody (Pab) raised in our laboratory against the C-terminal nonapeptide of rat osteocalcin as described in Nanes. et al., Endocrinology, 127:588 (1990). Briefly, 1 µg of nonapeptide was iodinated with 1 mCi $^{125}$I-Na by the lactoperoxidase method. Tubes containing 200 gl of assay buffer (0.02 M sodium phosphate, 1 mM EDTA, 0.001% thimerosal, 0.025% BSA) received media taken from cell cultures or osteocalcin standards (0-12,000 fmole) at 100 gl/tube in assay buffer. The Pab (1:40,000; 100 µl) was then added, followed by the iodinated peptide (12,000 cpm; 100 µl). Samples tested for non-specific binding were prepared similarly but contained no antibody.

Bound and free PAbs were separated by the addition of 700 µl goat antirabbit IgG, followed by incubation for 18 hours at 4° C. After samples were centrifuged at 1200 rpm for 45 minutes, the supernatants were decanted and the precipitates counted in a gamma counter. Osteocalcin values were reported in fmole/100 µl, which was then converted to pmole/ml medium (3-day production) by dividing those values by 100. Values were expressed as the mean±S.E.M. of triplicate determinations for 5-6 wells for each condition. Each experiment was confirmed at least two times using cells from different calvarial preparations.

Example 5

Effect of Trm and RLMP on Mineralization In Vitro

There was little apparent effect of either the sense or antisense oligonucleotides on the overall production of bone nodules in the non-stimulated cell culture system. When ROBs were stimulated with Trm, however, the antisense oligonucleotide to RLMP inhibited mineralization of nodules by >95%. The addition of exogenous BMP-6 to the oligonucleotide-treated cultures did not rescue the mineralization of RLMP-antisense-treated nodules.

Osteocalcin has long been synonymous with bone mineralization, and osteocalcin levels have been correlated with nodule production and mineralization. The RLMP-antisense oligonucleotide significantly decreases osteocalcin production, but the nodule count in antisense-treated cultures does not change significantly. In this case, the addition of exogenous BMP-6 only rescued the production of osteocalcin in RLMP-antisense-treated cultures by 10-15%. This suggests that the action of RLMP is downstream of, and more specific than, BMP-6.

Example 6

Harvest and Purification of RNA

Cellular RNA from duplicate wells of ROBs (prepared according to Examples 1 and 2 in 6-well culture dishes) was harvested using 4M guanidine isothiocyanate (GIT) solution to yield statistical triplicates. Briefly, culture supernatant was aspirated from the wells, which were then overlayed with 0.6 ml of GIT solution per duplicate well harvest. After adding the GIT solution, the plates were swirled for 5-10 seconds (being as consistent as possible). Samples were saved at −70° C. for up to 7 days before further processing.

RNA was purified by a slight modification of standard methods according to Sambrook, et al. Molecular Cloning: a Laboratory Manual, Chapter 7.19, 2$^{nd}$ Edition, Cold Spring Harbor Press (1989). Briefly, thawed samples received 60 µl 2.0 M sodium acetate (pH 4.0), 550 µl phenol (water saturated) and 150 µl chloroform:isoamyl alcohol (49:1). After vortexing, the samples were centrifuged (10000×g; 20 minutes; 4° C.), the aqueous phase transferred to a fresh tube, 600 µl isopropanol was added and the RNA precipitated overnight at −20° C.

Following the overnight incubation, the samples were centrifuged (10000×g; 20 minutes) and the supernatant was aspirated gently. The pellets were resuspended in 400 µl DEPC-treated water, extracted once with phenol:chloroform (1:1), extracted with chloroform:isoamyl alcohol (24:1) and precipitated overnight at −20° C. after addition of 40 µl sodium acetate (3.0 M; pH 5.2) and 1.0 ml absolute ethanol. To recover the cellular RNA, the samples were centrifuged (10000×g; 20 min), washed once with 70% ethanol, air dried for 5-10 minutes and resuspended in 20 µl of DEPC-treated water. RNA concentrations were calculated from optical densities that were determined with a spectrophotometer.

Example 7

Reverse Transcription-Polymerase Chain Reaction

Heated total RNA (5 µg in 10.5 µl total volume DEPC-H$_2$O at 65° C. for 5 minutes) was added to tubes containing 4 µl 5× MMLV-RT buffer, 2 µl dNTPs, 2 µl dT17 primer (10 pmol/ml), 0.5 µl RNAsin (40 U/ml) and 1 µl MMLV-RT (200 units/µl). The samples were incubated at 37° C. for 1 hour, then at 95° C. for 5 minutes to inactivate the MMLV-RT. The samples were diluted by addition of 80 µl of water.

Reverse-transcribed samples (5 µl) were subjected to polymerase-chain reaction using standard methodologies (50 µl total volume). Briefly, samples were added to tubes containing water and appropriate amounts of PCR buffer, 25 mM MgCl$_2$, dNTPs, forward and reverse primers for glyceraldehyde 3-phosphate dehydrogenase (GAP, a housekeeping gene) and/or BMP-6, $^{32}$P-dCTP, and Taq polymerase. Unless otherwise noted, primers were standardized to run consistently at 22 cycles (94° C., 30"; 58° C., 30"; 72° C., 20").

Example 8

Quantitation of RT-PCR Products by Polyacrylamide Gel Electrophoresis (PAGE) and PhosphorImager Analysis RT-PCR products received 5 µl/tube loading dye, were mixed, heated at 65° C. for 10 min and centrifuiged. Ten µl of each reaction was subjected to PAGE (12% polyacrylamide: bis; 15 V/well; constant current) under standard conditions. Gels were then incubated in gel preserving buffer (10% v/v glycerol, 7% v/v acetic acid, 40% v/v methanol, 43% deionized water) for 30 minutes, dried (80° C.) in vacuo for 1-2 hours and developed with an electronically-enhanced phosphoresence imaging system for 6-24 hours. Visualized bands were analyzed. Counts per band were plotted graphically.

Example 9

Differential Display PCR

RNA was extracted from cells stimulated with glucocorticoid (Trm, 1 nM). Heated, DNase-treated total RNA (5 µg in 10.5 µl total volume in DEPC-H$_2$O at 65° C. for 5 minutes) was reverse transcribed as described in Example 7, but H-T$_{11}$M (SEQ. ID. NO: 4) was used as the MMLV-RT primer. The resulting cDNAs were PCR-amplified as described above, but with various commercial primer sets (for example, H-T$_{11}$G (SEQ. ID NO: 4) and H-AP-10 (SEQ. ID NO: 5); GenHunter Corp, Nashville, Tenn.). Radio-labeled PCR products were fractionated by gel electrophoresis on a DNA sequencing gel. After electrophoresis, the resulting gels were dried in vacuo and autoradiographs were exposed overnight. Bands representing differentially-expressed cDNAs were excised from the gel and reamplified by PCR using the method of Conner. et al., Proc. Natl. Acad. Sci. USA, 88, 278 (1983). The products of PCR reamplification were cloned into the vector PCR-11 (TA cloning kit; InVitrogen, Carlsbad, Calif.).

Example 10

Screening of a UMR 106 Rat Osteosarcoma Cell cDNA Library

A UMR 106 library ($2.5 \times 10^{10}$ pfu/ml) was plated at $5 \times 10^4$ pfu/ml onto agar plates (LB bottom agar) and the plates were incubated overnight at 37° C. Filter membranes were overlaid onto plates for two minutes. Once removed, the filters were denatured, rinsed, dried and UV cross-linked. The filters were then incubated in pre-hyridization buffer (2× PIPES [pH 6.5], 5% formamide, 1% SDS and 100 µg/ml denatured salmon sperm DNA) for 2 h at 42° C. A 260 base-pair radio-labeled probe (SEQ. ID NO: 3; $^{32}$P labeled by random priming) was added to the entire hybridization mix/filters, followed by hybridization for 18 hours at 42° C. The membranes were washed once at room temperature (10 min, 1×SSC, 0.1% SDS) and three times at 55° C. (15 min, 0.1×SSC, 0.1% SDS).

After they were washed, the membranes were analyzed by autoradiography as described above. Positive clones were plaque purified. The procedure was repeated with a second filter for four minutes to minimize spurious positives. Plaque-purified clones were rescued as lambda SK(−) phagemids. Cloned cDNAs were sequenced as described below.

Example 11

Sequencing of Clones

Cloned cDNA inserts were sequenced by standard methods. Ausubel, et al., Current Protocols in Molecular Biology, Wiley Interscience (1988). Briefly, appropriate concentrations of termination mixture, template and reaction mixture were subjected to an appropriate cycling protocol (95° C., 30 s; 68° C., 30 s; 72° C., 60 s; ×25). Stop mixture was added to terminate the sequencing reactions. After heating at 92° C. for 3 minutes, the samples were loaded onto a denaturing 6% polyacrylamide sequencing gel (29:1 acrylamide:bisacrylamide). Samples were electrophoresed for about 4 hours at 60 volts, constant current. After electrophoresis, the gels were dried in vacuo and autoradiographed.

The autoradiographs were analyzed manually. The resulting sequences were screened against the databases maintained by the National Center for Biotechnology Information (NIH, Bethesda, Md.; hftp://www.ncbi.nlm.nih.gov/) using the BLASTN program set with default parameters. Based on the sequence data, new sequencing primers were prepared and the process was repeated until the entire gene had been sequenced. All sequences were confirmed a minimum of three times in both orientations.

Nucleotide and amino acid sequences were also analyzed using the PCGENE software package (version 16.0). Percent homology values for nucleotide sequences were calculated by the program NALIGN, using the following parameters: weight of non-matching nucleotides, 10; weight of non-matching gaps, 10; maximum number of nucleotides considered, 50; and minimum number of nucleotides considered, 50.

For amino acid sequences, percent homology values were calculated using PALIGN. A value of 10 was selected for both the open gap cost and the unit gap cost.

Example 12

Cloning of RLMP cDNA

The differential display PCR amplification products described in Example 9 contained a major band of approximately 260 base pairs. This sequence was used to screen a rat osteosarcoma (UMR 106) cDNA library. Positive clones were subjected to nested primer analysis to obtain the primer sequences necessary for amplifying the full length cDNA. (SEQ. ID NOs: 11, 12, 29, 30 and 31). One of those positive clones selected for further study was designated clone 10-4.

Sequence analysis of the full-length cDNA in clone 10-4, determined by nested primer analysis, showed that clone 10-4 contained the original 260 base-pair fragment identified by differential display PCR. Clone 10-4 (1696 base pairs; SEQ ID NO: 2) contains an open reading frame of 1371 base pairs encoding a protein having 457 amino acids (SEQ. ID NO: 1). The termination codon, TGA, occurs at nucleotides 1444-1446. The polyadenylation signal at nucleotides 1675-1680, and adjacent poly(A)$^+$ tail, was present in the 3' noncoding region. There were two potential N-glycosylation sites, Asn-Lys-Thr and Asn-Arg-Thr, at amino acid positions 113-116 and 257-259 in SEQ. ID NO: 1, respectively. Two potential cAMP- and cGMP-dependent protein kinase phosphorylation sites, Ser and Thr, were found at amino acid positions 191 and 349, respectively. There were five potential protein kinase C phosphorylation sites, Ser or Thr, at amino acid positions 3, 115, 166, 219, 442. One potential ATP/GTP binding site motif A (P-loop), Gly-Gly-Ser-Asn-Asn-Gly-Lys-Thr, was determined at amino acid positions 272-279.

In addition, two highly conserved putative LIM domains were found at amino acid positions 341-391 and 400-451. The putative LIM domains in this newly identified rat cDNA clone showed considerable homology with the LIM domains of other known LIM proteins. However, the overall homology with other rat LIM proteins was less than 25%. RLMP (also designated 10-4) has 78.5% amino acid homology to the human enigma protein (see U.S. Pat. No. 5,504,192), but only 24.5% and 22.7% amino acid homology to its closest rat homologs, CLP-36 and RIT-18, respectively.

Example 13

Northern Blot Analysis of RLMP Expression

Thirty µg of total RNA from ROBs, prepared according to Examples 1 and 2, was size fractionated by formaldehyde gel electrophoresis in 1% agarose flatbed gels and osmotically transblotted to nylon membranes. The blot was probed with a 600 base pair EcoR1 fragment of full-length 10-4 cDNA labeled with $^{32}$P-dCTP by random priming.

Northern blot analysis showed a 1.7 kb mRNA species that hybridized with the RLMP probe. RLMP mRNA was up-regulated approximately 3.7-fold in ROBs after 24 hours exposure to BMP-6. No up-regulation of RMLP expression was seen in BMP-2 or BMP-4-stimulated ROBs at 24 hours.

Example 14

Statistical Methods

For each reported nodule/osteocalcin result, data from 5-6 wells from a representative experiment were used to calculate the mean±S.E.M. Graphs may be shown with data normalized to the maximum value for each parameter to allow simultaneous graphing of nodule counts, mineralized areas and osteocalcin.

For each reported RT-PCR, RNase protection assay or Western blot analysis, data from triplicate samples of representative experiments, were used to determine the mean±S.E.M. Graphs may be shown normalized to either day 0 or negative controls and expressed as fold-increase above control values.

Statistical significance was evaluated using a one-way analysis of variance with post-hoc multiple comparison corrections of Bonferroni as appropriate. D. V. Huntsberger, "The Analysis of Variance", Elements of Statistical Variance, P. Billingsley (ed.), Allyn & Bacon Inc., Boston, Mass., 298-330 (1977) and SigmaStat, Jandel Scientific, Corte Madera, Calif. Alpha levels for significance were defined as p<0.05.

Example 15

Detection of Rat LIM Mineralization Protein by Western Blot Analysis

Polyclonal antibodies were prepared according to the methods of England, et al., Biochim.Biophys. Acta, 623, 171 (1980) and Timmer, et al., J. Biol. Chem., 268, 24863 (1993).

HeLa cells were transfected with pCMV2/RLMP. Protein was harvested from the transfected cells according to the method of Hair, et al., Leukemia Research, 20, 1 (1996). Western Blot Analysis of native RLMP was performed as described by Towbin, et al., Proc. Natl. Acad. Sci. USA, 76:4350 (1979).

Example 16

Synthesis of the Rat LMP-Unique (RLMPU) Derived Human PCR Product

Based on the sequence of the rat LMP-1 cDNA, forward and reverse PCR primers (SEQ. ID NOS: 15 and 16) were synthesized and a unique 223 base-pair sequence was PCR amplified from the rat LMP-1 cDNA. A similar PCR product was isolated from human MG63 osteosarcoma cell cDNA with the same PCR primers.

RNA was harvested from MG63 osteosarcoma cells grown in T-75 flasks. Culture supernatant was removed by aspiration and the flasks were overlayed with 3.0 ml of GIT solution per duplicate, swirled for 5-10 seconds, and the resulting solution was transferred to 1.5 ml eppendorf tubes (6 tubes with 0.6 ml/tube). RNA was purified by a slight modification of standard methods, for example, see Sambrook, et al., Molecular Cloning: A Laboratory Manual, Chapter 7, page 19, Cold Spring Harbor Laboratory Press (1989) and Boden, et al., Endocrinology, 138, 2820-2828 (1997). Briefly, the 0.6 ml samples received 60 µl 2.0 M sodium acetate (pH 4.0), 550 µl water saturated phenol and 150 µl chloroform:isoamyl alcohol (49:1). After addition of those reagents, the samples were vortexed, centrifuged (10000×g; 20 min; 4C) and the aqueous phase transferred to a fresh tube. Isopropanol (600 µl) was added and the RNA was precipitated overnight at −20° C. The samples were centrifuged (10000×g; 20 minutes) and the supernatant was aspirated gently. The pellets were resuspended in 400 µl of DEPC-treated water, extracted once with phenol:chloroform (1:1), extracted with chloroform:isoamyl alcohol (24:1) and precipitated overnight at −20° C. in 40 µl sodium acetate (3.0 M; pH 5.2) and 1.0 ml absolute ethanol. After precipitation, the samples were centrifuged (10000×g; 20 min), washed once with 70% ethanol, air dried for 5-10 minutes and resuspended in 20 µl of DEPC-treated water. RNA concentrations were derived from optical densities.

Total RNA (5 µg in 10.5 µl total volume in DEPC-H$_2$O) was heated at 65° C. for 5 minutes, and then added to tubes containing 4 µl 5× MMLV-RT buffer, 2 µl dNTPS, 2 µl dT17 primer (10 pmol/ml), 0.5 µl RNA sin (40 U/ml) and 1 µl MMLV-RT (200 units/µl). The reactions were incubated at 37° C. for 1 hour. Afterward, the MMLV-RT was inactivated by heating at 95° C. for 5 minutes. The samples were diluted by addition of 80 µl water.

Transcribed samples (5 µl) were subjected to polymerase-chain reaction using standard methodologies (50 µl total volume). Boden, et al., Endocrinology, 138, 2820-2828 (1997); Ausubel, et al., "Quantitation of Rare DNAs by the Polymerase Chain Reaction", Current Protocols in Molecular Biology, Chapter 15.31-1, Wiley & Sons, Trenton, N.J. (1990). Briefly, samples were added to tubes containing water and appropriate amounts of PCR buffer (25 mM MgCl$_2$, dNTPs, forward and reverse primers (for RLMPU; SEQ. ID NOS: 15 and 16), $^{32}$P-dCTP, and DNA polymerase. Primers were designed to run consistently at 22 cycles for radioactive band detection and 33 cycles for amplification of PCR product for use as a screening probe (94° C., 30 sec, 58° C., 30 sec; 72° C., 20 sec).

Sequencing of the agarose gel-purified MG63 osteosarcoma-derived PCR product gave a sequence more than 95% homologous to the RLMPU PCR product. That sequence is designated HLMP unique region (HLMPU; SEQ. ID NO: 6).

Example 17

Screening of Reverse-Transcriptase-Derived MG63 cDNA

Screening was performed with PCR using specific primers (SEQ. ID NOS:16 and 17) as described in Example 7. A 717 base-pair MG63 PCR product was agarose gel purified and sequenced with the given primers (SEQ. ID NOs: 12, 15, 16, 17, 18, 27 and 28). Sequences were confirmed a minimum of two times in both directions. The MG63 sequences were aligned against each other and then against the full-length rat LMP cDNA sequence to obtain a partial human LMP cDNA sequence (SEQ. ID NO: 7).

Example 18

Screening of a Human Heart cDNA Library

Based on Northern blot experiments, it was determined that LMP-1 is expressed at different levels by several different tissues, including human heart muscle. A human heart cDNA library was therefore examined. The library was plated at 5×10$^4$ pfu/ml onto agar plates (LB bottom agar) and plates were grown overnight at 37° C. Filter membranes were overlaid onto the plates for two minutes. Afterward, the filters denatured, rinsed, dried, UV cross-linked and incubated in pre-hyridization buffer (2× PIPES [pH 6.5]; 5% formamide, 1% SDS, 100 g/ml denatured salmon sperm DNA) for 2 h at 42° C. A radio-labeled, LMP-unique, 223 base-pair probe ($^{32}$P, random primer labeling; SEQ ID NO: 6) was added and hybridized for 18 h at 42° C. Following hybridization, the membranes were washed once at room temperature (10 min, 1×SSC, 0.1% SDS) and three times at 55° C. (15 min, 0.1× SSC, 0.1% SDS). Double-positive plaque-purified heart library clones, identified by autoradiography, were rescued as lambda phagemids according to the manufacturers' protocols (Stratagene, La Jolla, Calif.).

Restriction digests of positive clones yielded cDNA inserts of varying sizes. Inserts greater than 600 base-pairs in length were selected for initial screening by sequencing. Those inserts were sequenced by standard methods as described in Example 11.

One clone, number 7, was also subjected to automated sequence analysis using primers corresponding to SEQ. ID NOS: 11-14, 16 and 27. The sequences obtained by these methods were routinely 97-100% homologous. Clone 7 (Partial Human LMP-1 cDNA from a heart library; SEQ. ID NO: 8) contained a sequence that was more than 87% homologous to the rat LMP cDNA sequence in the translated region.

Example 19

Determination of Full-Length Human LMP-1 cDNA

Overlapping regions of the MG63 human osteosarcoma cell cDNA sequence and the human heart cDNA clone 7 sequence were used to align those two sequences and derive a complete human cDNA sequence of 1644 base-pairs. NALIGN, a program in the PCGENE software package, was used to align the two sequences. The overlapping regions of the two sequences constituted approximately 360 base-pairs having complete homology except for a single nucleotide substitution at nucleotide 672 in the MG63 cDNA (SEQ. ID NO: 7) with clone 7 having an "A" instead of a "G" at the corresponding nucleotide 516 (SEQ. ID NO: 8).

The two aligned sequences were joined using SEQIN, another subprogram of PCGENE, using the "G" substitution of the MG63 osteosarcoma cDNA clone. The resulting sequence is shown in SEQ. ID NO: 9. Alignment of the novel human-derived sequence with the rat LMP-1 cDNA was accomplished with NALIGN. The full-length human LMP-1 cDNA sequence (SEQ. ID NO: 9) is 87.3% homologous to the translated portion of rat LMP-1 cDNA sequence.

Example 20

Determination of Amino Acid Sequence of Human LMP-1

The putative amino acid sequence of human LMP-1 was determined with the PCGENE subprogram TRANSL. The open reading frame in SEQ. ID NO: 9 encodes a protein comprising 457 amino acids (SEQ. ID NO: 10). Using the PCGENE subprogram Palign, the human LMP-1 amino acid sequence was found to be 94.1% homologous to the rat LMP-1 amino acid sequence.

Example 21

Determination of the 5 Prime Untranslated Region of the Human LMP cDNA

MG63 5' cDNA was amplified by nested RT-PCR of MG63 total RNA using a 5' rapid amplification of cDNA ends (5' RACE) protocol. This method included first strand cDNA synthesis using a lock-docking oligo (dT) primer with two degenerate nucleotide positions at the 3' end (Chenchik. et al., CLONTECHniques, X:5 (1995); Borson, et al., PC Methods Applic., 2, 144 (1993)). Second-strand synthesis is performed according to the method of Gubler, et al., Gene, 2, 263 (1983), with a cocktail of Escherichia coli DNA polymerase 1, RNase H, and E. coli DNA ligase. After creation of blunt ends with T4 DNA polymerase, double-stranded cDNA was ligated to the fragment (5'-CTAATACGACTCACTATAGGGCTC-GAGCGGCCGCCCGGGCAGGT-3') (SEQ. ID NO: 19). Prior to RACE, the adaptor-ligated cDNA was diluted to a concentration suitable for Marathon RACE reactions (1:50). Adaptor-ligated double-stranded cDNA was then ready to be specifically cloned.

First-round PCR was performed with the adaptor-specific oligonucleotide, 5'-CCATCCTAATACGACTCACTAT-AGGGC-3' (AP1) (SEQ. ID NO: 20) as sense primer and a Gene Specific Primer (GSP) from the unique region described in Example 16 (HLMPU). The second round of PCR was performed using a nested primers GSP1-HLMPU (antisense/reverse primer) (SEQ. ID NO: 23) and GSP2-HLMPUF (SEQ. ID NO: 24) (see Example 16; sense/forward primer). PCR was performed using a commercial kit (Advantage cDNA PCR core kit; CloneTech Laboratories Inc., Palo Alto, Calif.) that utilizes an antibody-mediated, but otherwise standard, hot-start protocol. PCR conditions for MG63 cDNA included an initial hot-start denaturation (94° C., 60 sec) followed by: 94° C., 30 sec; 60° C., 30 sec; 68° C., 4 min; 30 cycles. The firstround PCR product was approximately 750 base-pairs in length whereas the nested PCR product was approximately 230 base-pairs. The first-round PCR product was cloned into linearized pCR 2.1 vector (3.9 Kb). The inserts were sequenced in both directions using M13 Forward and Reverse primers (SEQ. ID NO: 11; SEQ. ID NO: 12).

Example 22

Determination of Full-Length Human LMP-1 cDNA with 5 Prime UTR

Overlapping MG63 human osteosarcoma cell cDNA 5'-UTR sequence (SEQ. ID NO: 21), MG63 717 base-pair sequence (Example 17; SEQ. ID NO: 8) and human heart cDNA clone 7 sequence (Example 18) were aligned to derive a novel human cDNA sequence of 1704 base-pairs (SEQ. ID NO: 22). The alignment was accomplished with NALIGN, (both PCGENE and Omiga 1.0; Intelligenetics). Over-lapping sequences constituted nearly the entire 717 base-pair region (Example 17) with 100% homology. Joining of the aligned sequences was accomplished with SEQIN.

Example 23

Construction of LIM Protein Expression Vector

The construction of pHIS-5ATG LMP-1s expression vector was carried out with the sequences described in Examples 17 and 18. The 717 base-pair clone (Example 17; SEQ. ID NO: 7) was digested with ClaI and EcoRV. A small fragment (~250 base-pairs) was gel purified. Clone 7 (Example 18; SEQ. ID NO: 8) was digested with ClaI and XbaI and a 1400 base-pair fragment was gel purified. The isolated 250 base-pair and 1400 base-pair restriction fragments were ligated to form a fragment of ~1650 base-pairs.

Due to the single nucleotide substitution in Clone 7 (relative to the 717 base-pair PCR sequence and the original rat sequence) a stop codon at translated base-pair 672 resulted. Because of this stop codon, a truncated (short) protein was encoded, hence the name LMP-1s. This was the construct used in the expression vector (SEQ. ID NO: 32). The full length cDNA sequence with 5' UTR (SEQ. ID NO: 33) was created by alignment of SEQ. ID NO: 32 with the 5' RACE sequence (SEQ. ID NO: 21). The amino acid sequence of LMP-1s (SEQ. ID NO: 34) was then deduced as a 223 amino acid protein and confirmed by Western blot (as in Example 15) to run at the predicted molecular weight of ~23.7 kD.

The pHis-ATG vector (InVitrogen, Carlsbad, Calif.) was digested with EcoRV and XbaI. The vector was recovered and the 650 base-pair restriction fragment was then ligated into the linearized pHis-ATG. The ligated product was cloned and amplified. The pHis-ATG-LMP-1s Expression vector, also designated pHIS-A with insert HLMP-1s, was purified by standard methods.

Example 24

Induction of Bone Nodule Formation and Mineralization In Vitro with LMP Expression Vector Rat Calvarial cells were isolated and grown in secondary culture according to Example 1. Cultures were either unstimulated or stimulated with glucocorticoid (GC) as described in Example 1. A modification of the Superfect Reagent (Qiagen, Valencia, Calif.) transfection protocol was used to transfect 3 μg/well of each vector into secondary rat calvarial osteoblast cultures according to Example 25.

Mineralized nodules were visualized by Von Kossa staining, as described in Example 3. Human LMP-1s gene product over expression alone induced bone nodule formation (~203 nodules/well) in vitro. Levels of nodules were approximately 50% of those induced by the GC positive control (~412 nodules/well). Other positive controls included the pHisA-LMP-Rat expression vector (~152 nodules/well) and the pCMV2/LMP-Rat-Fwd Expression vector (~206 nodules/well), whereas the negative controls included the pCMV2/LMP-Rat-Rev. expression vector (~2 nodules/well) and untreated (NT) plates (~4 nodules/well). These data demonstrate that the human cDNA was at least as osteoinductive as the rat cDNA. The effect was less than that observed with GC stimulation, most likely due to sub-optimal doses of Expression vector.

Example 25

LMP-Induced Cell Differentiation In Vitro and In Vivo

The rat LMP cDNA in clone 10-4 (see Example 12) was excised from the vector by double-digesting the clone with NotI and ApaI overnight at 37° C. Vector pCMV2 MCS (InVitrogen, Carlsbad, Calif.) was digested with the same restriction enzymes. Both the linear cDNA fragment from clone 10-4 and pCMV2 were gel purified, extracted and ligated with T4 ligase. The ligated DNA was gel purified, extracted and used to transform E. coli JM109 cells for amplification. Positive agar colonies were picked, digested with NotI and ApaI and the restriction digests were examined by gel electrophoresis. Stock cultures were prepared of positive clones.

A reverse vector was prepared in analogous fashion except that the restriction enzymes used were XbaI and HindIII. Because these restriction enzymes were used, the LMP cDNA fragment from clone 10-4 was inserted into pRc/CMV2 in the reverse (that is, non-translatable) orientation. The recombinant vector produced is designated pCMV2/RLMP.

An appropriate volume of pCMV10-4 (60 nM final concentration is optimal [3 μg]; for this experiment a range of 0-600 nM/well [0-30 μg/well] final concentration is preferred) was resuspended in Minimal Eagle Media (MEM) to 450 μl final volume and vortexed for 10 seconds. Superfect was added (7.5 μl/ml final solution), the solution was vortexed for 10 seconds and then incubated at room temperature for 10 minutes. Following this incubation, MEM supplemented with 10% FBS (1 ml/well; 6 ml/plate) was added and mixed by pipetting.

The resulting solution was then promptly pipetted (1 ml/well) onto washed ROB cultures. The cultures were incubated for 2 hours at 37° C. in a humidified atmosphere containing 5% $CO_2$. Afterward, the cells were gently washed once with sterile PBS and the appropriate normal incubation medium was added.

Results demonstrated significant bone nodule formation in all rat cell cultures which were induced with pCMV10-4. For example, pCMV10-4 transfected cells produced 429 nodules/well. Positive control cultures, which were exposed to Trm, produced 460 nodules/well. In contrast, negative controls, which received no treatment, produced 1 nodule/well. Similarly, when cultures were transfected with pCMV10-4 (reverse), no nodules were observed.

For demonstrating de novo bone formation in vivo, marrow was aspirated from the hind limbs of 4-5 week old normal rats (mu/+; heterozygous for recessive athymic condition). The aspirated marrow cells were washed in alpha MEM, centrifuged, and RBCs were lysed by resuspending the pellet in 0.83% $NH_4Cl$ in 10 mM Tris (pH 7.4). The remaining marrow cells were washed 3× with MEM and transfected for 2 hours with 9 μg of pCMV-LMP-1s (forward or reverse orientation) per $3 \times 10^6$ cells. The transfected cells were then washed 2× with MEM and resuspended at a concentration of $3 \times 10^7$ cells/ml.

The cell suspension (100 μl) was applied via sterile pipette to a sterile 2×5 mm type I bovine collagen disc (Sulzer Orthopaedics, Wheat Ridge, Colo.). The discs were surgically implanted subcutaneously on the skull, chest, abdomen or dorsal spine of 4-5 week old athymic rats (rnu/rnu). The animals were scarified at 3-4 weeks, at which time the discs or surgical areas were excised and fixed in 70% ethanol. The fixed specimens were analyzed by radiography and undecalcified histologic examination was performed on 5 μm thick sections stained with Goldner Trichrome. Experiments were also performed using devitalized (guanidine extracted) demineralized bone matrix (Osteotech, Shrewsbury, N.J.) in place of collagen discs.

Radiography revealed a high level of mineralized bone formation that conformed to the form of the original collagen disc containing LMP-1s transfected marrow cells. No mineralized bone formation was observed in the negative control (cells transfected with a reverse-oriented version of the LMP-1s cDNA that did not code for a translated protein), and absorption of the carrier appeared to be well underway.

Histology revealed new bone trabeculae lined with osteoblasts in the LMP-1s transfected implants. No bone was seen along with partial resorption of the carrier in the negative controls.

Radiography of a further experiment in which 18 sets (9 negative control pCMV-LMP-REV & 9 experimental pCMV-LMP-1s) of implants were added to sites alternating between lumbar and thoracic spine in athymic rats demonstrated 0/9 negative control implants exhibiting bone formation (spine fusion) between vertebrae. All nine of the pCMV-LMP-1s treated implants exhibited solid bone fusions between vertebrae.

Example 26

The Synthesis of pHIS-5' ATG LMP-1s Expression Vector from the Sequences Demonstrated in Examples 2 and 3

The 717 base-pair clone (Example 17) was digested with ClaI and EcoRV (New England Biologicals, city, MA). A small fragment (~250 base pairs) was gel purified. Clone No. 7 (Example 18) was digested with ClaI and XbaI. A 1400 base-pair fragment was gel purified from that digest. The isolated 250 base-pair and 1400 base-pair cDNA fragments were ligated by standard methods to form a fragment of ~1650 bp. The pHis-A vector (InVitrogen) was digested with EcoRV and XbaI. The linearized vector was recovered and ligated to the chimeric 1650 base-pair cDNA fragment. The ligated product was cloned and amplified by standard methods, and the phis-A-5' ATG LMP-1s expression vector, also denominated as the vector pHis-A with insert HLMP-1s, was deposited at the ATCC as previously described.

Example 27

The Induction of Bone Nodule Formation and Mineralization in Vitro with pHis-5' ATG LMP-1s Expression Vector Rat calvarial cells were isolated and grown in secondary culture according to Example 1. Cultures were either unstimulated or stimulated with glucocorticoid (GC) according to Example 1. The cultures were transfected with 3 μg of recombinant pHis-A vector DNA/well as described in Example 25. Mineralized nodules were visualized by Von Kossa staining according to Example 3.

Human LMP-1s gene product overexpression alone (i.e., without GC stimulation) induced significant bone nodule formation (~203 nodules/well) in vitro. This is approximately 50% of the amount of nodules produced by cells lo exposed to the GC positive control (~412 nodules/well). Similar results were obtained with cultures transfected with pHisA-LMP-Rat Expression vector (~152 nodules/well) and pCMV2/LMP-Rat-Fwd (~206 nodules/well). In contrast, the negative control pCMV2/LMP-Rat-Rev yielded (~2 nodules/well), while approximately 4 nodules/well were seen in the untreated plates. These data demonstrate that the human LMP-1 cDNA was at least as osteoinductive as the rat LMP-1 cDNA in this model system. The effect in this experiment was less than that observed with GC stimulation; but in some the effect was comparable.

Example 28

LMP Induces Secretion of a Soluble Osteoinductive Factor

Overexpression of RLMP-1 or HLMP-1s in rat calvarial osteoblast cultures as described in Example 24 resulted in significantly greater nodule formation than was observed in the negative control. To study the mechanism of action of LIM mineralization protein conditioned medium was harvested at different time points, concentrated to 10×, sterile filtered, diluted to its original concentration in medium containing fresh serum, and applied for four days to untransfected cells.

Conditioned media harvested from cells transfected with RLMP-1 or HLMP-1s at day 4 was approximately as effective in inducing nodule formation as direct overexpression of RLMP-1 in transfected cells. Conditioned media from cells transfected with RLMP-1 or HLMP-1 in the reverse orientation had no apparent effect on nodule formation. Nor did conditioned media harvested from LMP-1 transfected cultures before day 4 induce nodule formation. These data suggest that expression of LMP-1 caused the synthesis and/or secretion of a soluble factor, which did not appear in culture medium in effective amounts until 4 days post transfection.

Since overexpression of rLMP-1 resulted in the secretion of an osteoinductive factor into the medium, Western blot analysis was used to determine if LMP-1 protein was present in the medium. The presence of RLMP-1 protein was assessed using antibody specific for LMP-1 (QDPDEE) and detected by conventional means. LMP-1 protein was found only in the cell layer of the culture and not detected in the medium.

Partial purification of the osteoinductive soluble factor was accomplished by standard 25% and 100% ammonium sulfate cuts followed by DE-52 anion exchange batch chromatography (100 mM or 500 mM NACl). All activity was observed in the high ammonium sulfate, high NaCl fractions. Such localization is consistent with the possibility of a single factor being responsible for conditioning the medium.

Example 29

Gene Therapy in Lumbar Spine Fusion Mediated by Low Dose Adenovirus

This study determined the optimal dose of adenoviral delivery of the LMP-1 cDNA (SEQ. ID NO: 2) to promote spine fusion in normal, that is, immune competent, rabbits.

A replication-deficient human recombinant adenovirus was constructed with the LMP-1 cDNA (SEQ. ID NO: 2) driven by a CMV promoter using the Adeno-Quest™ Kit (Quantum Biotechnologies, Inc., Montreal). A commercially available (Quantum Biotechnologies, Inc., Montreal) recombinant adenovirus containing the beta-galactosidase gene was used as a control.

Initially, an in vitro dose response experiment was performed to determine the optimal concentration of adenovirus-delivered LMP-1 ("AdV-LMP-1") to induce bone differentiation in rat calvarial osteoblast cultures using a 60-minute transduction with a multiplicity of infection ("MOI") of 0.025, 0.25, 2.5, or 25 plaque-forming units (pfu) of virus per cell. Positive control cultures were differentiated by a 7-day exposure to $10^9$ M glucocorticoid ("GC"). Negative control cultures were left untreated. On day 14, the number of mineralized bone nodules was counted after von Kossa staining of the cultures, and the level of osteocalcin secreted into the medium (pmol/mL) was measured by radioimmunoassay (mean±SEM).

The results of this experiment are shown in Table 1. Essentially no spontaneous nodules formed in the untreated negative control cultures. The data show that a MOI equal to 0.25 pfu/cell is most effective for osteoinducing bone nodules, achieving a level comparable to the positive control (GC). Lower and higher doses of adenovirus were less effective.

TABLE I

| Out-come | Neg. Ctrl. | GC | Adv-LMP-1 Dose (MOI) | | | |
|---|---|---|---|---|---|---|
| | | | 0.025 | 0.25 | 2.5 | 25 |
| Bone Nodules | 0.5 ± 0.2 | 188 ± 35 | 79.8 ± 13 | 145.1 ± 13 | 26.4 ± 15 | 87.6 ± 2 |
| Osteocalcin | 1.0 ± .1 | 57.8 ± 9 | 28.6 ± 11 | 22.8 ± 1 | 18.3 ± 3 | 26.0 ± 2 |

In vivo experiments were then performed to determine if the optimal in vitro dose was capable of promoting intertransverse process spine fusions in skeletally mature New Zealand white rabbits. Nine rabbits were anesthetized and 3 cc of bone marrow was aspirated from the distal femur through the intercondylar notch using an 18 gauge needle. The buffy coat was then isolated, a 10-minute transduction with AdV-LMP-1 was performed, and the cells were returned to the operating room for implantation. Single level posterolateral lumbar spine arthrodesis was performed with decortication of transverse processes and insertion of carrier (either rabbit devitalized bone matrix or a collagen sponge) containing 8-15 million autologous nucleated buffy coat cells transduced with either AdV-LMP-1 (MOI=0.4) or AdV-BGal (MOI=0.4). Rabbits were euthanized after 5 weeks and spine fusions were assessed by manual palpation, plain x-rays, CT scans, and undecalcified histology.

The spine fusion sites that received AdV-LMP-1 induced solid, continuous spine fusion masses in all nine rabbits. In contrast, the sites receiving AdV-BGal, or a lower dose of AdV-LMP-1 (MOI=0.04) made little or no bone and resulted in spine fusion at a rate comparable to the carrier alone (<40%). These results were consistent as evaluated by manual palpation, CT scan, and histology. Plain radiographs, however, sometimes overestimated the amount of bone that was present, especially in the control sites. LMP-1 cDNA delivery and bone induction was successful with both of the carrier materials tested. There was no evidence of systemic or local immune response to the adenovirus vector.

These data demonstrate consistent bone induction in a previously validated rabbit spine fusion model which is quite challenging. Furthermore, the protocol of using autogenous bone marrow cells with intraoperative ex vivo gene transduction (10 minutes) is a more clinically feasible procedure than other methods that call for overnight transduction or cell expansion for weeks in culture. In addition, the most effective dose of recombinant adenovirus (MOI=0.25) was substantially lower than doses reported in other gene therapy applications (MOI 40-500). We believe this is due to the fact that LMP-1 is an intracellular signaling molecule and may have powerful signal amplification cascades. Moreover, the observation that the same concentration of AdV-LMP-1 that induced bone in cell culture was effective in vivo was also surprising given the usual required increase in dose of other growth factors when translating from cell culture to animal experiments. Taken together, these observations indicate that local gene therapy using adenovirus to deliver the LMP-1 cDNA is possible and the low dose required will likely minimize the negative effects of immune response to the adenovirus vector.

Example 30

Use of Peripheral Venous Blood Nucleated Cells (Buffy Coat) for Gene Therapy With LMP-1 cDNA to Make Bone In four rabbits we performed spine fusion surgery as above (Example 29) except the transduced cells were the buffy coat from venous blood rather than bone marrow. These cells were transfected with Adeno-LMP or pHIS-LMP plasmid and had equivalent successful results as when bone marrow cells were used. This discovery of using ordinary venous blood cells for gene delivery makes gene therapy more feasible clinically since it avoids painful marrow harvest under general anesthesia and yields two times more cells per mL of starting material.

Example 31

Isolation of Human LMP-1 Splice Variants

Intron/Exon mRNA transcript splice variants are a relatively common regulatory mechanism in signal-transduction and cellular/tissue development. Splice variants of various genes have been shown to alter protein-protein, protein-DNA, protein-RNA, and protein-substrate interactions. Splice variants may also control tissue specificity for gene expression allowing different forms (and therefore functions) to be expressed in various tissues. Splice variants are a common regulatory phenomenon in cells. It is possible that the LMP splice variants may result in effects in other tissues such as nerve regeneration, muscle regeneration, or development of other tissues.

To screen a human heart cDNA library for splice variants of the HLMP-1 sequence, a pair of PCR primer corresponding to sections of SEQ. ID NO: 22 was prepared. The forward PCR primer, which was synthesized using standard techniques, corresponds to nucleotides 35-54 of SEQ. ID NO: 22. It has the following sequence:

5' GAGCCGGCATCATGGATTCC 3' (SEQ. ID NO: 35)

The reverse PCR primer, which is the reverse complement of nucleotides 820-839 in SEQ. ID NO: 22, has the following sequence:

5' GCTGCCTGCACAATGGAGGT 3' (SEQ. ID NO: 36)

The forward and reverse PCR primers were used to screen human heart cDNA (ClonTech, Cat No. 7404-1) for sequences similar to HLMP-1 by standard techniques, using a cycling protocol of 94° C. for 30 seconds, 64° C. for 30 seconds, and 72° C. for 1 minute, repeated 30 times and followed by a 10 minute incubation at 72° C. The amplification cDNA sequences were gel-purified and submitted to the Emory DNA Sequence Core Facility for sequencing. The clones were sequenced using standard techniques and the sequences were examined with PCGENE (intelligenetics; Programs SEQUIN and NALIGN) to determine homology to SEQ. ID NO: 22. Two homologous nucleotide sequences with putative alternative splice sites compared to SEQ. ID NO: 22 were then translated to their respective protein products with Intelligenetic's program TRANSL.

One of these two novel human cDNA sequences (SEQ. ID NO: 37) comprises 1456 bp:

```
CGACGCAGAG CAGCGCCCTG GCCGGGCCAA GCAGGAGCCG GCATCATGGA TTCCTTCAAG    60

GTAGTGCTGG AGGGGCCAGC ACCTTGGGGC TTCCGGCTGC AAGGGGGCAA GGACTTCAAT   120

GTGCCCCTCT CCATTTCCCG GCTCACTCCT GGGGGCAAAG CGGCGCAGGC CGGAGTGGCC   180

GTGGGTGACT GGGTGCTGAG CATCGATGGC GAGAATGCGG GTAGCCTCAC ACACATCGAA   240

GCTCAGAACA AGATCCGGGC CTGCGGGGAG CGCCTCAGCC TGGGCCTCAG CAGGGCCCAG   300
                                          X                   X
CCGGTTCAGA GCAAACCGCA GAAGGTGCAG ACCCCTGACA AACAGCCGCT CCGACCGCTG   360
```

```
GTCCCAGATG CCAGCAAGCA GCGGCTGATG GAGAACACAG AGGACTGGCG GCCGCGGCCG   420

GGGACAGGCC AGTCGCGTTC CTTCCGCATC CTTGCCCACC TCACAGGCAC CGAGTTCATG   480

CAAGACCCGG ATGAGGAGCA CCTGAAGAAA TCAAGCCAGG TGCCCAGGAC AGAAGCCCCA   540

GCCCCAGCCT CATCTACACC CCAGGAGCCC TGGCCTGGCC CTACCGCCCC CAGCCCTACC   600

AGCCGCCCGC CCTGGGCTGT GGACCCTGCG TTTGCCGAGC GCTATGCCCC GGACAAAACG   660

AGCACAGTGC TGACCCGGCA CAGCCAGCCG GCCACGCCCA CGCCGCTGCA GAGCCGCACC   720

TCCATTGTGC AGGCAGCTGC CGGAGGGGTG CCAGGAGGGG GCAGCAACAA CGGCAAGACT   780

CCCGTGTGTC ACCAGTGCCA CAAGGTCATC CGGGGCCGCT ACCTGGTGGC GTTGGGCCAC   840

GCGTACCACC CGGAGGAGTT TGTGTGTAGC CAGTGTGGGA AGGTCCTGGA AGAGGGTGGC   900

TTCTTTGAGG AGAAGGGCGC CATCTTCTGC CCACCATGCT ATGACGTGCG CTATGCACCC   960

AGCTGTGCCA AGTGCAAGAA GAAGATTACA GGCGAGATCA TGCACGCCCT GAAGATGACC  1020

TGGCACGTGC ACTGCTTTAC CTGTGCTGCC TGCAAGACGC CCATCCGGAA CAGGGCCTTC  1080

TACATGGAGG AGGGCGTGCC CTATTGCGAG CGAGACTATG AGAAGATGTT TGGCACGAAA  1140

TGCCATGGCT GTGACTTCAA GATCGACGCT GGGGACCGCT TCCTGGAGGC CCTGGGCTTC  1200

AGCTGGCATG ACACCTGCTT CGTCTGTGCG ATATGTCAGA TCAACCTGGA AGGAAAGACC  1260

TTCTACTCCA AGAAGGACAG GCCTCTCTGC AAGAGCCATG CCTTCTCTCA TGTGTGAGCC  1320

CCTTCTGCCC ACAGCTGCCG CGGTGGCCCC TAGCCTGAGG GGCCTGGAGT CGTGGCCCTG  1380

CATTTCTGGG TAGGGCTGGC AATGGTTGCC TTAACCCTGG CTCCTGGCCC GAGCCTGGGC  1440

TCCCGGGCCC TGCCCA                                                 1456
```

Reading frame shifts caused by the deletion of a 119 bp fragment (between X) and the addition of a 17 bp fragment (underlined) results in a truncated gene product having the following derived amino acid sequence (SEQ. ID NO: 38):

```
Met Asp Ser Phe Lys Val Leu Glu Gly Pro Ala Pro Trp Gly Phe
 1               5                  10                  15

Arg Leu Gln Gly Gly Lys Asp Phe Asn Val Pro Leu Ser Ile Ser Arg
                 20                  25                  30

Leu Thr Pro Gly Gly Lys Ala Ala Gln Ala Gly Val Ala Val Gly Asp
             35                  40                  45

Trp Val Leu Ser Ile Asp Gly Glu Asn Ala Gly Ser Leu Thr His Ile
         50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Asn Lys Pro Gln Lys Val Gln Thr
                     85                  90                  95

Pro Asp Lys Gln Pro Leu Arg Pro Leu Val Pro Asp Ala Ser Lys Gln
                100                 105                 110

Arg Leu Met Glu Asn Thr Glu Asp Trp Arg Pro Arg Pro Gly Thr Gly
             115                 120                 125

Gln Ser Arg Ser Phe Arg Ile Leu Ala His Leu Thr Gly Thr Glu Phe
     130                 135                 140

Met Gln Asp Pro Asp Glu Glu His Leu Lys Lys Ser Ser Gln Val Pro
145                 150                 155                 160

Arg Thr Glu Ala Pro Ala Pro Ala Ser Ser Thr Pro Gln Glu Pro Trp
                 165                 170                 175

Pro Gly Pro Thr Ala Pro Ser Pro Thr Ser Arg Pro Pro Trp Ala Val
                 180                 185                 190
```

-continued

```
Asp Pro Ala Phe Ala Glu Arg Tyr Ala Pro Asp Lys Thr Ser Thr Val
        195                 200                 205
Leu Thr Arg His Ser Gln Pro Ala Thr Pro Thr Pro Leu Gln Ser Arg
    210                 215                 220
Thr Ser Ile Val Gln Ala Ala Ala Gly Gly Val Pro Gly Gly Gly Ser
225                 230                 235                 240
Asn Asn Gly Lys Thr Pro Val Cys His Gln Cys His Gln Val Ile Arg
                245                 250                 255
Ala Arg Tyr Leu Val Ala Leu Gly His Ala Tyr His Pro Glu Glu Phe
            260                 265                 270
Val Cys Ser Gln Cys Gly Lys Val Leu Glu Glu Gly Gly Phe Phe Glu
        275                 280                 285
Glu Lys Gly Ala Ile Phe Cys Pro Pro Cys Tyr Asp Val Arg Tyr Ala
    290                 295                 300
Pro Ser Cys Ala Lys Cys Lys Lys Ile Thr Gly Glu Ile Met His
305                 310                 315                 320
Ala Leu Lys Met Thr Trp His Val Leu Cys Phe Thr Cys Ala Ala Cys
                325                 330                 335
Lys Thr Pro Ile Arg Asn Arg Ala Phe Tyr Met Glu Glu Gly Val Pro
            340                 345                 350
Tyr Cys Glu Arg Asp Tyr Glu Lys Met Phe Gly Thr Lys Cys Gln Trp
        355                 360                 365
Cys Asp Phe Lys Ile Asp Ala Gly Asp Arg Phe Leu Glu Ala Leu Gly
    370                 375                 380
Phe Ser Trp His Asp Thr Cys Phe Val Cys Ala Ile Cys Gln Ile Asn
385                 390                 395                 400
Leu Glu Gly Lys Thr Phe Tyr Ser Lys Lys Asp Arg Pro Leu Cys Lys
                405                 410                 415
Ser His Ala Phe Ser His Val
                420
```

This 423 amino acid protein demonstrates 100% homology to the protein shown in SEQ. ID NO. 10, except for the sequence in the highlighted area (amino acids 94-99), which are due to the nucleotide changes depicted above.

The second novel human heart cDNA sequence (SEQ. ID NO: 39) comprises 1575 bp:

```
CGACGCAGAG CAGCGCCCTG GCCGGGCCAA GCAGGAGCCG GCATCATGGA TTCCTTCAAG    60

GTAGTGCTGG AGGGGCCAGC ACCTTGGGGC TTCCGGCTGC AAGGGGGCAA GGACTTCAAT   120

GTGCCCCTCT CCATTTCCCG GCTCACTCCT GGGGGCAAAG CGGCGCAGGC CGGAGTGGCC   180

GTGGGTGACT GGGTGCTGAG CATCGATGGC GAGAATGCGG GTAGCCTCAC ACACATCGAA   240

GCTCAGAACA AGATCCGGGC CTGCGGGGAG CGCCTCAGCC TGGGCCTCAG CAGGGCCCAG   300

CCGGTTCAGA GCAAACCGCA GAAGGCCTCC GCCCCCGCCG CGGACCCTCC GCGGTACACC   360

TTTGCACCCA GCGTCTCCCT CAACAAGACG GCCCGGCCCT TGGGGCGCC CCCGCCCGCT    420

GACAGCGCCC CGCAACAGAA TGGGTGCAGA CCCCTGACAA ACAGCCGCTC CGAC-        480
CGCTGG

TCCCAGATGC CAGCAAGCAG CGGCTGATGG AGAACACAGA GGACTGGCGG CCGCGGCCGG   540

GGACAGGCCA GTCGCGTTCC TTCCGCATCC TTGCCCACCT CACAGGCACC GAGTTCATGC   600

AAGACCCGGA TGAGGAGCAC CTGAAGAAAT CAAGCCAGGT GCCCAGGACA GAAGCCCCAG   660

CCCCAGCCTC ATCTACACCC CAGGAGCCCT GGCCTGGCCC TACCGCCCCC AGCCCTACCA   720
```

```
GCCGCCCGCC CTGGGCTGTG GACCCTGCGT TTGCCGAGCG CTATGCCCCG GACAAAACGA    780

GCACAGTGCT GACCCGGCAC AGCCAGCCGG CCACGCCCAC GCCGCTGCAG AGCCGCACCT    840

CCATTGTGCA GGCAGCTGCC GGAGGGGTGC CAGGAGGGGG CAGCAACAAC GGCAAGACTC    900

CCGTGTGTCA CCAGTGCCAC AAGGTCATCC GGGGCCGCTA CCTGGTGGCG TTGGGCCACG    960

CGTACCACCC GGAGGAGTTT GTGTGTAGCC AGTGTGGGAA GGTCCTGGAA GAGGGTGGCT   1020

TCTTTGAGGA GAAGGGCGCC ATCTTCTGCC CACCATGCTA TGACGTGCGC TATGCACCCA   1080

GCTGTGCCAA GTGCAAGAAG AAGATTACAG GCGAGATCAT GCACGCCCTG AAGATGACCT   1140

GGCACGTGCA CTGCTTTACC TGTGCTGCCT GCAAGACGCC CATCCGGAAC AGGGCCTTCT   1200

ACATGGAGGA GGGCGTGCCC TATTGCGAGC GAGACTATGA GAAGATGTTT GGCACGAAAT   1260

GCCATGGCTG TGACTTCAAG ATCGACGCTG GGGACCGCTT CCTGGAGGCC CTGGGCTTCA   1320

GCTGGCATGA CACCTGCTTC GTCTGTGCGA TATGTCAGAT CAACCTGGAA GGAAAGACCT   1380

TCTACTCCAA GAAGGACAGG CCTCTCTGCA AGAGCCATGC CTTCTCTCAT GTGTGAGCCC   1440

CTTCTGCCCA CAGCTGCCGC GGTGGCCCCT AGCCTGAGGG GCCTGGAGTC GTGGCCCTGC   1500

ATTTCTGGGT AGGGCTGGCA ATGGTTGCCT TAACCCTGGC TCCTGGCCCG AGCCTGGGCT   1560

CCCGGGCCCT GCCCA                                                   1575
```

Reading frame shifts caused by the addition of a 17 bp fragment (bolded, italicized and underlined) results in an early translation stop codon at position 565-567 (underlined).

The derived amino acid sequence (SEQ. ID NO: 40) consists of 153 amino acids:

```
Met Asp Ser Phe Lys Val Val Leu Glu Gly Pro Ala Pro Trp Gly Phe
  1               5                  10                  15

Arg Leu Gln Gly Gly Lys Asp Phe Asn Val Pro Leu Ser Ile Ser Arg
               20                  25                  30

Leu Thr Pro Gly Gly Lys Ala Ala Gln Ala Gly Val Ala Val Gly Asp
           35                  40                  45

Trp Val Leu Ser Ile Asp Gly Glu Asn Ala Gly Ser Leu Thr His Ile
     50                  55                  60

Glu Ala Gln Asn Lys Ile Arg Ala Cys Gly Glu Arg Leu Ser Leu Gly
 65                  70                  75                  80

Leu Ser Arg Ala Gln Pro Val Gln Ser Lys Pro Gln Lys Ala Ser Ala
                 85                  90                  95

Pro Ala Ala Asp Pro Pro Arg Tyr Thr Phe Ala Pro Ser Val Ser Leu
                100                 105                 110

Asn Lys Thr Ala Arg Pro Phe Gly Ala Pro Pro Ala Asp Ser Ala
            115                 120                 125

Pro Gln Gln Asn Gly Cys Arg Pro Leu Thr Asn Ser Arg Ser Asp Arg
            130                 135                 140

Trp Ser Gln Met Pro Ala Ser Ser Gly
145                 150
```

This protein demonstrates 100% homology to SEQ. ID NO: 10 until amino acid 94, where the addition of the 17 bp fragment depicted in the nucleotide sequence results in a frame shift. Over amino acids 94-153, the protein is not homologous to SEQ. ID NO: 10. Amino acids 154-457 in SEQ. ID NO: 10 are not present due to the early stop codon depicted in nucleotide sequence.

Example 32

Genomic HLMP-1 Nucleotide Sequence

Applicants have identified the genomic DNA sequence encoding HLMP-1, including putative regulatory elements associated with HLMP-1 expression. The entire genomic sequence is shown in SEQ. ID. NO: 41. This sequence was derived from AC023788 (clone RP11-564G9), Genome Sequencing Center, Washington University School of Medicine, St. Louis, Mo.

The putative promoter region for HLMP-1 spans nucleotides 2,660-8,733 in SEQ. ID NO: 41. This region comprises, among other things, at least ten potential glucocorticoid response elements ("GREs") (nucleotides 6148-6153, 6226-6231, 6247-6252, 6336-6341, 6510-6515, 6552-6557, 6727-6732, 6752-6757, 7738-7743, and 8255-8260), twelve potential Sma-2 homologues to Mothers against Drosophilla decapentaplegic ("SMAD") binding element sites (nucleotides 3569-3575, 4552-4558, 4582-4588, 5226-5232, 6228-6234, 6649-6655, 6725-6731, 6930-6936, 7379-7384, 7738-7742, 8073-8079, and 8378-8384), and three TATA boxes (nucleotides 5910-5913, 6932-6935, and 7380-7383). The three TATA boxes, all of the GREs, and eight of the SMAD binding elements ("SBEs") are grouped in the region spanning nucleotides 5,841-8,733 in SEQ. ID NO: 41. These regulatory elements can be used, for example, to regulate expression of exogenous nucleotide sequences encoding proteins involved in the process of bone formation. This would permit systemic administration of therapeutic factors or genes relating to bone formation and repair, as well as factors or genes associated with tissue differentiation and development.

In addition to the putative regulatory elements, 13 exons corresponding to the nucleotide sequence encoding HLMP-1 have been identified. These exons span the following nucleotides in SEQ. ID NO: 41:

| Exon 1  | 8733-8767   |
|---------|-------------|
| Exon 2  | 9790-9895   |
| Exon 3  | 13635-13787 |
| Exon 4  | 13877-13907 |
| Exon 5  | 14387-14502 |
| Exon 6  | 15161-15297 |
| Exon 7  | 15401-15437 |
| Exon 8  | 16483-16545 |
| Exon 9  | 16689-16923 |
| Exon 10 | 18068-18248 |
| Exon 11 | 22117-22240 |
| Exon 12 | 22323-22440 |
| Exon 13 | 22575-22911 |

In HLMP-2 there is another exon (Exon 5A), which spans nucleotides 14887-14904.

Expression of HLMP-1 in Intervertebral Disc Cells

LIM mineralization protein-1 (LMP-1) is an intracellular protein that can direct cellular differentiation in osseous and non-osseous tissues. This example demonstrates that expressing human LMP-1 ("HLMP-1") in intervertebral disc cells increases proteoglycan synthesis and promotes a more chondrocytic phenotype. In addition, the effect of HLMP-1 expression on cellular gene expression was demonstrated by measuring Aggrecan and BMP-2 gene expression. Lumbar intervertebral disc cells were harvested from Sprague-Dawley rats by gentle enzymatic digestion and cultured in monolayer in DMEM/F12 supplemented with 10% FBS. These cells were then split into 6 well plates at approximately 200,000 cells per well and cultured for about 6 days until the cells reached approximately 300,000 cells per well. The culture media was changed to 1% FBS DMEM/F12 and this was considered Day 0.

Replication deficient Type 5 adenovirus comprising a HLMP-1 cDNA operably linked to a cytomegalovirus ("CMV") promoter has been previously described, for example, in U.S. Pat. No. 6,300,127. The negative control adenovirus was identical except the HLMP-1 cDNA was replaced by LacZ cDNA. For a positive control, uninfected cultures were incubated in the continuous presence of BMP-2 at a concentration of 100 nanograms/milliliter.

On Day 0, the cultures were infected with adenovirus for 30 minutes at 37° C. in 300 microliters of media containing 1% FBS. Fluorescence Activated Cell Sorter ("FACS") analysis of cells treated with adenovirus containing the green fluorescent protein ("GFP") gene ("AdGFP") was performed to determine the optimal dose range for expression of transgene. The cells were treated with adenovirus containing the human LMP-1 cDNA (AdHLMP-1) (at MOIs of 0, 100, 300, 1000, or 3000) or with adenovirus containing the LacZ marker gene (AdLacZ MOI of 1000) (negative control). The culture media was changed at day 3 and day 6 after infection.

Proteoglycan production was estimated by measuring the sulfated glycosaminoglycans (sGAG) present in the culture media (at day 0, 3, and 6) using a di-methyl-methylene blue ("DMMB") calorimetric assay.

For quantification of Aggrecan and BMP-2 mRNA, cells were harvested at day 6 and the mRNA extracted by the Trizol technique. The mRNA was converted to cDNA using reverse-transcriptase and used for real-time PCR, which allowed the relative abundance of Aggrecan and BMP-2 message to be determined. Real time primers were designed and tested for Aggrecan and BMP-2 in previous experiments. The Cyber-green technique was used. Standardization curves were used to quantitate mRNA abundance.

For transfected cells, cell morphology was documented with a light microscope. Cells became more rounded with AdHLMP-1 (MOI 1000) treatment, but not with AdLacZ treatment. AdLacZ infection did not significantly change cell morphology.

FACS analysis of rat disc cells infected with ADGFP at MOI of 1000 showed the highest percentage cells infected (45%).

There was a dose dependent increase between sGAG production and AdhLMP-1 MOI. These data are seen in FIG. 1, which shows the production of sGAG after over-expressing HLMP-1 at different MOIs in rat disc cells in monolayer cultures. The results have been normalized to day 0 untreated cells. Error bars represent the standard error of the mean. As shown in FIG. 1, the sGAG production observed at day 3 was relatively minor, indicating a lag time between transfection and cellular production of GAG. Treatment with AdLacZ did not significantly change the sGAG production. As also shown in FIG. 1, the optimal dose of AdhLMP-1 was at a MOI of 1000, resulting in a 260% enhancement of sGAG production over the untreated controls at day 6. Higher or lower doses of AdhLMP-1 lead to a diminished response.

Figure 2:
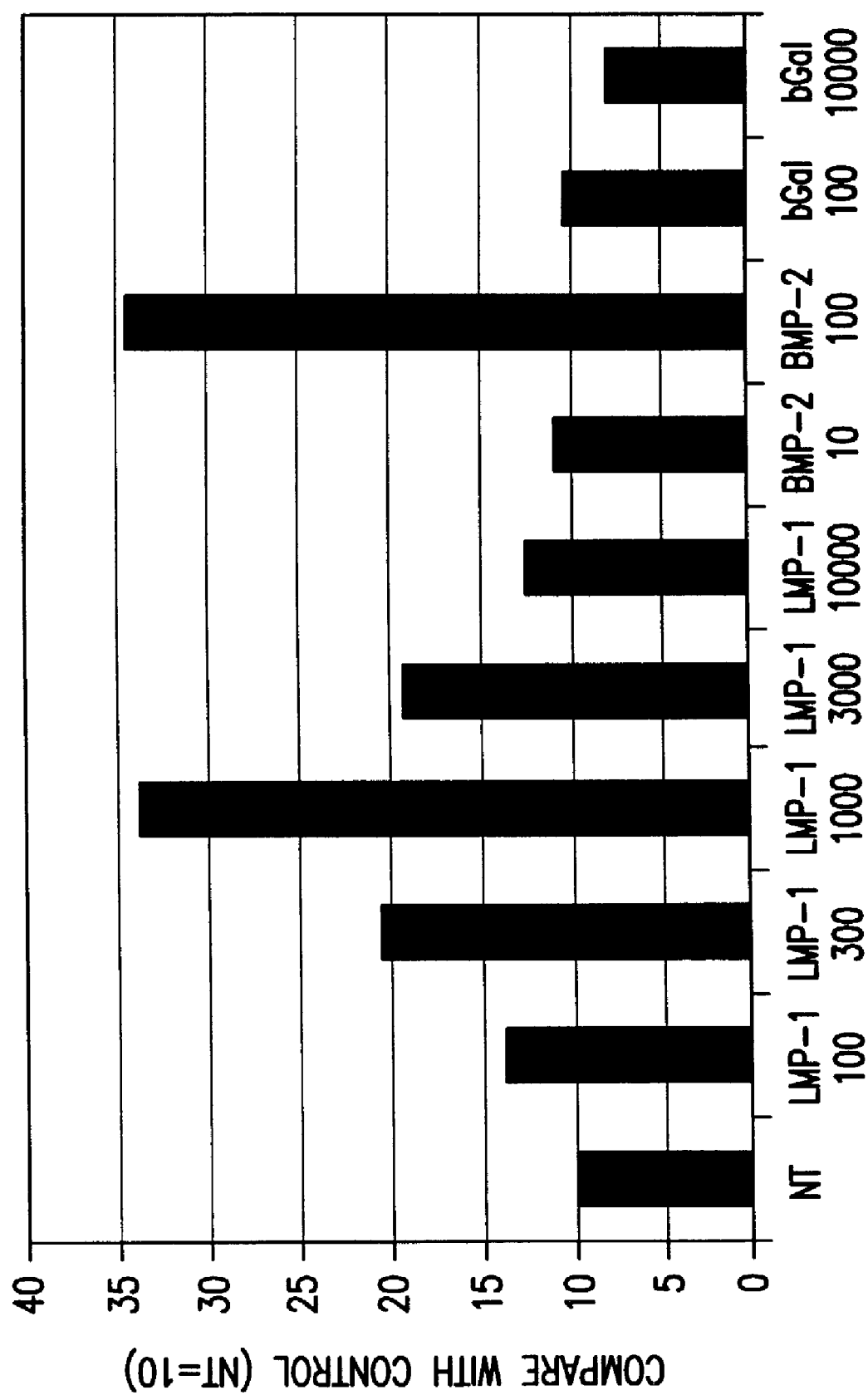
FIG. 2 is a chart showing the dose response of rat intervertebral disc cells six days after infection with different MOI of AdHLMP-1.

The effect of AdhLMP-1 dosage (M01) on sGAG production is further illustrated in FIG. 2. FIG. 2 is a chart showing rat disc sGAG levels at day 6 after treatment with AdhLMP-1 at different MOIs. As can be seen from FIG. 2, the optimal dose of AdhLMP-1 was at a MOI of 1000.

Figure 3:
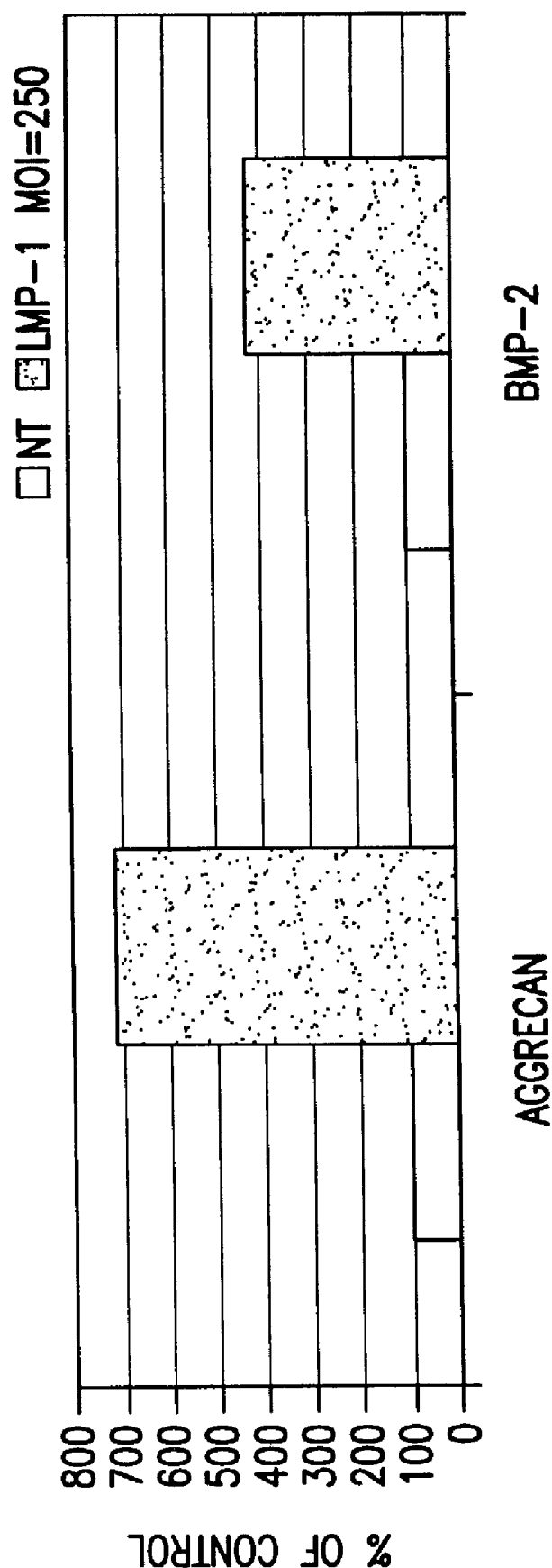
FIG. 3 is a chart showing the expression of Aggrecan and BMP-2 mRNA by AdHLMP-1 transfected rat intervertebral disc cells six days following transfection with an MOI of 250 virions/cell.

Aggrecan and BMP-2 mRNA production is seen in FIG. 3. This figure demonstrates the increase in Aggrecan and BMP-2 mRNA after over-expression of HLMP-1. Real-time PCR of mRNA extracted from rat disc cells at day 6 was performed comparing the no-treatment ("NT") cells with cells treated with ADhLMP-1 at a MOI of 250. The data in FIG. 3 are represented as a percentage increase over the untreated sample. As illustrated in FIG. 3, a significant increase in Aggrecan and BMP-2 mRNA was noted following AdhLMP-1 treatment. The increase in BMP-2 expression suggests that BMP-2 is a down-stream gene that mediates HLMP-1 stimulation of proteoglycan synthesis.

These data demonstrate that transfection with AdhLMP-1 is effective in increasing proteoglycan synthesis of intervertebral disc cells. The dose of virus leading to the highest transgene expression (MOI 1000) also leads to the highest induction of sGAG, suggesting a correlation between HLMP-1 expression and sGAG induction. These data indicate that HLMP-1 gene therapy is a method of increasing proteoglycan synthesis in the intervertebral disc, and that HLMP-1 is a agent for treating disc disease.

Figure 4A:
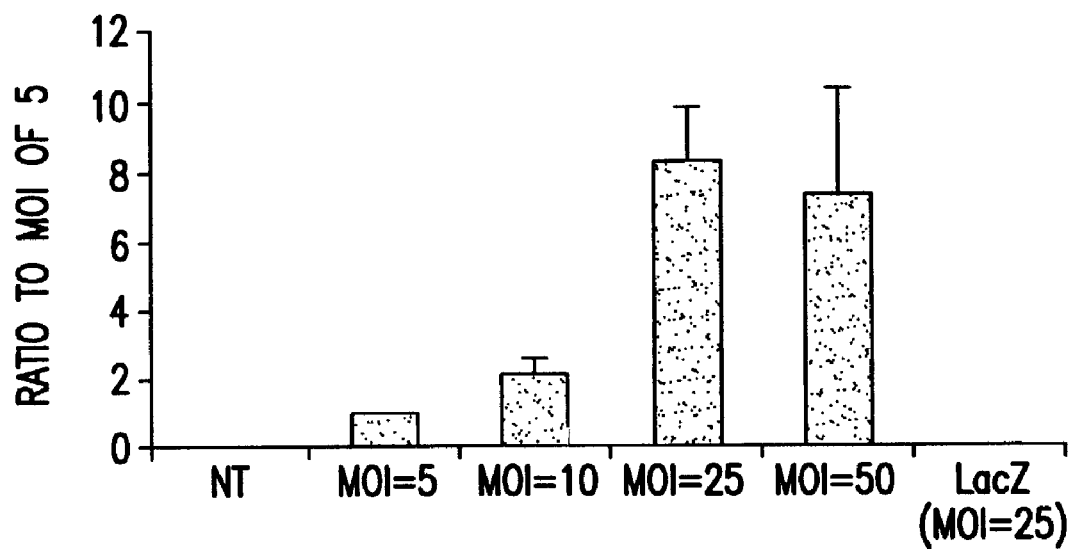
FIG. 4A is a chart showing HLMP-1 mRNA expression 12 hours after infection with Ad-hLMP-1 at different MOIs.

FIG. 4A is a chart showing HLMP-1 mRNA expression 12 hours after infection with Ad-hLMP-1 at different MOIs. In FIG. 4A, exogenous LMP-1 expression was induced with different doses (MOI) of the Ad-hLMP-1 virus and quantitated with realtime PCR. The data is normalized to HLMP-1 mRNA levels from Ad-LMP-1 MOI 5 for comparison purposes. No HLMP-1 was detected in negative control groups, the no-treatment ("NT") or Ad-LacZ treatment ("LacZ"). HLMP-1 mRNA levels in a dose dependent fashion to reach a plateau of approximately 8 fold with a MOI of 25 and 50.

Figure 4B:
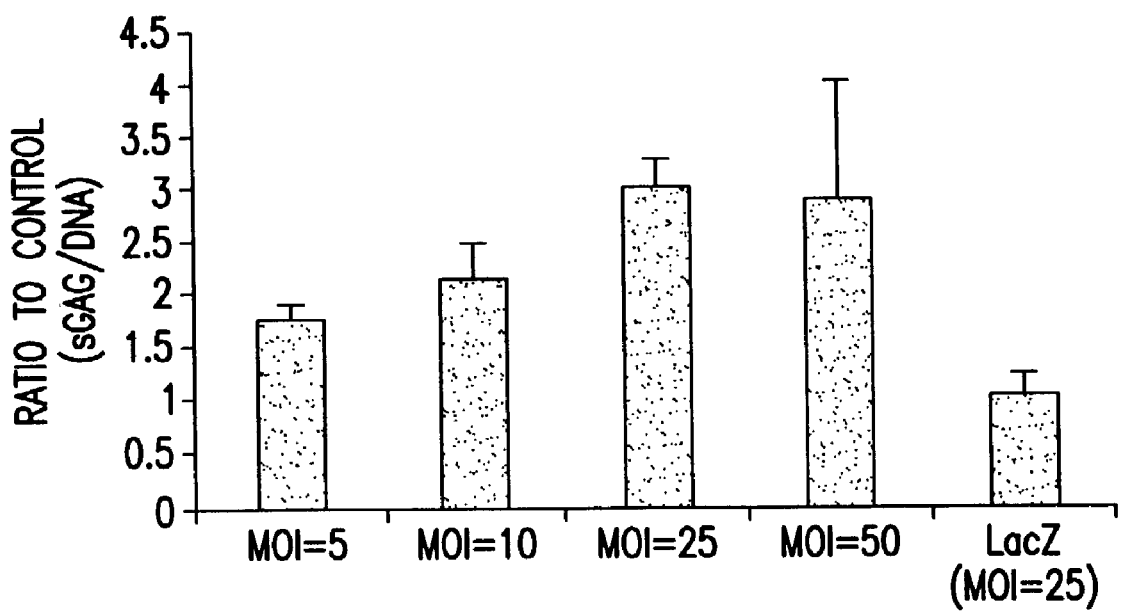
FIG. 4B is a chart showing the production of sGAG in medium from 3 to 6 days after infection.

FIG. 4B is a chart showing the production of sGAG in medium from 3 to 6 days after infection. DMMB assay was used to quantitate total sGAG production between days 3 to 6 after infection. The data in FIG. 4B is normalized to the control (i.e., no treatment) group. As can be seen from FIG. 4B, there was a dose dependent increase in sGAG. with the peak of approximately three fold increase above control reached with a MOI of 25 and 50. The negative control, Ad-LacZ at a MOI of 25, lead to no increase in sGAG. In FIG. 4B, each result is expressed as mean with SD for three samples.

Figure 5:
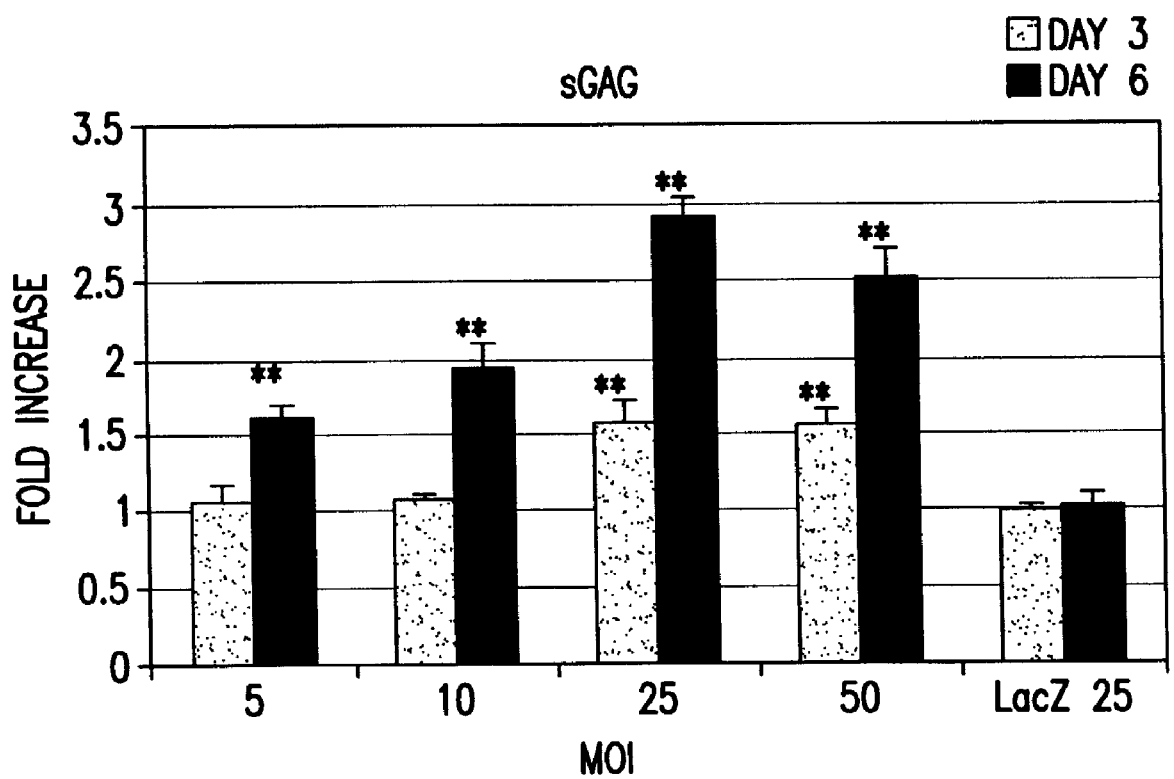
FIG. 5 is a chart showing time course changes of the production of sGAG.

FIG. 5 is a chart showing time course changes of the production of sGAG. As can be seen from FIG. 5, on day 3 sGAG production increased significantly at a MOI of 25 and 50. On day 6 there was a dose dependent increase in sGAG production in response to AdLMP-1. The plateau level of sGAG increase was achieved at a MOI of 25. As can also be seen from FIG. 5, treatment with AdLacZ ("LacZ") did not significantly change the sGAG production. Each result is expressed as mean with SD for six to nine samples. In FIG. 5, "**" indicates data points for which the P value is <0.01 versus the untreated control.

Figure 6A:
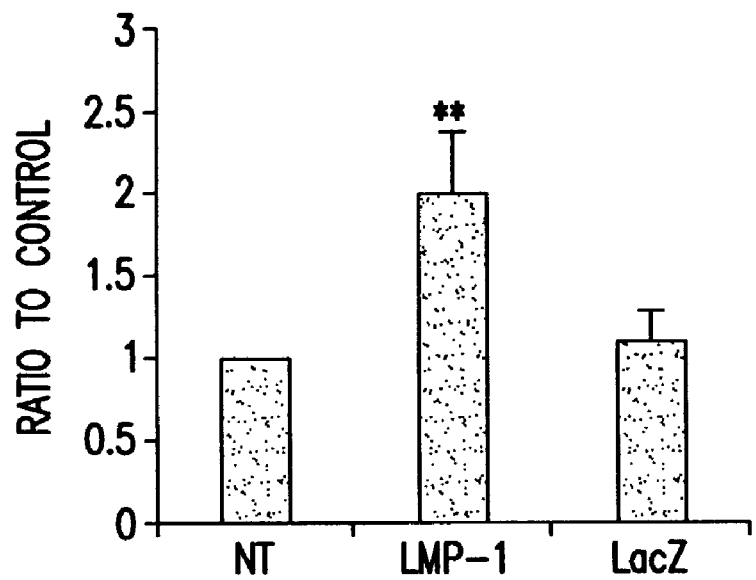
FIG. 6A is a chart showing gene response to LMP-1 over-expression in rat annulus fibrosus cells for aggrecan
Figure 6B:
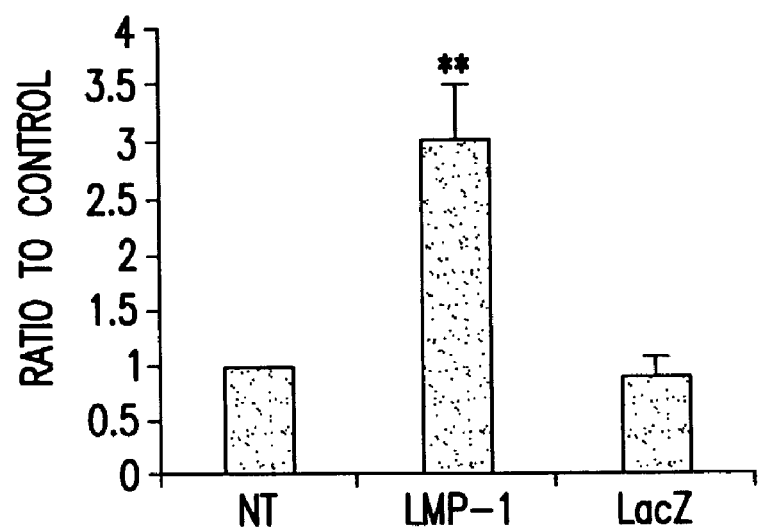
FIG. 6B is a chart showing gene response to LMP-1 over-expression in rat annulus fibrosus cells for BMP-2.

FIGS. 6A and 6B are charts showing gene response to LMP-1 over-expression in rat annulus fibrosus cells for aggrecan and BMP-2, respectively. Quantitative realtime PCR was performed on day 3 after infection with Ad-LMP-1 ("LMP-1") at a MOI of 25. As can be seen from FIGS. 6A and 6B, the gene expression of aggrecan and BMP-2 increased significantly after infection with Ad-LMP-1 compared to the untreated control ("NT"). Further, treatment with AdLacZ ("LacZ") at a MOI of 25 did not significantly change the gene expression of either aggrecan or BMP-2 compared to the untreated control. In FIGS. 6A and 6B, each result is expressed as mean with SD for six samples. In FIGS. 6A and 6B, "**" indicates data points for which the P value is P<0.01.

Figure 7:
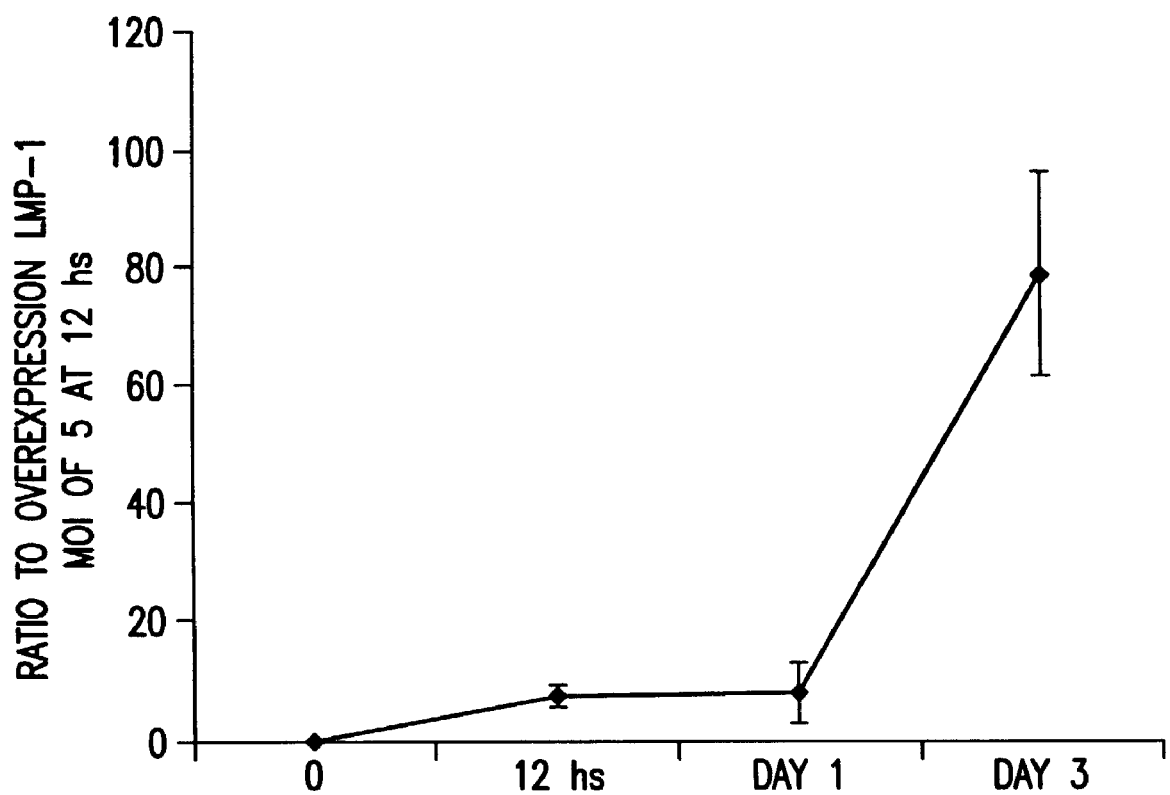
FIG. 7 is a graph showing the time course of HLMP-1 mRNA levels in rat annulus fibrosus cells after infection with AdLMP-1 at MOI of 25.

FIG. 7 is a graph showing the time course of HLMP-1 mRNA levels in rat annulus fibrosus cells after infection with AdLMP-1 at a MOI of 25. The data is expressed as a fold increase above a MOI of 5 of AdLMP-1 after standardization using 18S and replication coefficient of over-expression LMP-1 primer. As can be seen from FIG. 7, HLMP-1 mRNA was upregulated significantly as early as 12 hours after infection. Further, there was a marked increase of expression levels between day 1 and day 3. Each result in FIG. 7 is expressed as mean with SD for six samples.

Figure 8:
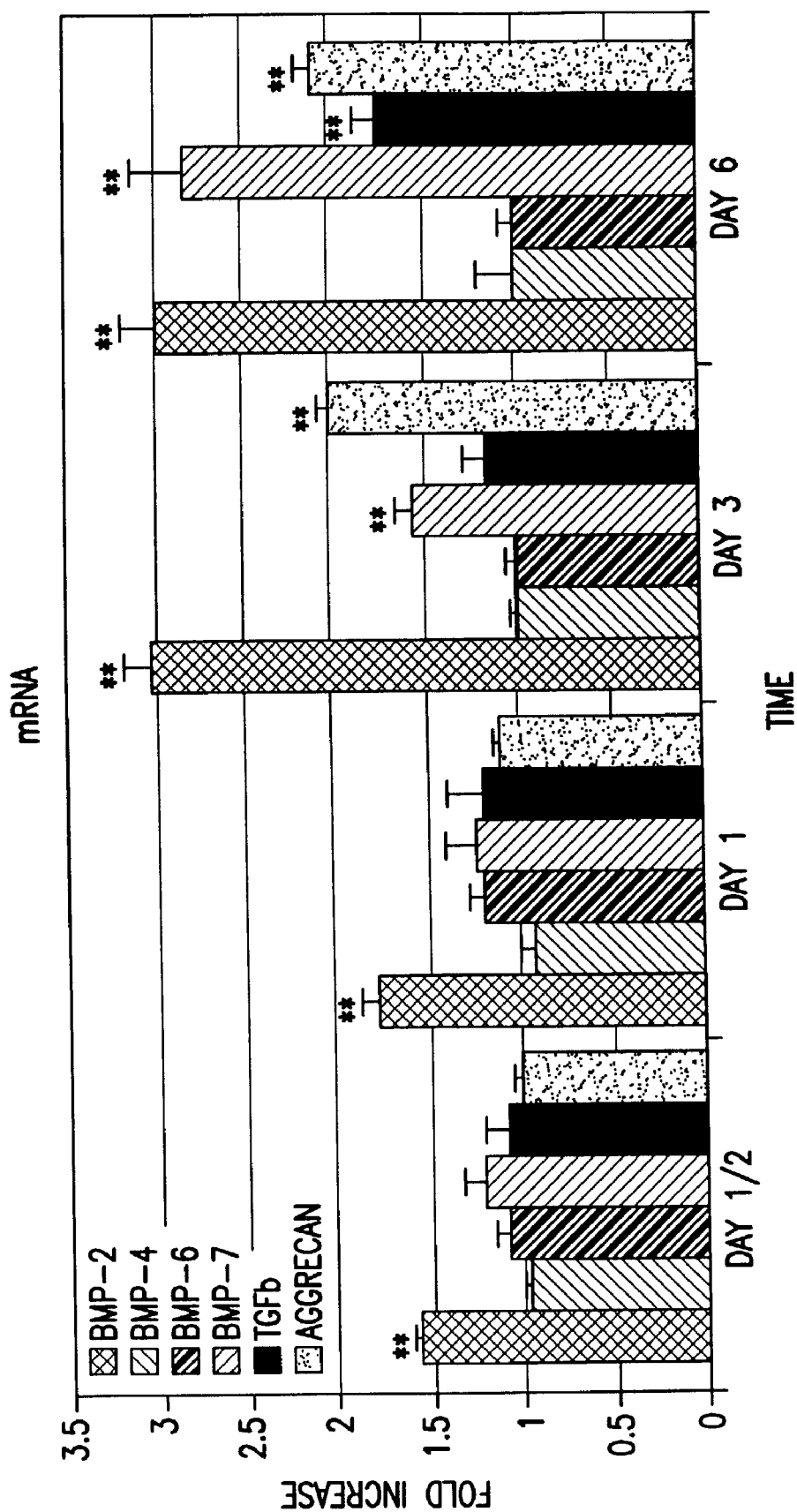
FIG. 8 is a chart showing changes in mRNA levels of BMPs and aggrecan in response to HLMP-1 over-expression.

FIG. 8 is a chart showing changes in mRNA levels of BMPs and aggrecan in response to HLMP-1 over-expression. The mRNA levels of BMP-2, BMP-4, BMP-6, BMP7, and aggrecan were determined with realtime-PCR at different time points after infection with Ad-hLMP-1 at a MOI of 25. As can be seen from FIG. 8, BMP-2 mRNA was upregulated significantly as early as 12 hours after infection with AdLMP-1. On the other hand, Aggrecan mRNA was not upregulated until 3 day after infection. Each result is expressed as mean with SD for six samples. In FIG. 8, "**" indicates data points for which the P value is <0.01 for infection with AdLMP-1 versus an untreated control.

Figure 9:
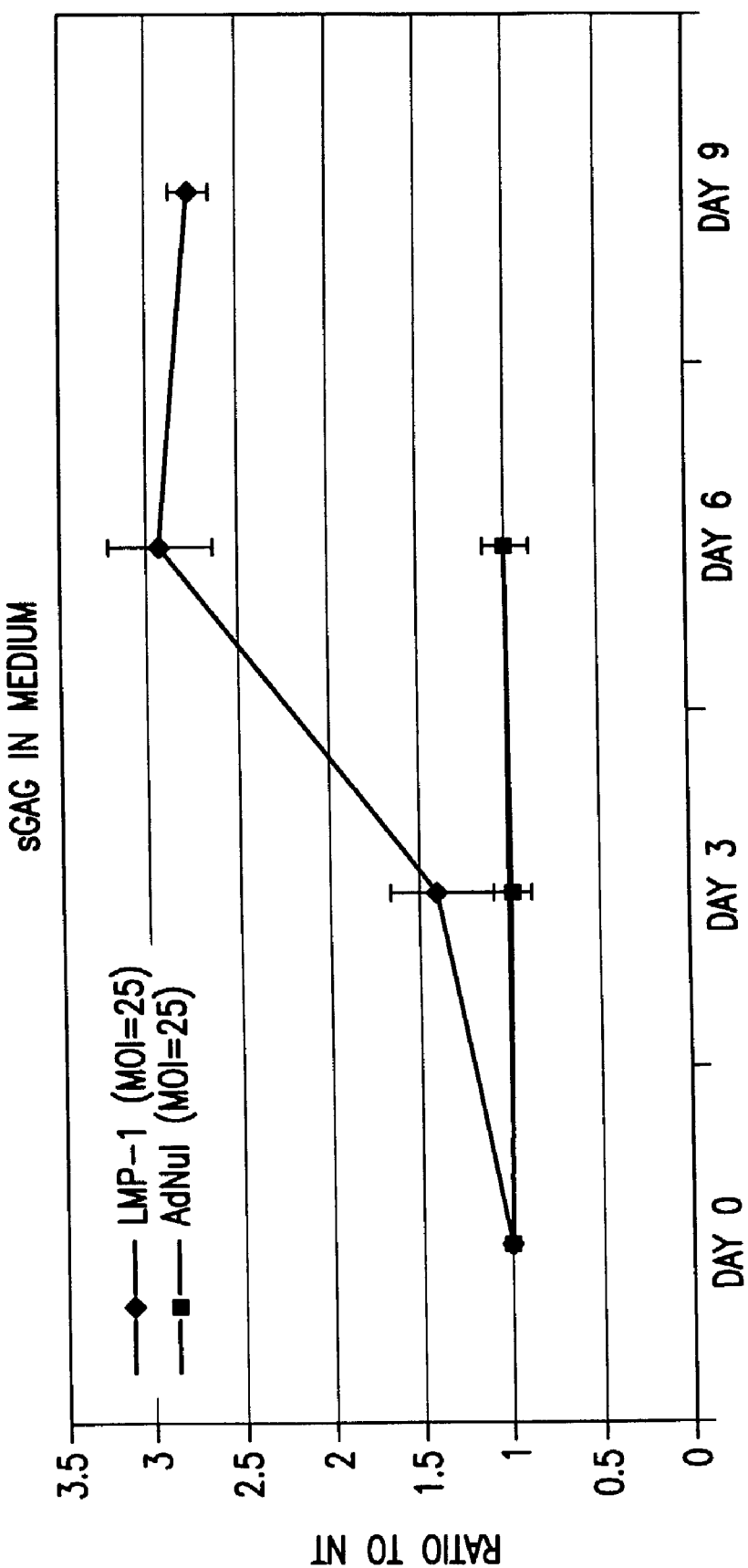
FIG. 9 is a graph showing the time course of sGAG production enhancement in response to HLMP-1 expression.

FIG. 9 is a graph showing the time course of sGAG production enhancement in response to HLMP-1 expression. For the data in FIG. 9, rat annulus cells were infected with Ad-hLMP-1 at a MOI of 25. The media was changed every three days after infection and assayed for sGAG with the DMMB assay. This data shows that sGAG production reaches a plateau at day 6 and is substantially maintained at day 9.

Figure 10:
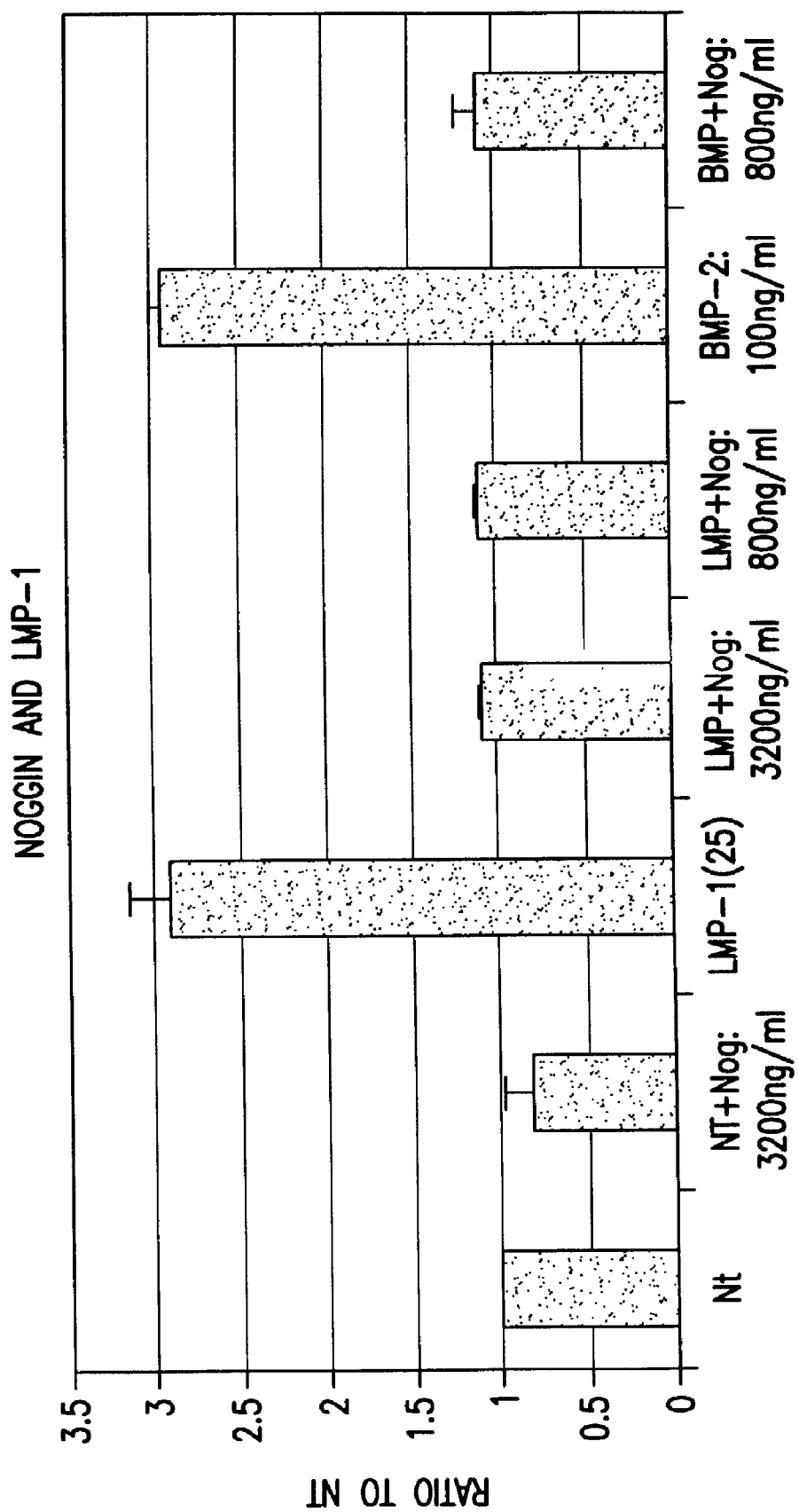
FIG. 10 is a chart showing that the LMP-1 mediated increase in sGAG production is blocked by noggin.

FIG. 10 is a chart showing the effect of noggin (a BMP antagonist) on LMP-1 mediated increase in sGAG production. As seen in FIG. 10, infection of rat annulus cells with Ad-LMP-1 at a MOI of 25 led to a three fold increase in sGAG produced between day 3 and day 6. This increase was blocked by the addition of noggin (a BMP antagonist) at concentration of 3200 ng/ml and 800 ng/m. As shown in FIG. 10, however, noggin did not significantly alter sGAG production in uninfected cells. As can also be seen in FIG. 10, stimulation with rhBMP-2 at 100 ng/ml led to a 3 fold increase in sGAG production between day 3 and day 6 after addition of BMP-2. Noggin at 800 ng/ml also blocked this increase.

Figure 11:
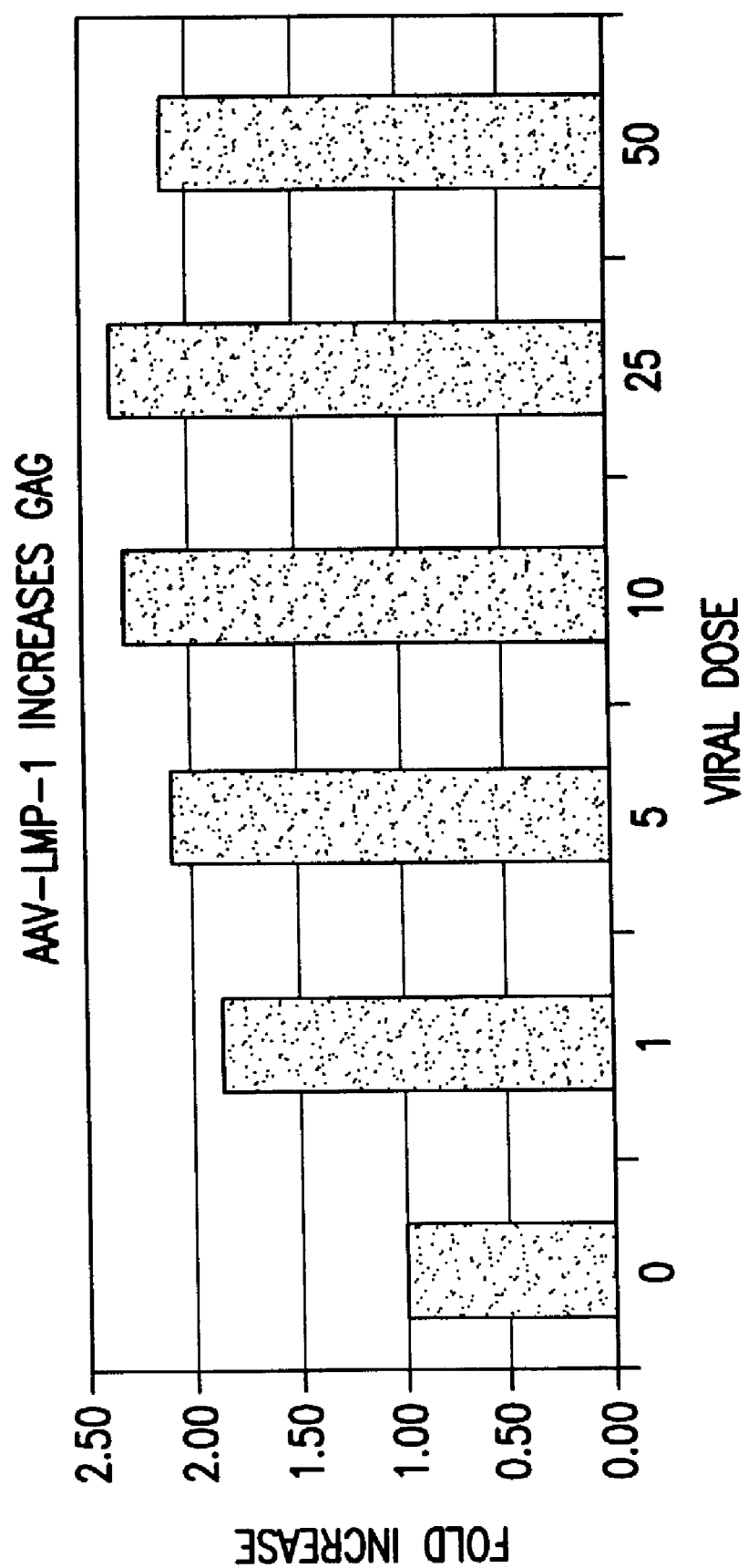
FIG. 11 is a graph showing the effect of LMP-1 on sGAG in media after day 6 of culture in monolayer.

FIG. 11 is a chart showing the effect of LMP-1 on sGAG in media after day 6 of culture in monolayer. The data points are represented as fold increase above untreated cells. As shown in FIG. 11, LMP-1 with the CMV promoter when delivered by the AAV vector is also effective in stimulating glycosaminoglycan synthesis by rat disc cells in monolayer.

TABLE 2

Primer Sequences for RT-PCR & Real-time PCR of SYBR Green

| Primer | Sequence |
| --- | --- |
| Aggrecan (forward) (SEQ ID NO: 43) | AGGATGGCTTCCACCAGTGC |
| Aggrecan (reverse) (SEQ ID NO: 44) | TGCGTAAAAGACCTCACCCTCC |
| BMP-2 (forward) (SEQ ID NO: 45) | CACAAGTCAGTGGGAGAGC |
| BMP-2 (reverse) (SEQ ID NO: 46) | GCTTCCGCTGTTTGTGTTTG |
| GAPDH (forward) (SEQ ID NO: 47) | ACCACAGTCCATGCCATCAC |
| GAPDH (reverse) (SEQ ID NO: 48) | TCCACCACCCTGTTGCTGTA |

GAPDH in Table 2 denotes glyceraldehyde phosphate dehydrogenase.

TABLE 3

Primer and Probe sequences for Real-time PCR of TaqMan ®

| Primer | Sequence |
| --- | --- |
| Over-expression LMP1 (forward) (SEQ ID NO: 49) | AATACGACTCACTATAGGGCTCGA |
| Over-expression LMP1 (reverse) (SEQ ID NO: 50) | GGAAGCCCCAAGGTGCT |

TABLE 3 -continued

Primer and Probe sequences for
Real-time PCR of TaqMan ®

| Primer | Sequence |
|---|---|
| Over-expression LMP1 (probe) (SEQ ID NO: 51) | -FAM-AGCCGGCATCATGGATTCCTTCAA-TAMRA |

TaqMan® Ribosomal RNA Control Reagents (Part number 4308329, Applied Biosystems, Foster City, Calif., U.S.A.) were used for the forward primer, reverse primer and probe of 18S ribosomal RNA (rRNA) gene.

All cited publications and patents are hereby incorporated by reference in their entirety except U.S. patent application Ser. No. 09/986,625, U.S. Pat. No. 6,858,431, U.S. patent application Ser. No. 09/721,975, U.S. Pat. No. 6,444,803, U.S. Provisional Application Nos. 60/054,219 and 60/080,407.

While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method of increasing an amount of a proteoglycan produced by a cell in a mammal comprising transfecting an isolated nucleic acid sequence encoding a Human LIM Protein-1 (HLMP-1) protein into said cell in vivo by delivering the isolated nucleic acid sequence directly into an intervertebral disc of the mammal; wherein the isolated nucleic acid sequence is operably linked to a promoter and is included within a viral vector and whereupon expression of the isolated nucleic acid sequence for the HLMP-1 protein results in the proteoglycan synthesis in the cell, and wherein said cell is selected from nucleus pulposus cells, annulus fibrosis cells and any combination thereof.

2. The method according to claim 1, wherein the cell is an intervertebral disc cell and wherein the cell is transfected in vivo by direct injection of the isolated nucleic acid into an intervertebral disc of the mammal.

3. A method of increasing an amount of a proteoglycan produced by a cell in a mammal comprising transfecting an isolated nucleic acid sequence encoding a HLMP-1 protein into said cell ex vivo and implanting said transfected cell into an intervertebral disc of the mammal, wherein the isolated nucleic acid sequence is operably linked to a promoter, wherein said cell is selected from nucleus pulposus cells, annulus fibrosis cells and any combination thereof, and whereupon expression of the isolated nucleic acid sequence for the HLMP-1 protein results in increasing the proteoglycan synthesis in the cell.

4. The method of claim 1, wherein the isolated nucleic acid is in an adenoviral vector.

5. The method of claim 1, wherein the isolated nucleic acid is in a retroviral vector.

6. The method of claim 4, wherein the adenoviral vector is Recombinant Type 5 Adenovirus comprising nucleotide sequence encoding HLMP-1 (AdHLMP-1).

7. The method of claim 1, wherein the promoter is a cytomegalovirus promoter.

8. The method of claim 3, further comprising: combining the transfected cell with a carrier prior to implantation into the mammal.

9. The method of claim 8, wherein the carrier comprises a porous matrix.

10. The method of claim 9, wherein the porous matrix comprises a synthetic polymer or collagen matrix.

11. The method of claim 3, wherein the isolated nucleic acid is in an expression vector.

12. The method of claim 11, wherein the expression vector is a viral vector.

13. The method of claim 12, wherein the viral vector is an adenoviral vector.

14. The method of claim 11, wherein the promoter is a cytomegalovirus promoter.

* * * * *

UNITED STATES PATENT AND TRADEMARK OFFICE
CERTIFICATE OF CORRECTION

| | | |
|---|---|---|
| PATENT NO. | : 7,923,250 B2 | Page 1 of 1 |
| APPLICATION NO. | : 10/292951 | |
| DATED | : April 12, 2011 | |
| INVENTOR(S) | : McKay et al. | |

It is certified that error appears in the above-identified patent and that said Letters Patent is hereby corrected as shown below:

On the Face Page, in Field (73), under "Assignee", in Column 1, Line 1, delete "Inc." and insert -- Inc. (US) --, therefor.

On Page 3, in Field (56), under "OTHER PUBLICATIONS", in Column 2, Line 36, delete "Tratment" and Insert -- Treatment --, therefor.

On Page 4, in Field (56), under "OTHER PUBLICATIONS", in Column 1, Line 18, delete "Expession" and insert -- Expression --, therefor.

On Page 4, in Field (56), under "OTHER PUBLICATIONS", in Column 2, Line 66, delete "Asessment" and insert -- Assessment --, therefor.

On Page 5, in Field (56), under "OTHER PUBLICATIONS", in Column 1, Line 56, delete "Oseoblast" and insert -- Osteoblast --, therefor.

In Column 5, Line 27, delete "("HLMPI")." and insert -- ("HLMP1"), --, therefor.

In Column 10, Line 23, delete "susbstantially" and insert -- substantially --, therefor.

In Column 16, Line 43, delete "centrifuiged." and insert -- centrifuged --, therefor.

In Column 17, Line 3, delete "Conner." and insert -- Conner, --, therefor.

In Column 17, Line 54, delete "hftp://" and insert -- http:// --, therefor.

In Column 24, Line 25, delete "(mu/+;" and insert -- (rnu/+; --, therefor.

Signed and Sealed this
Twenty-first Day of June, 2011

David J. Kappos
*Director of the United States Patent and Trademark Office*